US007183101B2

(12) United States Patent
Arigoni et al.

(10) Patent No.: US 7,183,101 B2
(45) Date of Patent: Feb. 27, 2007

(54) NCC2705—THE GENOME OF A BIFIDOBACTERIUM

(75) Inventors: Fabrizio Arigoni, Geneva (CH); Michèle Delley, Vauderens (CH); Beat Mollet, Lausanne (CH); Raymond David Pridmore, Lausanne (CH); Mark Alan Schell, Athens, GA (US); Thomas Pohl, Constance (DE); Marie-Camille Zwahlen, Lausanne (CH)

(73) Assignee: Nestec S.A., Vevey (CH)

( * ) Notice: Subject to any disclaimer, the term of this patent is extended or adjusted under 35 U.S.C. 154(b) by 265 days.

(21) Appl. No.: 10/470,565

(22) PCT Filed: Jan. 30, 2002

(86) PCT No.: PCT/EP02/00958

§ 371 (c)(1), (2), (4) Date: Jan. 7, 2004

(87) PCT Pub. No.: WO02/074798

PCT Pub. Date: Sep. 26, 2002

(65) Prior Publication Data

US 2004/0126870 A1    Jul. 1, 2004

(30) Foreign Application Priority Data

Jan. 30, 2001    (EP)    ............................ 01102050

(51) Int. Cl.
*C12N 1/20*    (2006.01)

(52) U.S. Cl. .................. 435/252.9; 435/252.1

(58) Field of Classification Search ............. 435/252.9, 435/252.1
See application file for complete search history.

(56) References Cited

U.S. PATENT DOCUMENTS 4,913,913 A * 4/1990 Takano et al. ................ 426/43
5,494,664 A * 2/1996 Brassart et al. ............ 424/93.4

FOREIGN PATENT DOCUMENTS

EP    0 768 375 A1    4/1997

OTHER PUBLICATIONS

Hatcher et al., "Augmentation of macrophage phagocytic activity by cell-free extracts of selected lactic acid-producing bacteria," J Dairy Sci 76:2485-2492, 1993.*
ATCC collection for Bifidobacterium longum, on-line records, http://www.atcc.org/common/catalog/num Search/numResults.cfm, printed from the Internet on Apr. 26, 2006.*

(Continued)

*Primary Examiner*—Jon Weber
*Assistant Examiner*—Rosanne Kosson
(74) *Attorney, Agent, or Firm*—Bell, Boyd & Lloyd LLC

(57) ABSTRACT

A novel microorganism of the genus *Bifidobacterium longum*, in particular to its genomic and plasmid sequence and to a method of producing polypeptides of said *Bifidobacterium*, respectively. Also methods of detecting these nucleic acids or polypeptides, respectively. A data carrier is provided comprising nucleotide sequences and/or polypeptide sequences of NCC2705. In addition, the *Bifidobacterium longum* strain NCC2705 and also to food and pharmaceutical compositions containing said *Bifidobacterium* or active components thereof for the prevention and/or treatment of diarrhoea brought about by rotaviruses and pathogenic bacteria are provided.

1 Claim, 5 Drawing Sheets

PATHOGENS SENSITIVITY TO HUMAN BIFIDOBACTERIA NCC 2705

OTHER PUBLICATIONS

Rossi et al. article entitled "Nucleotide sequence, expression and transcriptional analysis of the *Bifidobacterium longum* MB 219 *lacZ* gene" *Arch Microbiol*, (2000) 174: pp. 74-80.

Tomb et al. article entitled "The complete genome sequence of the gastric pathogen *Helicobacter pylori*" *Nature*, vol. 388, Aug. 7, 1997, pp. 539-547.

Document No. XP-002171486 entitled "Sequence and characteristics of the *Bifidobacterium longum* gene encoding L-lactate dehydrogenase and the primary structure of the enzyme: A new feature of the allosteric site", May 26, 1990.

Document No. XP-002177946 entitled "Amplification of bacterial heat shock protein 60 gene using inverse PCR method", Jan. 2, 2001.

Document No. XP-002177948 entitled "Phylogenetic development research of Bifidobacteria through the hsp60 gene", Dec. 21, 1999.

Document No. XP-002177952 entitled "Phylogenetic Relationship of Bifidobacterium", Mar. 16, 2000.

Document No. XP-002177956 entitled "Amplification of bacterial heat shock protein 60 gene using inverse PCR method", Jan. 2, 2001.

* cited by examiner

NCC2705—THE GENOME OF A BIFIDOBACTERIUM

This application is the U.S. national phase of International Application No. PCT/EP02/00958, filed on Jan. 30, 2002, which claims priority to European Application No. 01102050.0, filed on Jan. 30, 2001.

BACKGROUND OF THE INVENTION

The present invention pertains to a novel microorganism of the genus *Bifidobacterium longum*, in particular to its genomic and plasmid sequence and to a method of producing polypeptides of said *Bifidobacterium*, respectively. The invention also relates to methods of detecting and using the nucleic acids and polypeptides.

Organisms that produce lactic acid as a major metabolic component have been known since decades. These bacteria are normally found in milk or in milk processing factories, respectively, living or decaying plants but also in the intestine of man and animals. These microorganisms, summarized under the term "lactic acid bacteria", represent a rather inhomogeneous group and comprise the genera *Lactococcus, Lactobacillus, Streptococcus, Bifidobacterium, Pediococcus* etc.

Lactic acid bacteria have been utilized by mankind as fermenting agents for the preservation of food taking benefit of a low pH and the action of products generated during the fermentative activity thereof to inhibit the growth of spoilage bacteria. In addition, lactic acid bacteria have also been used for preparing a variety of different foodstuff such as cheese, yogurt and other fermented dairy products from milk.

Quite recently lactic acid bacteria have attracted a great deal of attention in that some strains have been found to exhibit valuable properties to man and animals upon ingestion. In particular, specific strains of the genus *Lactobacillus* or *Bifidobacterium* have been found to pass the gastrointestinal tract in a viable and live form without getting destroyed in the upper part thereof, especially by the impact of the low pH prevailing in the stomach and be able to colonize the intestinal mucosa, with their temporary or sustained maintenance in the gut being presumed to bring about numerous positive effects on the health of the living beings. These strains are generically termed probiotics.

EP 0 768 375 discloses such a specific strain of the genus *Bifidobacterium*, that is capable to become implanted in the intestinal flora and may adhere to intestinal cells. This *Bifidobacterium* is reported to assist in immuno-modulation, being capable to competitively exclude adhesion of pathogenic bacteria to intestinal cells, thus supporting the maintenance of the individual's health.

In view of the valuable properties particular strains of lactic acid bacteria may provide, there is a desire in the art for additional lactic acid bacterial strains that are beneficial to the well being of man and/or animal. In addition, a more detailed information is desired relating to the biology of these strains, in particular as regards the interaction with the hosts, the phenomena of passing different environmental conditions in the gut as well as having the capability to adhere to the intestine's mucosa and eventually the involvement in the enhancement of the immune system and defense against pathogens, which information will allow a better understanding of these mechanisms.

Consequently, a problem of the present invention is to provide substantial data about bacterial strains that exhibit properties beneficial for man and/or animals.

SUMMARY OF THE INVENTION

In view of said problem, a subject of the present invention resides in the nucleotide sequence having the sequence SEQ. ID. NO. 1 of the lactic acid bacterium *Bifidobacterium longum* NCC2705 genome and/or the nucleotide sequence SEQ ID. NO. 2 of the plasmid contained tehrein. The invention is, however, not limited to the sequences indicated in SEQ. ID. NO. 1 and SEQ ID. NO. 2, respectively, but encompasses genomes and nucleotides encoding polypeptides of strain variants, polymorphisms, allelic variants, and mutants thereof.

The invention also relates to methods of detecting these nucleic acids or polypeptides, respectively. A data carrier is provided comprising nucleotide sequences and/or polypeptide sequences of NCC2705. In addition, the present invention pertains to the *Bifidobacterium longum* strain NCC2705 and also to food and pharmaceutical compositions containing said *Bifidobacterium* or active components thereof for the prevention and/or treatment of diarrhoea brought about by rotaviruses and pathogenic bacteria.

Additional features and advantages of the present invention are described in, and will be apparent from, the following Detailed Description of the Invention and the figures.

BRIEF DESCRIPTION OF THE DRAWINGS

In the figures.

DETAILED DESCRIPTION OF THE INVENTION

Figure 1:
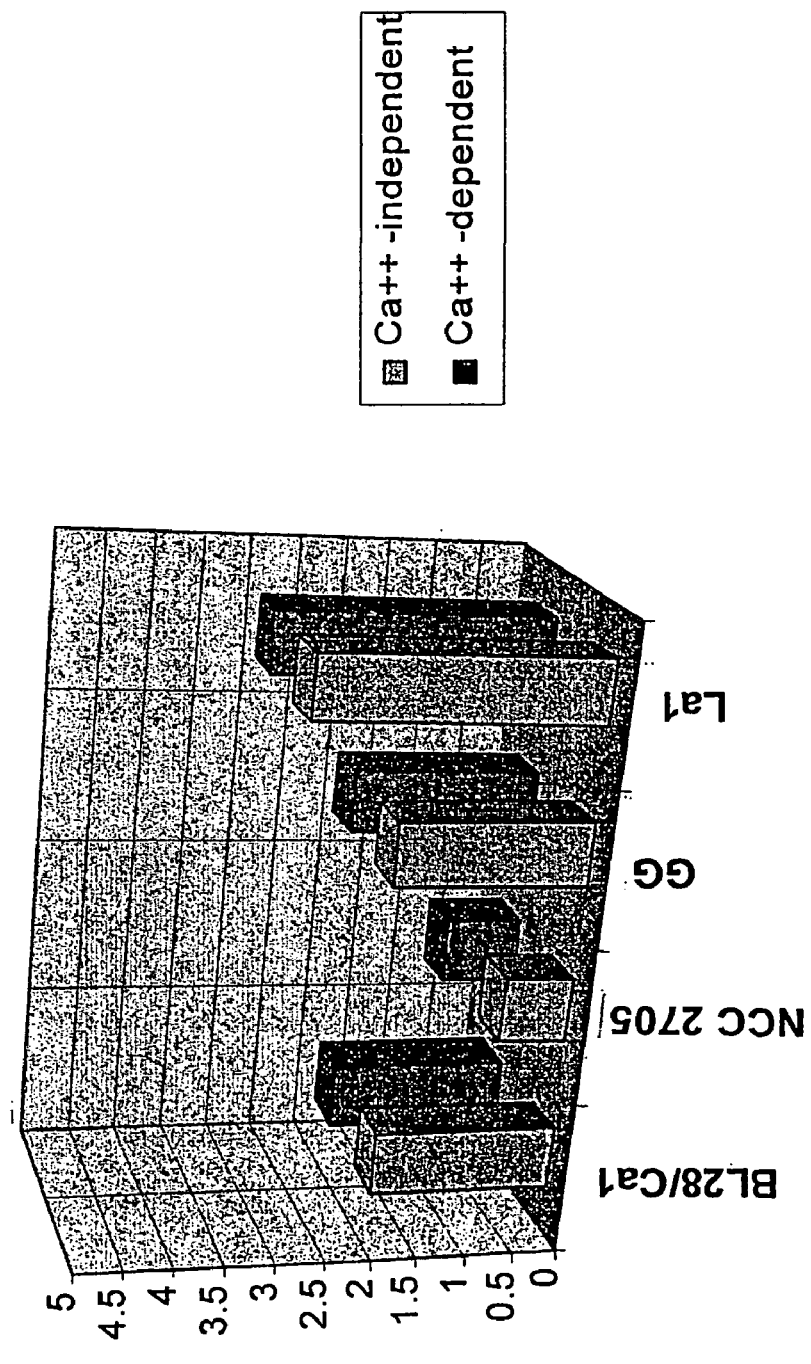
FIG. 1 shows a graph, indicating the capability of *Bifidobacterium longum* NCC 2705 to adhere to human intestinal cells in culture; as a comparison another *Bifidobacterium* strain BL28 Cal was used.

The present invention is based on whole-genome sequencing of the genome of the *Bifidobacterium longum* strain NCC 2705, that has been deposited with the Collection Nationale De Cultures De Micro-organismes (CNCM), at Institute Pasteur, 28, rue du Dr Roux 75724 Paris Cédex 15 France according to the Budapest Treaty on Jan. 29, 2001 receiving the deposit no. CNCM I-2618.

In a first aspect the present invention relates to nucleotide sequences selected from the group comprising (a) the nucleotide sequence of SEQ. ID. NO. 1; (b) a nucleotide sequence exhibiting at least 90% identity with the sequence of SEQ. ID. NO. 1; or (c) a nucleotide sequence that is homologous or hybridizes to SEQ ID. No. 1 under stringent conditions, or parts thereof.

In another aspect the invention relates to nucleotide sequences selected from the group comprising (a) the nucleotide sequence of SEQ. ID. NO. 2; (b) a nucleotide sequence exhibiting at least 90% identity with the sequence of SEQ.

ID. NO. 2; or (c) a nucleotide sequence that is homologous or hybridizes to SEQ ID. NO. 2 under stringent conditions or parts thereof.

The terms genome or genomic sequence shall be understood to mean the sequence of the chromosome of *Bifidobacterium longum*. The term plasmid shall be understood to designate any extrachromosomal piece of DNA contained in the *Bifidobacterium* of the present invention. Nucleotide sequence, polynucleotide or nucleic acid are understood to desigante a double-stranded DNA, a single-stranded DNA or transcriptional products of the said DNAs at various length including oligonuclotides of about 10 to 100 nucleotides in length.

A homologous nucleotide sequence according to the present invention is understood to mean a nucleotide sequence having a percentage identity with the bases of the nucleotide sequence SEQ. ID. NO. 1 or SEQ. ID. NO. 2 of at least 90% and more preferably 95%, 96%, 97%, 98% or 99%. The said homologous may comprise, e.g., the sequences corresponding to the genomic sequence or to the sequences of its representative fragments of a bacterium belonging to the *Bifidobacterium* species, preferably the *Bifidobacterium longum* species, as well as the sequences corresponding to the genomic sequence or to the sequences of its representative fragments of a bacterium belonging to the variants of the species *Bifidobacterium*. In the present invention, the terms species and genus are mutually interchangeable.

These homologous sequences may thus correspond to variations linked to mutations within the same species or between species and may correspond in particular to truncations, substitutions, deletions and/or additions of at least one nucleotide. The said homologous sequences may also correspond to variations linked to the degeneracy of the genetic code or to a bias in the genetic code which is specific to the family, to the species or to the variant and which are likely to be present in *Bifidobacterium*.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (see e.g. Pearson and Lipman, 1988, Proc. Natl. Acad. Sci. USA 85 (8): 2444–2448; Altschul et al., 1990, J. Mol. Biol. 215 (3): 403–410; Thompson et al., 1994, Nucleic Acids Res. 22 (2): 4673–4680; Higgins et al., 1996, Methods Enzymol. 266: 383–402; Altschul et al., 1990, J. Mol. Biol. 215 (3): 403–410; Altschul et al., 1993, Nature Genetics 3: 266–272).

In a particularly preferred embodiment, protein and nucleic acid sequence homologies are evaluated using the Basic Local Alignment Search Tool ("BLAST") which is well known in the art (supra). In particular, four specific BLAST programs have been used to perform the following task:

(1) BLASTP: Compares an amino acid query sequence against a protein sequence database (2) BLASTN: Compares a nucleotide query sequence against a nucleotide sequence database (3) BLASTX: Compares a nucleotide query sequence translated in all reading frames against a protein sequence database (4) TBLASTN: Compares a protein query sequence against a nucleotide sequence database dynamically translated in all reading frames Among these representative fragments, those capable of hybridizing under stringent conditions with a nucleotide sequence according to the invention are preferred. Hybridization under stringent conditions means that the temperature and ionic strength conditions are chosen such that they allow hybridization to be maintained between two complementary DNA fragments. Such conditions of high stringency may e.g. be achieved by carrying out the hybridisation at a preferred temperature of 65° C. in the presence of SSC buffer, e.g. 1×SSC corresponding to 0.15 M NaCl and 0.05 M Na-citrate. The washing steps may be, for example, the following: 2×SSC, 0.1% SDS at room temperature followed by three washes with 1×SSC, 0.1% SDS; 0.5×SSC, 0.1% SDS; 0.1×SSC, 0.1% SDS at 68 C for 15 minutes.

The nucleotide sequences SEQ. ID. NO. 1 and SEQ. ID. NO. 2, respectively, have been obtained by sequencing the genome of and the plasmid contained in *Bifidobacterium longum* NCC2705 by the method of directed sequencing after fluorescent automated sequencing of the inserts of clones and assembling of these sequences of nucleotide fragments (inserts) by means of softwares. To this end, fragments of the genome were created, ligated into suitable vectors for amplification and propagation and the corresponding fragments were sequenced. Overlaps and the final arrangement of the fragments, the nucleotide sequence thereof, were assessed by the aid of appropriate softwares.

The present invention may be utilized for producing polypeptides by using the knowledge of the open reading frames (ORFs) as derived from SEQ. ID. NO. 1. Therefore, according to another aspect the present invention provides a method of producing a polypeptide by choosing an open reading frame (ORF) of the *Bifidobacterium longum* genome and expressing the polypeptide desired according to well known techniques.

Nucleic acid molecules derived from the genomic sequence as identified by SEQ. ID. NO. 1 may be obtained, by e.g. specific amplification of the corresponding sequence using the polymerase chain reaction. Due to the sequence information provided herein the skilled person may design and synthesize any suitable primer nucleotide and amplify a fragment of interest using the polymerase chain reaction. Therefore, the present invention also comprises nucleotide sequences selected from sequence SEQ. ID. NO. 1 which can be used as a primer for the amplification of nucleic acid sequences. Other techniques for amplifying the target nucleic acid may of course be also be used, such as e.g. the TAS (Transcription-based Amplification System) technique, the 3SR (Self-Sustained Sequence Replication) technique, the NASBA (Nucleic Acid Sequence Based Amplification) technique, the SDA (Strand Displacement Amplification) technique or the TMA (Transcription Mediated Amplification) technique etc.

The (poly)nucleotides may also be used as probes and techniques for amplifying or modifying a nucleic acid serving as a probe, such as e.g the LCR (Ligase Chain Reaction) technique, the RCR (Repair Chain Reaction) technique, the CPR (Cycling Probe Reaction) technique or the Q-beta-replicase amplification technique may well be applied.

The present invention, therefore, envisages both hybridization (detection) probes and primers for detecting a nucleoide sequence (target nucleotide) of the present invention. In the case of the target being a RNA molecule, e.g. a mRNA, said mRNA may be directly detected or transformed to a cDNA prior to detection.

Alternatively, in order to obtain fragments of the nucleic acid represented by SEQ. ID. NO.1 the *Bifidobacterium longum* genomic DNA may be subjected to digestion with selected restriction enzymes, with the fragments being separated by e.g. electrophoresis or another suitable separation technique. Such techniques are well known in the art and are inter alia disclosed in Sambrook et al. A Laboratory Manual, Cold Spring Harbor, 1992. Such fragments may easily be obtained by isolating the genomic DNA of *Bifidobacterium longum* NCC2705 (CNCM I-2618) and performing the necessary steps.

In an alternative form the nucleic acids may also be obtained by chemical synthesis when they are not too large in size according to methods well known to a person skilled in the art.

Modified nucleotide sequences shall be understood to mean any nucleotide sequence obtained by mutagenesis according to techniques well known to a skilled person and exhibiting modifications in relation to the normal sequences, for example mutations in the regulatory and/or promoter sequences for the expression of a polypeptide, in particular leading to a modification of the level of expression of the said polypeptide or to a modulation of the replicative cycle. Modified nucleotide sequence will also be understood to mean any nucleotide sequence encoding a modified polypeptide as defined below.

During the study of the *Bifidobacterium longum* genome the following annotation could be performed as identified by sequences having an open reading frame as identified by NO. 1 to NO. 1147, shown in the table I below.

TABLE I

| | Gene Name | Start | Stop | Strand | Function | Best Hit | Best Score |
|---|---|---|---|---|---|---|---|
| NO. 1a | BL0002 | 833 | 2458 | + | chaperone (groEL) | trembl\|M17705\|MBBCG_1 | 0 |
| NO. 2a | BL0005 | 3719 | 4450 | + | response regulator of two component system | trembl\|Z80226\|MTCY369_2 | 1.00E−72 |
| | BL0006 | 4622 | 6472 | + | histidine kinase sensor of two-component system | trembl\|Z80226\|MTCY369_3 | 1.00E−54 |
| NO. 4 | BL0007 | 6542 | 6931 | + | cold shock protein(cspA) | trembl\|AL022004\|MTV043_63 | 1.00E−25 |
| | BL0008 | 6940 | 8127 | + | narrowly conserved hypothetical protein with | swiss\|Q10539\|Y877_MYCTU | 2.00E−37 |
| NO. 6 | BL0010 | 9354 | 11963 | + | protease (clpC) | trembl\|AL049628\|SCE94_24 | 0 |
| NO. 7 | BL0011 | 12143 | 13462 | Complement | cytosine deaminase (EC 3.5.4.1) (cytosine | pironly\|D83590\|D83590 | 5.00E−102 |
| NO. 8 | BL0013 | 15297 | 16673 | + | proline/betaine transporter (proP) | trembl\|AL158057\|SC10G8_20 | 2.00E−85 |
| NO. 9 | BL0014 | 16759 | 17517 | + | creatinine amidohydrolase; creatininase (EC | trembl\|AB007122\|AB007122_5 | 2.00E−60 |
| NO. 10 | BL0015 | 17689 | 19482 | + | 5′-nucleotidase family protein | trembl\|AE001909\|AE001909_7 | 4.00E−24 |
| NO. 11 | BL0016 | 19688 | 21148 | complement | narrowly conserved hypothetical protein with | trembl\|Z98209\|MTCY154_10 | 1.00E−49 |
| NO. 12 | BL0017 | 21248 | 22648 | + | histidyl-trna synthetase (EC 6.1.1.21) | pironly\|A82586\|A82586 | 4.00E−68 |
| NO. 13 | BL0018 | 22684 | 24483 | + | aspartyl-trna synthetase (EC 6.1.1.12) | swiss\|Q50649\|SYD_MYCTU | 0 |
| NO. 14 | BL0021 | 26476 | 27291 | + | atp-binding protein of abc transporter for | trembl\|AL020958\|SC4H8_16 | 5.00E−102 |
| NO. 15 | BL0022 | 27362 | 28162 | + | glutamate-binding protein of abc transporter | trembl\|AL020958\|SC4H8_15 | 5.00E−72 |
| NO. 16 | BL0023 | 28162 | 28839 | + | permease protein of abc transporter for | trembl\|AL020958\|SC4H8_14 | 3.00E−52 |
| NO. 17 | BL0024 | 28845 | 29945 | + | permease protein of abc transporter for | trembl\|AL020958\|SC4H8_13 | 3.00E−44 |
| NO. 18 | BL0025 | 30034 | 31575 | + | hypothetical secreted protein with probable acid | trembl\|AL023496\|SC1A6_17 | 3.00E−50 |
| NO. 19 | BL0027 | 32653 | 33579 | + | narrowly conserved hypothetical protein with | trembl\|AE001875\|AE001875_9 | 3.00E−47 |
| NO. 20 | BL0028 | 33713 | 36280 | + | probable dead box-like helicase | tremblnew\|U42580\|PB42580_239 | 3.00E−46 |
| NO. 21 | BL0029 | 36363 | 37742 | + | widely conserved hypothetical protein with | swiss\|Q50739\|YP59_MYCTU | 5.00E−118 |
| NO. 22 | BL0030 | 37800 | 38522 | + | response regulator of two-component system | trembl\|U01971\|MT01971_1 | 5.00E−60 |
| NO. 23 | BL0031 | 38519 | 40216 | + | histidine kinase sensor of two-component system | trembl\|Z95121\|MTY20B11_20 | 2.00E−72 |
| NO. 24 | BL0033 | 42259 | 43242 | + | probable solute binding protein of abc | tremblnew\|AE005655\|AE005655_4 | 5.00E−33 |
| NO. 25 | BL0034 | 43383 | 44924 | + | atp binding protein of abc transporter | tremblnew\|AE005655\|AE005655_5 | 5.00E−125 |
| NO. 26 | BL0035 | 44926 | 45996 | + | probable abc transport system permease protein | swiss\|P39328\|YTFT_ECOLI | 6.00E−52 |
| NO. 27 | BL0036 | 45993 | 47015 | + | probable abc transporter permease protein for | tremblnew\|AE005655\|AE005655_7 | 3.00E−44 |
| NO. 28 | BL0037 | 47238 | 48695 | complement | probable efflux-type transporter | tremblnew\|AX066097\|AX066097_1 | 4.00E−52 |
| NO. 29 | BL0038 | 49084 | 49980 | + | conserved protein with hydroxyacid dehydrogenase | pironly\|B82343\|B82343 | 3.00E−30 |
| NO. 30 | BL0043 | 52518 | 54950 | complement | possible fused atp binding protein and permease | trembl\|AE000829\|AE000829_9 | 3.00E−56 |
| NO. 31 | BL0047 | 58071 | 58838 | + | similar to mycobacterium tuberculosis | trembl\|AE001936\|AE001936_11 | 7.00E−61 |
| NO. 32 | BL0048 | 59063 | 60322 | + | probable aminotransferase (EC 2.6.1.—) | trembl\|AL031514\|SC2H4_4 | 5.00E−22 |
| NO. 33 | BL0049 | 60331 | 61155 | + | atp binding protein of abc transporter | trembl\|AE002076\|AE002076_5 | 3.00E−23 |

TABLE I-continued

| | Gene Name | Start | Stop | Strand | Function | Best Hit | Best Score |
|---|---|---|---|---|---|---|---|
| NO. 34 | BL0052 | 67189 | 69951 | + | dna ligase (EC 6.5.1.2) (polydeoxyribonucleotide | swiss\|Q9Z585\|DNLJ_STRCO | 5.00E−141 |
| NO. 35 | BL0053 | 70127 | 71242 | + | hypothetical protein with duf059 and 4fe-4s iron | swiss\|O33225\|MRP_MYCTU | 4.00E−85 |
| NO. 36 | BL0055 | 72964 | 73779 | + | sugar permease of abc transporter system | trembl\|AL138851\|SCE59_3 | 1.00E−45 |
| NO. 37 | BL0058 | 77028 | 77987 | + | possible butyryl-coa dehydrogenase | trembl\|AE000948\|AE000948_16 | 3.00E−46 |
| NO. 38 | BL0059 | 78166 | 79275 | + | narrowly conserved hypothetical protein with | trembl\|AL117387\|SCF41_25 | 3.00E−43 |
| NO. 39 | BL0062 | 80643 | 81185 | + | protein similar to ycbi of *b. subtilis* | trembl\|D50453\|BSD453_38 | 1.00E−24 |
| NO. 40 | BL0063 | 81212 | 82012 | complement | hypothetical transmembrane protein with unknown | swiss\|P74369\|YG47_SYNY3 | 2.00E−34 |
| NO. 41 | BL0064 | 82009 | 82797 | complement | atp binding protein of abc transporter | pironly\|F82198\|F82198 | 6.00E−20 |
| NO. 42 | BL0065 | 82902 | 83468 | + | elongation factor p (ef-p) (efp) | swiss\|P95019\|EFP_MYCTU | 5.00E−67 |
| NO. 43 | BL0066 | 83523 | 84095 | + | nusb antitermination protein (nusB) | swissnew\|P95020\|NUSB_MYCTU | 7.00E−21 |
| NO. 44 | BL0067 | 84286 | 85509 | + | carbamoyl-phosphate synthase small chain (EC | swissnew\|P71811\|CARA_MYCTU | 5.00E−120 |
| NO. 45 | BL0068 | 85511 | 88894 | + | carbamoyl-phosphate synthase large chain (EC | trembl\|AE001016\|AE001016_6 | 0 |
| NO. 46 | BL0069 | 88894 | 89814 | + | orotidine 5'-phosphate decarboxylase (EC | swiss\|P77898\|DCOP_MYCTU | 6.00E−40 |
| NO. 47 | BL0070 | 89994 | 90584 | + | guanylate kinase (EC 2.7.4.8) (gmp kinase) | swiss\|P71659\|KGUA_MYCTU | 6.00E−44 |
| NO. 48 | BL0071 | 90586 | 91293 | complement | possible exonuclease (dnaQ) | swiss\|Q9ZHF6\|DPO3_THEMA | 4.00E−22 |
| NO. 49 | BL0072 | 91440 | 93695 | + | tetracycline resistance protein tetq (teta(q)1) | trembl\|Y08615\|BFTETAQ3_2 | 2.00E−63 |
| NO. 50 | BL0074 | 94496 | 95242 | + | permease protein of abc transporter system | trembl\|AE001537\|AE001537_3 | 5.00E−53 |
| NO. 51 | BL0075 | 95229 | 95903 | + | permease of abc transporter system for amino | trembl\|AL139075\|CJ11168X2_122 | 1.00E−54 |
| NO. 52 | BL0076 | 95896 | 96687 | + | atp binding protein of abc transporter for | trembl\|AE001537\|AE001537_5 | 8.00E−64 |
| NO. 53 | BL0077 | 96753 | 97655 | + | probable solute-binding protein for | trembl\|AL139076\|CJ11168X3_289 | 1.00E−71 |
| NO. 54 | BL0078 | 97891 | 99129 | + | cystathionine beta-lyase (beta-cystathionase ec | trembl\|AF131880\|AF131880_1 | 5.00E−98 |
| NO. 55 | BL0080 | 99771 | 101042 | complement | is30-type transposase | trembl\|AL021646\|MTV014_36 | 1.00E−78 |
| NO. 56 | BL0084 | 102563 | 103462 | + | narrowly conserved hypothetical protein with | tremblnew\|AC008261\|AC008261_3 | 7.00E−47 |
| NO. 57 | BL0086 | 104503 | 105297 | complement | glutamate racemase (EC 5.1.1.3) (murI) | pironly\|G83062\|G83062 | 2.00E−40 |
| NO. 58 | BL0087 | 105456 | 106298 | + | diaminopimelate epimerase (EC 5.1.1.7) (dap | swiss\|O69969\|DAPF_STRCO | 7.00E−30 |
| NO. 59 | BL0089 | 107179 | 108072 | + | conserved hypothetical protein with | tremblnew\|AP001515\|AP001515_17 | 4.00E−32 |
| NO. 60 | BL0092 | 110307 | 111881 | + | probable dna helicase ii (uvrD) | swiss\|O53344\|UVRD_MYCTU | 1.00E−84 |
| NO. 61 | BL0093 | 111951 | 113696 | complement | narrowly conserved hypothetical protein with | trembl\|U00016\|ML016_32 | 1.00E−38 |
| NO. 62 | BL0094 | 113917 | 114798 | + | hypothetical protein with unknown function | trembl\|AL096852\|SCE19A_34 | 1.00E−42 |
| NO. 63 | BL0097 | 117499 | 118689 | + | 1-deoxy-d-xylulose 5-phosphate reductoisomerase | trembl\|Z74024\|MTCY274_1 | 4.00E−98 |
| NO. 64 | BL0098 | 118698 | 119909 | + | protein with similarity to gcpe of *p. stuarti* | swissnew\|Q9X7W2\|GCPE_STRCO | 5.00E−142 |
| NO. 65 | BL0100 | 121792 | 122511 | + | conserved hypothetical protein with unknown | trembl\|AL137166\|SCC121_13 | 8.00E−55 |
| NO. 66 | BL0101 | 122508 | 123302 | + | undecaprenyl pyrophosphate synthetase (EC | swiss\|O05837\|UPPS_MYCTU | 4.00E−82 |
| NO. 67 | BL0102 | 123458 | 124660 | complement | inosine-uridine preferring nucleoside hydrolase | trembl\|AE001900\|AE001900_5 | 5.00E−23 |
| NO. 68 | BL0103 | 124784 | 125854 | complement | possible solute binding protein of abc | trembl\|AE001726\|AE001726_3 | 6.00E−29 |
| NO. 69 | BL0104 | 126113 | 126895 | complement | possible permease protein of abc transporter | trembl\|AE001726\|AE001726_4 | 2.00E−28 |
| NO. 70 | BL0105 | 127091 | 128647 | complement | sucrose-6-phosphate hydrolase (EC 3.2.1.26) | swiss\|P40714\|CSCA_ECOLI | 2.00E−92 |
| NO. 71 | BL0106 | 128658 | 130160 | complement | sucrose transport protein (sucrose permease) | tremblnew\|AE005467\|AE005467_5 | 9.00E−93 |
| NO. 72 | BL0107 | 130210 | 131250 | complement | probable laci-type transcriptional regulator | trembl\|AE001777\|AE001777_1 | 3.00E−31 |
| NO. 73 | BL0108 | 131294 | 132691 | complement | hypothetical protein with similarity to serine | swissnew\|O35684\|NEUS_MOUSE | 5.00E−30 |

TABLE I-continued

| | Gene Name | Start | Stop | Strand | Function | Best Hit | Best Score |
|---|---|---|---|---|---|---|---|
| NO. 74 | BL0111 | 133788 | 135167 | complement | hypothetical metabolite transport protein | swiss|P38055|YDJE_ECOLI | 2.00E−59 |
| NO. 75 | BL0113 | 136120 | 137121 | complement | phosphomethylpyrimidine kinase (EC 2.7.4.7) | swiss|Q9ZBR6|THID_STRCO | 6.00E−54 |
| NO. 76 | BL0114 | 137436 | 140189 | complement | thiamine biosynthesis protein (thiE/thiC) | swiss|P45740|THIC_BACSU | 0 |
| NO. 77 | BL0115 | 140272 | 141216 | complement | hydroxyethylthiazole kinase (EC 2.7.1.50) | tremblnew|AP001297|AP001297_22 | 2.00E−27 |
| NO. 78 | BL0116 | 141652 | 143124 | + | glycyl-trna synthetase (EC 6.1.1.14) | swiss|O65932|SYG_MYCTU | 0 |
| NO. 79 | BL0117 | 143269 | 144513 | + | possible nifr3-like protein | trembl|AL133471|SCC82_3 | 5.00E−100 |
| NO. 80 | BL0118 | 144625 | 145836 | + | cell division protein ftsz. (ftsZ) | trembl|AF073487|AF073487_1 | 5.00E−106 |
| NO. 81 | BL0119 | 145849 | 146328 | + | conserved hypothetical protein with unknown | tremblnew|AL445403|SC2I34_2 | 6.00E−22 |
| NO. 82 | BL0122 | 148326 | 148841 | + | possible lipoprotein signal peptidase (EC | swiss|Q10764|LSPA_MYCTU | 5.00E−20 |
| NO. 83 | BL0123 | 148841 | 149803 | + | widely conserved hypothetical protein in the rlu | trembl|AL109663|SC4A10_6 | 6.00E−81 |
| NO. 84 | BL0127 | 152161 | 155730 | + | dna polymerase iii alpha subunit (dnaE) | trembl|AF108191|AF108191_1 | 0 |
| NO. 85 | BL0128 | 155819 | 156253 | + | narrowly conserved hypothetical protein with | swiss|P76148|YNEG_ECOLI | 7.00E−27 |
| NO. 86 | BL0129 | 156459 | 158336 | + | narrowly conserved hypothetical protein with | trembl|U09352|SP09352_2 | 5.00E−176 |
| NO. 87 | BL0136 | 172074 | 173576 | complement | is21-type transposase | tremblnew|AP001520|AP001520_222 | 4.00E−52 |
| NO. 88 | BL0137 | 174295 | 176634 | complement | hypothetical protein with similarity to pip | swiss|P49022|PIP_LACLA | 5.00E−37 |
| NO. 89 | BL0138 | 176631 | 179369 | complement | hypothetical protein with similarity to pip | pironly|A48653|A48653 | 8.00E−41 |
| NO. 90 | BL0139 | 179875 | 180429 | complement | possible nadph-flavin oxidoreductase (EC | tremblnew|AL446003|SC5E9_29 | 2.00E−23 |
| NO. 91 | BL0140 | 181147 | 181794 | + | hypothetical protein in pgam phosphoglycerate | trembl|AL132997|SC9G1_8 | 3.00E−24 |
| NO. 92 | BL0141 | 182202 | 183530 | + | possible solute binding protein of abc | trembl|M57692|CTPULSA_3 | 3.00E−36 |
| NO. 93 | BL0142 | 183788 | 184804 | complement | laci-type transcriptional regulator | trembl|AL136502|SCF43_17 | 2.00E−30 |
| NO. 94 | BL0143 | 185085 | 186041 | + | permease of abc transporter possibly for | swiss|P37730|AMYD_THETU | 2.00E−61 |
| NO. 95 | BL0144 | 186041 | 186883 | + | permease of abc transporter possibly for | swiss|P37729|AMYC_THETU | 4.00E−50 |
| NO. 96 | BL0146 | 187886 | 190762 | + | possible arabinosidase | trembl|U55187|BF55187_1 | 1.00E−47 |
| NO. 97 | BL0148 | 191209 | 192390 | complement | possible transposase | trembl|M86608|ISAFATPS_1 | 2.00E−54 |
| NO. 98 | BL0149 | 192651 | 194153 | + | is21-type transposase (istA) | tremblnew|AP001520|AP001520_222 | 3.00E−53 |
| NO. 99 | BL0150 | 194234 | 194935 | + | istb-like protein (istB) | tremblnew|AJ414141|AJ414141_30 | 1.00E−32 |
| NO. 100 | BL0151 | 195265 | 196677 | + | narrowly conserved hypothetical protein with | trembl|AP000004|AP000004_109 | 5.00E−76 |
| NO. 101 | BL0152 | 196740 | 198215 | complement | aromatic amino acid transport protein arop | tremblnew|AE005187|AE005187_9 | 5.00E−120 |
| NO. 102 | BL0153 | 198437 | 199006 | complement | probable tetr-like transcriptional regulator | tremblnew|AP001509|AP001509_157 | 3.00E−23 |
| NO. 103 | BL0154 | 199150 | 199851 | + | atp binding protein of abc transporter | trembl|AE000977|AE000977_7 | 8.00E−61 |
| NO. 104 | BL0156 | 203874 | 205400 | + | amino acid permease (aapA) | swiss|O06005|AAPA_BACSU | 6.00E−98 |
| NO. 105 | BL0157 | 205842 | 210560 | + | narrowly conserved hypothetical protein with | trembl|AL158061|SC6D11_2 | 2.00E−87 |
| NO. 106 | BL0158 | 210772 | 214608 | + | very narrowly conserved hypothetical protein | trembl|AL132965|ATT16K5_23 | 3.00E−37 |
| NO. 107 | BL0159 | 215104 | 215667 | complement | dna-damage-inducible protein of *escherichia coli* | tremblnew|AE005591|AE005591_13 | 1.00E−26 |
| NO. 108 | BL0162 | 216811 | 218682 | + | probable permease protein of abc transporter | trembl|AL137187|SC7A8_2 | 5.00E−112 |
| NO. 109 | BL0163 | 218897 | 220726 | + | probable permease protein of abc transporter | trembl|AL137187|SC7A8_3 | 5.00E−142 |
| NO. 110 | BL0166 | 223918 | 225015 | + | conserved hypothetical protein with tetrapyrole | trembl|AL132674|SCE87_4 | 7.00E−64 |
| NO. 111 | BL0170 | 226374 | 228239 | + | methionyl-trna synthetase (EC 6.1.1.10) | swiss|O58721|SYM_PYRHO | 5.00E−113 |
| NO. 112 | BL0173 | 230531 | 232057 | complement | aminopeptidase c (EC 3.4.22.-) (pepC) | swiss|Q56115|PEPC_STRTR | 4.00E−87 |
| NO. 113 | BL0174 | 232282 | 234510 | + | narrowly conserved hypothetical protein with | tremblnew|AE005584|AE005584_8 | 5.00E−163 |
| NO. 114 | BL0175 | 234514 | 235503 | + | probable arac/xyls-type transcriptional | tremblnew|AE005584|AE005584_6 | 5.00E−20 |

TABLE I-continued

| | Gene Name | Start | Stop | Strand | Function | Best Hit | Best Score |
|---|---|---|---|---|---|---|---|
| NO. 115 | BL0176 | 235675 | 236832 | complement | probable laci-type transcriptional regulator | trembl|AE001777|AE001777_1 | 3.00E−31 |
| NO. 116 | BL0177 | 237206 | 238615 | + | possible alpha-galactosidase ec 3.2.1.22 | tremblnew|AP001513| AP001513_143 | 1.00E−95 |
| NO. 117 | BL0179 | 239416 | 241278 | + | probable permease protein of abc transporter | tremblnew|AP001511| AP001511_14 | 5.00E−105 |
| NO. 118 | BL0180 | 241289 | 243097 | + | probable permease protein of abc transporter | trembl|U50951|TT50951_4 | 5.00E−151 |
| NO. 119 | BL0181 | 243354 | 245825 | + | alpha-1-arabinofuranosidase a (EC 3.2.1.55) | trembl|AL031541|SCI35_5 | 5.00E−108 |
| NO. 120 | BL0182 | 246175 | 247920 | complement | possible endo-1,5-alpha-1-arabinosidase | swiss|P42293|YXIA_BACSU | 3.00E−44 |
| NO. 121 | BL0183 | 248077 | 249672 | complement | possible endo-1,5-alpha-1-arabinosidase | swiss|P42293|YXIA_BACSU | 6.00E−62 |
| NO. 122 | BL0185 | 252035 | 253093 | + | laci-type transcriptional regulator | trembl|AE001777|AE001777_1 | 1.00E−39 |
| NO. 123 | BL0187 | 254391 | 255449 | + | exo-alpha-1-arabinofuranosidase ii | tremblnew|AP001513| AP001513_140 | 5.00E−108 |
| NO. 124 | BL0189 | 257322 | 258275 | + | sugar permease of abc transporter system | trembl|D90905|SSD905_101 | 2.00E−50 |
| NO. 125 | BL0190 | 258272 | 259198 | + | sugar permease of abc transporter system | trembl|D90910|SSD910_40 | 2.00E−48 |
| NO. 126 | BL0193 | 261151 | 262110 | + | widely conserved hypothetical protein with | trembl|AL132674|SCE87_2 | 2.00E−57 |
| NO. 127 | BL0194 | 262543 | 264753 | + | kup system potassium uptake protein (kup2) | pironly|F82623|F82623 | 2.00E−88 |
| NO. 128 | BL0203 | 275203 | 276966 | + | hypothetical protein involved in polysaccharide | trembl|AB010970|AB010970_8 | 2.00E−67 |
| NO. 129 | BL0205 | 278236 | 279192 | complement | possible glycosyltransferase | trembl|AF033015|AF033015_6 | 3.00E−88 |
| NO. 130 | BL0207 | 280941 | 282224 | complement | protein possibly involved in atp-driven | trembl|AB010970|AB010970_5 | 5.00E−102 |
| NO. 131 | BL0208 | 282226 | 283050 | complement | possible permease protein of abc transporter | trembl|AB010970|AB010970_4 | 2.00E−56 |
| NO. 132 | BL0210 | 284428 | 284820 | + | probable glycerol-3-phosphate | swissnew|P27623|TAGD_BACSU | 1.00E−44 |
| NO. 133 | BL0213 | 286135 | 288033 | complement | narrowly conserved hypothetical protein with | trembl|AL022076|MTV026_12 | 5.00E−21 |
| NO. 134 | BL0215 | 288832 | 289788 | + | possible glycosyltransferase | trembl|AF033015|AF033015_6 | 2.00E−88 |
| NO. 135 | BL0216 | 289799 | 291796 | + | narrowly conserved hypothetical protein with | trembl1|AL022076|MTV026_12 | 2.00E−95 |
| NO. 136 | BL0217 | 291894 | 293834 | complement | narrowly conserved hypothetical protein with | trembl|AL022076|MTV026_12 | 4.00E−95 |
| NO. 137 | BL0218 | 294189 | 294818 | complement | fragment of s. mutans orf7 | trembl|AB010970|AB010970_8 | 3.00E−22 |
| NO. 138 | BL0219 | 294976 | 295965 | + | probable transposase | trembl|U66426|TFU66426_1 | 1.00E−56 |
| NO. 139 | BL0220 | 295985 | 296746 | complement | istb-like protein (istB) | trembl|AB024946|AB024946_78 | 7.00E−37 |
| NO. 140 | BL0221 | 297207 | 298226 | complement | defective is21-type transposase | tremblnew|AP001520| AP001520_222 | 6.00E−57 |
| NO. 141 | BL0222 | 298311 | 300041 | complement | defective transposase | tremblnew|AP001520| AP001520_222 | 9.00E−30 |
| NO. 142 | BL0223 | 300095 | 300688 | complement | possible transposase | trembl|AF029727|AF029727_1 | 2.00E−28 |
| NO. 143 | BL0224 | 300691 | 300966 | complement | hypothetical protein with similarity to orfc of | tremblnew|AP001508| AP001508_57 | 4.00E−20 |
| NO. 144 | BL0227 | 303180 | 304085 | complement | glucose-1-phosphate thymidylyltransferase (EC | trembl|AB030032|AB030032_7 | 5.00E−108 |
| NO. 145 | BL0228 | 304176 | 305618 | complement | possible fused dtdp-4-keto-1-rhamnose reductase | trembl|D78182|MD182_5 | 9.00E−58 |
| NO. 146 | BL0229 | 305632 | 306675 | complement | dtdp-glucose 4,6-dehydratase (EC 4.2.1.46) | trembl|AF105113|AF105113_5 | 5.00E−140 |
| NO. 147 | BL0230 | 306818 | 308257 | complement | hypothetical transmembrane protein possibly | trembl|A76918|A76918_12 | 7.00E−62 |
| NO. 148 | BL0231 | 308379 | 310124 | complement | possible decarboxlyase with tpp domain + d236 | swiss|P23970|MEND_BACSU | 5.00E−24 |
| NO. 149 | BL0232 | 310151 | 310891 | complement | probable 3-oxoacyl-[acyl-carrier protein] | swiss|O67610|FABG_AQUAE | 8.00E−30 |
| NO. 150 | BL0235 | 313510 | 314451 | complement | probable glycosyltransferase (cps2F or dexB) | trembl|AF026471|AF026471_9 | 5.00E−105 |
| NO. 151 | BL0236 | 314467 | 315660 | complement | possible rhamnosyltransferase (cpsF) | tremblnew|Y17900|SSA17900_7 | 5.00E−139 |
| NO. 152 | BL0237 | 315718 | 317262 | complement | galactosyl transferase cpsd (EC 2.7.8.-) | trembl|AL121855|SCF62_7 | 2.00E−49 |
| NO. 153 | BL0239 | 317776 | 318978 | + | probable integrase/recombinase (sss or xerC) | swissnew|P55639|Y4RF_RHISN | 3.00E−20 |
| NO. 154 | BL0242 | 321079 | 321879 | complement | possible transposase | trembl|AL021246|MTV008_34 | 3.00E−28 |
| NO. 155 | BL0247 | 325735 | 326226 | complement | possible transposase or integrase | trembl|U50076|SL50076_2 | 8.00E−24 |
| NO. 156 | BL0249 | 327639 | 329360 | + | undecaprenyl-phosphate sugar phosphotransferase | trembl|AL121855|SCF62_7 | 4.00E−59 |
| NO. 157 | BL0251 | 331665 | 333182 | + | widely conserved hypothetical transport protein | tremblnew|AF188518|AF188518_1 | 3.00E−76 |

TABLE I-continued

| | Gene Name | Start | Stop | Strand | Function | Best Hit | Best Score |
|---|---|---|---|---|---|---|---|
| NO. 158 | BL0252 | 333282 | 334649 | complement | h(+)-stimulated manganese uptake system protein | swissnew|O05916|MNTH_MYCTU | 5.00E−109 |
| NO. 159 | BL0254 | 336313 | 336996 | complement | narrowly conserved hypothetical protein with | trembl|Z83018|MTCY349_23 | 7.00E−34 |
| NO. 160 | BL0255 | 337060 | 337929 | complement | dehydrogenase or reductase protein | trembl|AL034443|SC4B5_1 | 4.00E−68 |
| NO. 161 | BL0257 | 338565 | 341258 | complement | possible arabinogalactan endo-beta-galactosidase | trembl|new|AP001514|AP001514_29 | 5.00E−143 |
| NO. 162 | BL0258 | 341454 | 342509 | complement | laci-type transcriptional regulator | trembl|AE001777|AE001777_1 | 2.00E−28 |
| NO. 163 | BL0259 | 342553 | 344826 | complement | beta-galactosidase i(EC 3.2.1.23) (lactase) | trembl|AL158061|SC6D11_3 | 5.00E−171 |
| NO. 164 | BL0260 | 344872 | 345879 | complement | sugar transport system permease protein | trembl|AL158061|SC6D11_5 | 5.00E−113 |
| NO. 165 | BL0261 | 345882 | 346844 | complement | sugar transport system permease protein | trembl|AL158061|SC6D11_6 | 5.00E−100 |
| NO. 166 | BL0262 | 347063 | 348412 | complement | solute binding protein of abc transporter | trembl|AL158061|SC6D11_4 | 1.00E−90 |
| NO. 167 | BL0263 | 349108 | 349518 | + | fragment of arabinose permease | trembl|Z99121|BSUB0018_82 | 1.00E−23 |
| NO. 168 | BL0264 | 349792 | 353853 | complement | atp binding protein of abc transporter | swiss|P71355|Y663_HAEIN | 5.00E−105 |
| NO. 169 | DL0266 | 354798 | 356621 | + | probable long-chain-fatty acid coa ligase | trembl|AL049497|SC6G10_4 | 5.00E−130 |
| NO. 170 | BL0267 | 356803 | 357438 | complement | atp binding protein of abc transporter similar | trembl|AF140784|AP140784_2 | 7.00E−61 |
| NO. 171 | BL0268 | 357451 | 358674 | complement | atp binding protein of abc transporter similar | trembl|AF140784|AF140784_1 | 4.00E−35 |
| NO. 172 | BL0269 | 358671 | 360038 | complement | abc-type transporter similar to vex3 (vexp3) of | trembl|AF140784|AF140784_3 | 5.00E−67 |
| NO. 173 | BL0271 | 362037 | 362753 | + | possible amidotransferase subunit | trembl|AL031541|SC135_37 | 4.00E−26 |
| NO. 174 | BL0272 | 362937 | 364454 | complement | 1-arabionse isomerase (EC 5.3.1.4) (araA) | trembl|AB036736|AB036736_2 | 5.00E−135 |
| NO. 175 | BL0273 | 364686 | 365378 | complement | 1-ribulose-5-phosphate 4-epimerase (EC 5.1.3.4) | gp|AB038527|7242885 | 4.00E−75 |
| NO. 176 | BL0274 | 365463 | 367109 | complement | probable sugar kinase | trembl|AJ249910|PSP249910_1 | 2.00E−22 |
| NO. 177 | BL0275 | 367264 | 368418 | complement | laci-type transcriptional regulator | trembl|AL158061|SC6D11_7 | 6.00E−43 |
| NO. 178 | BL0276 | 368506 | 369345 | complement | probable ribonuclease hii (EC 3.1.26.4) (rnase | swissnew|O69989|RNH2_STRCO | 2.00E−30 |
| NO. 179 | BL0277 | 369465 | 370322 | complement | probable signal peptidase i (EC 3.4.21.89) | trembl|AL023797|SC2E1_15 | 2.00E−33 |
| NO. 180 | BL0279 | 371486 | 373186 | complement | glucose-6-phosphate isomerase (gpi) (EC 5.3.1.9) | swiss|P77895|G6PI_MYCTU | 0 |
| NO. 181 | BL0282 | 374992 | 376272 | complement | femab-like protein possibly involved in | trembl|U50357|SZU50357_1 | 5.00E−45 |
| NO. 182 | BL0283 | 376322 | 377632 | complement | femab-like protein possibly involved in | trembl|U66883|SSU66883_4 | 5.00E−41 |
| NO. 183 | BL0284 | 377706 | 378974 | complement | femab-like protein possibly involved in | trembl|U50357|SZU50357_1 | 9.00E−53 |
| NO. 184 | BL0285 | 379421 | 380179 | complement | widely conserved hypothetical protein in haml | trembl|AL096852|SCE19A_2 | 1.00E−46 |
| NO. 185 | BL0286 | 380223 | 380999 | complement | probable ribonuclease ph (EC 2.7.7.56) (rnase | trembl|AL096852|SCE19A_4 | 7.00E−82 |
| NO. 186 | BL0287 | 381282 | 382640 | complement | conserved hypothetical protein with unknown | trembl|AL096852|SCE19A_7 | 5.00E−128 |
| NO. 187 | BL0290 | 384147 | 385157 | + | possible reductase | trembl|U60828|LLU60828_1 | 5.00E−104 |
| NO. 188 | BL0291 | 385766 | 386266 | + | phosphopantetheine adenylyltransferase (EC | swiss|Q9ZBR1|COAD_STRCO | 2.00E−35 |
| NO. 189 | BL0293 | 387403 | 387882 | + | conserved hypothetical protein with duf177 | trembl|AL034447|SC7A1_14 | 2.00E−25 |
| NO. 190 | BL0295 | 388208 | 389041 | + | ribonuclease iii (EC 3.1.26.3) (rnase iii) | swiss|O69469|RNC_MYCLE | 2.00E−47 |
| NO. 191 | BL0296 | 389202 | 391169 | + | acetolactate synthase (EC 4.1.3.18) | trembl|AL035569|SC8D9_24 | 0 |
| NO. 192 | BL0297 | 391186 | 391740 | + | acetolactate synthase small subunit (EC | trembl|AF175526|AF175526_1 | 6.00E−52 |
| NO. 193 | BL0298 | 392184 | 392603 | + | plasmid stability protein stbb (stbB) | pironly|H82660|H82660 | 1.00E−20 |
| NO. 194 | BL0299 | 392656 | 394932 | complement | atp binding protein of abc transporter | trembl|AL022002|MTV047_2 | 2.00E−95 |
| NO. 195 | BL0300 | 394980 | 395870 | complement | possible amidotransferase | trembl|D64006|SSSLLLH_57 | 5.00E−25 |
| NO. 196 | BL0301 | 395927 | 397567 | + | cysteinyl-trna synthetase 1 (EC 6.1.1.16) | gp|AL160331|7242756 | 5.00E−115 |
| NO. 197 | BL0303 | 398703 | 400451 | + | signal recognition particle protein (ffh) | trembl|AL023797|SC2E1_3 | 5.00E−170 |
| NO. 198 | BL0305 | 401870 | 402331 | + | 30s ribosomal protein s16 (rpsP) | swiss|Q10795|RS16_MYCTU | 1.00E−28 |
| NO. 199 | BL0307 | 402608 | 403231 | + | possible rim-like protein involved in efficient | trembl|AL023797|SC2E1_10 | 6.00E−22 |

TABLE I-continued

| | Gene Name | Start | Stop | Strand | Function | Best Hit | Best Score |
|---|---|---|---|---|---|---|---|
| NO. 200 | BL0308 | 403354 | 404406 | complement | inosine-uridine preferring nucleoside hydrolase | trembl\|AE001900\|AE001900_5 | 2.00E−40 |
| NO. 201 | BL0309 | 404504 | 405367 | complement | possible oxidoreductase of the aldo/keto | trembl\|AE002028\|AE002028_7 | 2.00E−32 |
| NO. 202 | BL0311 | 407767 | 408345 | complement | lema-like protein (lemA) | trembl\|U66186\|LMU66186_1 | 3.00E−39 |
| NO. 203 | BL0312 | 408640 | 409419 | complement | probable atp-binding protein of abc transporter | gp\|AL353816\|7636012 | 5.00E−101 |
| NO. 204 | BL0313 | 409472 | 410437 | complement | probable phosphate binding-protein of abc | gp\|AL353816\|7636013 | 2.00E−67 |
| NO. 205 | BL0314 | 410470 | 411423 | complement | probable phosphate permease protein of abc | gp\|AL353816\|7636014 | 1.00E−75 |
| NO. 206 | BL0315 | 411634 | 412767 | complement | phosphate-binding transport protein of abc | gp\|AL353816\|7636015 | 4.00E−64 |
| NO. 207 | BL0316 | 413007 | 413777 | complement | response regulator of two-component system | tremblnew\|AF123314\|AF123314_2 | 2.00E−77 |
| NO. 208 | BL0317 | 413910 | 415241 | complement | histidine kinase sensor of two-component system | gp\|AL160331\|7242750 | 7.00E−64 |
| NO. 209 | BL0318 | 415492 | 416205 | complement | probable mta/sah nucleosidase [includes: | tremblnew\|AP001518\|AP001518_69 | 2.00E−29 |
| NO. 210 | BL0319 | 416327 | 417559 | complement | phospho-2-keto-3-deoxyheptonate aldolase (dahp | swiss\|P00886\|AROG_ECOLI | 4.00E−97 |
| NO. 211 | BL0320 | 417688 | 418821 | complement | phospho-2-debydro-3-deoxyheptonate aldolase, | pironly\|H82856\|H82856 | 5.00E−101 |
| NO. 212 | BL0321 | 419113 | 420456 | complement | aminopeptidase c (EC 3.4.22.-) (pepC) | swiss\|Q48543\|PEPC_LACDL | 3.00E−88 |
| NO. 213 | BL0323 | 422296 | 422973 | complement | pyrrolidone–carboxylate peptidase (EC 3.4.19.3) | swiss\|P28618\|PCP_BACSU | 4.00E−26 |
| NO. 214 | BL0324 | 422983 | 423858 | complement | probable | trembl\|Z37516\|HIACAPIID_1 | 1.00E−31 |
| NO. 215 | BL0325 | 423938 | 424918 | complement | conserved hypothetical protein with unknown | swissnew\|P45497\|YFTZ_STRCO | 2.00E−33 |
| NO. 216 | BL0326 | 424996 | 426717 | complement | possible protease or peptidase | tremblnew\|AP001511\|AP001511_163 | 2.00E−65 |
| NO. 217 | BL0327 | 426776 | 427531 | + | trna (guasine-nl)-methyltransferase (EC | swiss\|O69882\|TRMD_STRCO | 5.00E−60 |
| NO. 218 | BL0328 | 427555 | 428175 | complement | hypothetical protein with possible methylase | trembl\|Z83018\|MTCY349_17 | 1.00E−26 |
| NO. 219 | BL0329 | 428393 | 431236 | complement | atp-dependent dna helicase (EC 3.6.1.-). | trembl\|AL034447\|SC7A1_10 | 5.00E−104 |
| NO. 220 | BL0332 | 433138 | 434415 | + | narrowly conserved hypothetical protein with | swiss\|P42306\|YXIO_BACSU | 2.00E−93 |
| NO. 221 | BL0335 | 435958 | 436491 | + | methylated-dna-protein-cysteine | trembl\|AL034446\|SC1A9_15 | 4.00E−24 |
| NO. 222 | BL0338 | 439120 | 440592 | + | aspartate ammonia-lyase (EC 4.3.1.1) (aspartase) | tremblnew\|AE008304\|AE008304_2 | 1.00E−123 |
| NO. 223 | BL0341 | 442847 | 444124 | complement | atp binding protein of abc transporter (msiK) | trembl\|ALO31225\|SC8B7_10 | 6.00E−66 |
| NO. 224 | BL0343 | 444980 | 445930 | complement | possible permease protein of abc transporter | trembl\|AL139076\|CJ11168X3_S9 | 7.00E−33 |
| NO. 225 | BL0344 | 445942 | 447108 | complement | possible solute binding protein of abc | pironly\|D83240\|D83240 | 2.00E−34 |
| NO. 226 | BL0345 | 447361 | 448647 | complement | d-alanine-d-alanine ligase (EC 6.3.2.4) | swiss\|P95114\|DDL_MYCTU | 2.00E−76 |
| NO. 227 | BL0346 | 448735 | 449736 | complement | glycerol-3-phosphate dehydrogenase [nad(p)+] (EC | trembl\|AL034447\|SC7A1_3 | 5.00E−79 |
| NO. 228 | BL0348 | 450878 | 451267 | complement | hypothetical 14.5 kda translational inhibitor | swiss\|O58584\|Y854_PYRHO | 7.00E−25 |
| NO. 229 | BL0350 | 452516 | 453526 | complement | hypothetical protein with marginal similarity to | trembl\|AL137242\|SC8F4_23 | 8.00E−33 |
| NO. 230 | BL0354 | 455906 | 456895 | + | possible secreted peptidyl-prolyl cia-trans is | trembl\|AL132648\|SCI41_22 | 5.00E−25 |
| NO. 231 | BL0355 | 456941 | 457750 | complement | narrowly conserved hypothetical protein with | swiss\|Q10634\|YD21_MYCTU | 1.00E−60 |
| NO. 232 | BL0357 | 458092 | 459564 | complement | atp synthase beta chain (EC 3.6.1.34) (atpD) | trembl\|Z22606\|SLATPSYNA_8 | 0 |
| NO. 233 | BL0358 | 459573 | 460496 | complement | atp synthase gamma chain (EC 3.6.1.34) (atpG) | trembl\|Z22606\|SLATPSYNA_7 | 1.00E−60 |
| NO. 234 | BL0359 | 460500 | 462131 | complement | atp synthase alpha chain (EC 3.6.1.34) (atpA) | trembl\|Z22606\|SLATPSYNA_6 | 0 |
| NO. 235 | BL0360 | 462207 | 463043 | complement | atp synthase delta chain (EC 3.6.1.34) (atpH) | swissnew\|Q10594\|ATPD_MYCTU | 2.00E−21 |
| NO. 236 | BL0363 | 463984 | 464796 | complement | atp synthase a chain (EC 3.6.1.34) (atpB) | swiss\|P50012\|ATP6_STRLI | 9.00E−28 |
| NO. 237 | BL0365 | 465258 | 466292 | complement | homoserine o-succinyltransferase (EC 2.3.1.46) | swissnew\|Q9KAK7\|META_BACHD | 2.00E−88 |
| NO. 238 | BL0375 | 472472 | 473593 | + | hypothetical protein with similarity to gp 34 | trembl\|AJ006589\|BPH6589_4 | 3.00E−25 |

TABLE I-continued

| | Gene Name | Start | Stop | Strand | Function | Best Hit | Best Score |
|---|---|---|---|---|---|---|---|
| NO. 239 | BL0381 | 477134 | 479185 | + | phage related protein: putative minor tail | trembl|AF011378|AF011378_14 | 1.00E-34 |
| NO. 240 | BL0386 | 483079 | 483909 | complement | probable phage-family integrase/recombinase | trembl|Z80225|MTCY441_16 | 2.00E-47 |
| NO. 241 | BL0388 | 486597 | 488837 | + | possible glycanase or glycogenase with amylase | trembl|AL138978|SC6A11_19 | 5.00E-174 |
| NO. 242 | BL0389 | 489065 | 489559 | + | inorganic pyrophosphatase (EC 3.6.1.1) | swiss|Q9X8I9|IPYR_STRCO | 6.00E-51 |
| NO. 243 | BL0390 | 489793 | 490377 | + | integral membrane protein in the upf0059 | trembl|AL139074|CJ11168X1_155 | 2.00E-36 |
| NO. 244 | BL0392 | 491351 | 492151 | + | possible transcriptional requlatory protein with | swissnew|Q05943|GLNR_STRCO | 7.00E-69 |
| NO. 245 | BL0393 | 492210 | 492896 | + | endonuclease iii (EC 4.2.99.18) (dna-(apurinic | swiss|O69642|END3_MYCTU | 7.00E-58 |
| NO. 246 | BL0395 | 494523 | 497363 | + | valyl-trna synthetase (EC 6.1.1.9) (valine-trna | Swiss|Q9ZCN6|SYV_RICPR | 5.00E-155 |
| NO. 247 | BL0398 | 500447 | 502516 | complement | transcription termination factor rho (rho) | trembl|L27277|MLRHO_1 | 5.00E-151 |
| NO. 248 | BL0399 | 502722 | 504335 | complement | hypothetical protein with pyridine | trembl|AP000002|AP000002_120 | 1.00E-29 |
| NO. 249 | BL0400a | 506584 | 507216 | + | narrowly conserved hypothetical protein with | trembl|Z97369|MLCB250_15 | 2.00E-34 |
| NO. 250 | BL0402 | 508266 | 509765 | complement | glutamyl-trna(gln) amidotransferase subunit b | swiss|Q9Z578|GATB_STRCO | 5.00E-176 |
| NO. 251 | BL0403 | 509791 | 511332 | complement | glutamyl-trna(gln) amidotransferase subunit a | swiss|Q9Z580|GATA_STRCO | 5.00E-164 |
| NO. 252 | BL0405 | 511802 | 512650 | complement | narrowly conserved hypothetical protein with | trembl|AL021931|MTV036_15 | 6.00E-46 |
| NO. 253 | BL0407 | 513370 | 514773 | complement | conserved hypothetical protein withduf195 | trembl|AF213822|AF213822_7 | 2.00E-53 |
| NO. 254 | BL0408 | 514837 | 515118 | complement | narrowly conserved hypothetical protein with | trembl|Z97050|MTC128_29 | 1.00E-28 |
| NO. 255 | BL0409 | 515230 | 517938 | + | copper-transporting atpase (EC 3.6.1.36) (silP) | trembl|AF067954|AF067954_9 | 5.00E-76 |
| NO. 256 | BL0410 | 518022 | 518756 | complement | glycerol uptake facilitator-like protein in mip | swiss|Q9X1E3|GLPF_THEMA | 2.00E-61 |
| NO. 257 | BL0411 | 518990 | 520669 | complement | phosphoenolpyruvate-protein phosphotransferase | tremblnew|AP001517|AP001517_195 | 5.00E-133 |
| NO. 258 | BL0413 | 521316 | 521762 | complement | 50s ribosomal protein 19 (rpll) | swiss|Q9X8U5|RL9_STRCO | 1.00E-21 |
| NO. 259 | BL0414 | 521782 | 522030 | complement | 30s ribosomal protein s18-2 (rpsR) | swiss|Q9X8K4|R18B_STRCO | 3.00E-21 |
| NO. 260 | BL0415 | 522091 | 522747 | complement | single-strand binding protein(ssb) | swiss|P71711|SSB_MYCTU | 4.00E-38 |
| NO. 261 | BL0416 | 522804 | 523097 | complement | 30s ribosomal protein s6. (rpsF) | swiss|P71710|RS6_MYCTU | 1.00E-21 |
| NO. 262 | BL0418 | 523863 | 524876 | + | ribose-phosphate pyrophosphokinase (EC 2.7.6.1) | trembl|Z92539|MTCY10G2_4 | 5.00E-103 |
| NO. 263 | BL0419 | 524952 | 525836 | complement | hypothetical protein in upf0001 | pironly|H82646|H82646 | 7.00E-30 |
| NO. 264 | BL0420 | 525916 | 529632 | complement | probable extracellular protein possibly involved | trembl|Z99113|BSUB0010_109 | 1.00E-24 |
| NO. 265 | BL0421 | 529737 | 535562 | complement | narrowly conserved hypothetical protein possibly | trembl|AJ223998|AOPCZA361_10 | 0 |
| NO. 266 | BL0422 | 536261 | 538231 | complement | narrowly conserved hypothetical protein with | tremblnew|AE005584|AE005584_8 | 5.00E-133 |
| NO. 267 | BL0423 | 538240 | 539058 | complement | sugar permease of abc transporter system | trembl|AJ223998|AOPCZA361_25 | 1.00E-38 |
| NO. 268 | BL0424 | 539079 | 540005 | complement | sugar permease of abc transporter system | trembl|AL049661|SCE134_5 | 8.00E-38 |
| NO. 269 | BL0425 | 540293 | 541618 | complement | solute binding protein of abc transporter | trembl|AL138851|SCE59_5 | 2.00E-20 |
| NO. 270 | BL0426 | 542104 | 543126 | + | lacti-type transcriptional regulator | swiss|O87590|CELR_THEFU | 3.00E-40 |
| NO. 271 | BL0427 | 543141 | 544646 | complement | hypothetical protein kinaase in abc1 family | swiss|Q46189|YHGI_CLOPA | 2.00E-78 |
| NO. 272 | BL0429 | 545394 | 546146 | complement | possible cobyric acid synthase cobq | trembl|AF080002|AF080002_2 | 3.00E-47 |
| NO. 273 | BL0430 | 546249 | 547721 | complement | narrowly conserved hypothetical protein with mur | trembl|D90914|SSD914_7 | 9.00E-48 |
| NO. 274 | BL0431 | 547721 | 549250 | complement | replicative dna helicase (EC 3.6.1.-) (dnaB) | trembl|AL049826|SCH24_33 | 5.00E-145 |
| NO. 275 | BL0432 | 549306 | 550901 | + | hypothetical protein in upf0013 | trembl|AL049826|SCH24_32 | 3.00E-62 |
| NO. 276 | BL0433 | 550935 | 552761 | complement | protein-pii; uridylyltransferase (EC 2.7.7.59) | swiss|O69873|GLND_STRCO | 1.00E-90 |
| NO. 277 | BL0434 | 552869 | 553207 | complement | nitrogen regulatory protein p-ii. (glnB) | pironly|T35668|T35668 | 4.00E-43 |
| NO. 278 | BL0435 | 553209 | 554504 | complement | possible ammonium ion transporter (amtP) | trembl|AJ010319|CAJ10319_2 | 5.00E-124 |
| NO. 279 | BL0436 | 554872 | 556134 | complement | ftsy signal recognition particle (docking | trembl|AJ034447|SC7A1_24 | 5.00E-102 |

TABLE I-continued

| | Gene Name | Start | Stop | Strand | Function | Best Hit | Best Score |
|---|---|---|---|---|---|---|---|
| NO. 280 | BL0437 | 556239 | 557078 | + | probable tetr-type transcriptional regulator | trembl|Z92539|MTCY10G2__6 | 9.00E−51 |
| NO. 281 | BL0438 | 557102 | 558136 | + | probable glycosyltransferase | trembl|AJ006986|SPAJ6986__9 | 1.00E−26 |
| NO. 282 | BL0439 | 558210 | 559898 | complement | dipeptidase (pepD) | trembl|Z38063|LHDIPEP__1 | 8.00E−97 |
| NO. 283 | BL0440 | 560039 | 561706 | + | glucose-6-phosphate 1-dehydrogenase (EC | trembl|AL096839|SCC22__19 | 0 |
| NO. 284 | BL0441 | 561703 | 562728 | + | narrowly conserved hypothetical protein with | trembl|AL031107|SC5A7__10 | 1.00E−57 |
| NO. 285 | BL0443 | 562865 | 563797 | + | probable 6-phosphogluconolactonase (EC 3.1.1.31) | swiss|Q9XAB7|6PGL__STRCO | 1.00E−37 |
| NO. 286 | BL0444 | 564101 | 565555 | complement | 6-phosphogluconate dehydrogenase, | trembl|Z83859|MTCY359__7 | 5.00E−167 |
| NO. 287 | BL0446 | 567375 | 570005 | + | hypothetical membrane protein with similarity to | pironly|A48653|A48653 | 9.00E−34 |
| NO. 288 | BL0447 | 570002 | 572164 | + | hypothetical membrane protein with similarity to | trembl|AE000938|AE000938__8 | 3.00E−56 |
| NO. 289 | BL0450 | 573563 | 574360 | complement | atp binding protein of abc transporter | trembl|AL139079|CJ11168X6__108 | 2.00E−65 |
| NO. 290 | BL0451 | 574376 | 575599 | complement | possible permease protein of abc transporter | trembl|AL139079|CJ11168X6__107 | 3.00E−20 |
| NO. 291 | BL0452 | 575633 | 576937 | complement | possible permease protein of abc transporter | trembl|AL139079|CJ11168X6__106 | 3.00E−48 |
| NO. 292 | BL0454 | 578386 | 579069 | complement | narrowly conserved hypothetical protein | swiss|P19478|TA34__TREPA | 7.00E−36 |
| NO. 293 | BL0455 | 579244 | 581055 | complement | widely conserved hypothetical membrane protein | trembl|AE001265|AE001265__1 | 3.00E−55 |
| NO. 294 | BL0457 | 582190 | 582831 | complement | narrowly conserved hypothetical protein with | trembl|Z99122|BSUB0019__159 | 1.00E−38 |
| NO. 295 | BL0458 | 582999 | 583358 | + | narrowly conserved hypothetical protein with | trembl|AL139079|CJ11168X6__4 | 5.00E−29 |
| NO. 296 | BL0460 | 584343 | 585326 | + | probable lysr-type transcriptional regulator | swiss|P39592|YWBI__BACSU | 4.00E−21 |
| NO. 297 | BL0461 | 585539 | 586423 | complement | is3-type transposase | trembl|new|AE000433|ECAE433__4 | 1.00E−46 |
| NO. 298 | BL0464 | 587533 | 593433 | complement | narrowly conserved hypothetical protein with | trembl|AL031155|SC3A7__16 | 5.00E−144 |
| NO. 299 | BL0465 | 593602 | 594786 | + | transpsosase in is256 family | swiss|Q52873|TRA5__RHIME | 5.00E−61 |
| NO. 300 | BL0469 | 596683 | 598203 | complement | glutamyl-trna synthetase (EC 6.1.1.17) | swiss|O33120|SYE__MYCLE | 5.00E−163 |
| NO. 301 | BL0472 | 600060 | 600977 | complement | widely conserved hypothetical protein with | pironly|G82131|G82131 | 5.00E−30 |
| NO. 302 | BL0474 | 602113 | 602772 | complement | hypothetical protein with possible | trembl|new|AL392176|SCD65__13 | 2.00E−36 |
| NO. 303 | BL0475 | 603034 | 604479 | + | hypothetical membrane protein with unknown | trembl|AL009204|SC9B10__25 | 3.00E−32 |
| NO. 304 | BL0478 | 606009 | 607526 | complement | formate-tetrahydrofolate ligase (EC 6.3.4.3) | trembl|new|AL162753|NMA2Z2491__232 | 3.00E−47 |
| NO. 305 | BL0479 | 607686 | 609287 | complement | dipeptidase (pepD) | trembl|Z38063|LHDIPEP__1 | 5.00E−105 |
| NO. 306 | BL0481 | 610303 | 611805 | + | is21-type transposase | trembl|new|AP001520|AP001520__222 | 4.00E−52 |
| NO. 307 | BL0482 | 611886 | 612587 | + | istb-like protein | trembl|new|AJ414141|AJ414141__30 | 1.00E−32 |
| NO. 308 | BL0483 | 612690 | 613850 | complement | possible dna polymerase iii delta prime | trembl|AL035636|SCH5__3 | 6.00E−57 |
| NO. 309 | BL0484 | 613847 | 614428 | complement | thymidylate kinase (EC 2.7.4.9) (dtmp kinase) | trembl|AL035636|SCH5__5 | 9.00E−47 |
| NO. 310 | BL0485 | 614745 | 617837 | complement | dna topoisomerase i (EC 5.99.1.2) (relaxing | swiss|Q9X909|TOP1__STRCO | 0 |
| NO. 311 | BL0487 | 619475 | 621889 | + | probable penicillin-binding protein | gp|AL353832|7636001 | 7.00E−84 |
| NO. 312 | BL0488 | 621961 | 623877 | complement | 2-isopropylmalate synthase (EC 4.1.3.12) (leuA) | swiss|P96420|LEU1__MYCTU | 0 |
| NO. 313 | BL0491 | 626149 | 626862 | complement | hypothetical protein with unknown function | gp|AL353815|7635958 | 1.00E−20 |
| NO. 314 | BL0492 | 626937 | 628031 | + | aspartate-semialdehyde dehydrogenase (EC | swissnew|P41394|DHAS__LEPIN | 3.00E−71 |
| NO. 315 | BL0493 | 628113 | 628655 | complement | aspartokinase (EC 2.7.2.4) (aspartokinase beta | trembl|AL079348|SC66T3__26 | 3.00E−44 |
| NO. 316 | BL0494 | 628735 | 629499 | complement | aspartokinase (EC 2.7.2.4) (aspartokinase alpha | swissnew|P41403|AK__MYCSM | 2.00E−86 |
| NO. 317 | BL0495 | 629860 | 631143 | complement | narrowly conserved hypothetical protein with | trembl|Z97182|MTCY19H5__12 | 9.00E−21 |
| NO. 318 | BL0498 | 632032 | 633165 | + | possible sortase-like protein | trembl|AF019629|AF019629__2 | 3.00E−45 |
| NO. 319 | BL0499 | 633162 | 633764 | complement | recombination protein recr (recR) | swissnew|Q9XAI4|RECR__STRCO | 4.00E−70 |
| NO. 320 | BL0500 | 633790 | 636702 | complement | dna polymerase iii subunit gamma/tau (EC | trembl|AL118514|SCD25__3 | 5.00E−123 |
| NO. 321 | BL0502 | 637695 | 638825 | complement | narrowly conserved hypothetical protein with | trembl|AL021925|MTV022__2 | 5.00E−23 |

TABLE I-continued

| | Gene Name | Start | Stop | Strand | Function | Best Hit | Best Score |
|---|---|---|---|---|---|---|---|
| NO. 322 | BL0508 | 641511 | 642578 | complement | hypothetical protein possibly involved in | trembl|AL035636|SCH5_19 | 9.00E−56 |
| NO. 323 | BL0510 | 643758 | 644483 | complement | deda integral membrane protein (dsg-1 protein) | swissnew|P09548|DEDA_ECOLI | 2.00E−37 |
| NO. 324 | BL0512 | 645418 | 646221 | complement | 3-oxoacyl-[acyl-carrier protein] reductase (EC | tremblnew|AP001515|AP001515_225 | 1.00E−44 |
| NO. 325 | BL0515 | 648919 | 650271 | complement | hypothetical transmembrane protein in | trembl|AE001862|AE001862_175 | 4.00E−58 |
| NO. 326 | BL0516 | 650544 | 651131 | complement | probable merr-type-transcriptional regulator | swissnew|P40183|HSPR_STRCO | 7.00E−20 |
| NO. 327 | BL0517 | 651146 | 652165 | complement | chaperone protein dnaj. (dnaJ) | trembl|AB009842|AB009842_3 | 4.00E−40 |
| NO. 328 | BL0519 | 652397 | 653056 | complement | grpe protein (hsp-70 cofactor) (grpE) | swissnew|Q05562|GRPE_STRCO | 1.00E−27 |
| NO. 329 | BL0520 | 653053 | 654933 | complement | dnak protein (heat shock protein 70) (hsp70) | swiss|Q05558|DNAK_STRCO | 0 |
| NO. 330 | BL0523 | 655916 | 657997 | complement | possible xylosidase or glucosidase | tremblnew|AL512980|SSOLP2N19_30 | 1.00E−41 |
| NO. 331 | BL0524 | 658565 | 659281 | complement | possible permease protein of abc transporter | trembl|AL009199|SC7B7_4 | 5.00E−21 |
| NO. 332 | BL0525 | 659551 | 660561 | + | probable laci-type transcriptional regulator | trembl|AL136502|SCF43_17 | 7.00E−31 |
| NO. 333 | BL0527 | 661816 | 664053 | + | 4-alpha-glucanotransferase (EC 2.4.1.25) | swiss|O53932|MALQ_MYCTU | 5.00E−158 |
| NO. 334 | BL0528 | 664185 | 665219 | + | probable laci-type transcriptional regulator | trembl|AL121596|SC51A_33 | 1.00E−28 |
| NO. 335 | BL0529 | 665379 | 667193 | + | probable alpha-1,4-glucosidase (EC 3.2.1.10); | trembl|AF105219|AP105219_2 | 5.00E−143 |
| NO. 336 | BL0530 | 667273 | 668334 | complement | ketol-acid reductoisomerase (EC 1.1.1.86) | swiss|Q9Z565|ILVC_STRCO | 5.00E−106 |
| NO. 337 | BL0531 | 668754 | 669806 | complement | ketol-acid reductoisomerase (EC 1.1.1.86) | swiss|Q9Z565|ILVC_STRCO | 5.00E−109 |
| NO. 338 | BL0532 | 670003 | 671523 | complement | transmembrane transport protein possibly for | tremblnew|AE005578|AE005578_1 | 5.00E−118 |
| NO. 339 | BL0533 | 671998 | 673041 | complement | laci-type transcriptional regulator (scrR) | swiss|Q54430|SCRR_STRMU | 1.00E−39 |
| NO. 340 | BL0536 | 674947 | 676473 | complement | sucrose phosphorylase (EC 2.4.1.7) (sucrose | trembl|AF065245|AF065245_3 | 5.00E−149 |
| NO. 341 | BL0537 | 676808 | 677857 | + | truncated transposase | trembl|AP000342|AP000342_11 | 1.00E−51 |
| NO. 342 | BL0538 | 677944 | 678999 | complement | probable integrase/recombinase | swissnew|P55636|Y4RC_RHISN | 9.00E−20 |
| NO. 343 | BL0540 | 679958 | 681160 | complement | possible integrase/recombinase | swissnew|P55639|Y4RF_RHISN | 3.00E−20 |
| NO. 344 | BL0543 | 682749 | 683783 | complement | laci-type transcriptional regulator | tremblnew|AP001514|AP001514_225 | 1.00E−35 |
| NO. 345 | BL0544 | 683955 | 685754 | complement | alpha-1-arabinofuranosidase a (EC 3.2.1.55) | gp|AL163003|7414545 | 5.00E−161 |
| NO. 346 | BL0545 | 685919 | 687712 | complement | possible low-affinity potassium uptake system | pironly|C83530|C83530 | 2.00E−65 |
| NO. 347 | BL0546 | 687912 | 688997 | complement | laci-type transcriptional regulator | swiss|Q54430|SCRR_STRMU | 7.00E−37 |
| NO. 348 | BL0548 | 690945 | 692528 | complement | probable voltage gated channel protein | pironly|C82449|C82449 | 2.00E−50 |
| NO. 349 | BL0549 | 692552 | 693838 | complement | adenylosuccinate synthetase (EC 6.3.4.4) | swiss|Q9X8P6|PURA_STRCO | 5.00E−176 |
| NO. 350 | BL0550 | 694054 | 695121 | + | fructose-bisphosphate aldolase (EC 4.1.2.13) | swiss|O06313|ALF_MYCTU | 5.00E−119 |
| NO. 351 | BL0551 | 695332 | 696252 | complement | possible protease htpx (EC 3.4.24.-) (htpX) | swiss|O06429|HTPX_MYCTU | 1.00E−69 |
| NO. 352 | BL0552 | 696445 | 697896 | complement | probable ferredoxin/ferredoxin-nadp reductase ( | trembl|AL132856|SCF15_2 | 5.00E−111 |
| NO. 353 | BL0553 | 698027 | 698869 | + | conserved hypothetical protein with unknown | trembl|Z97182|MTCY19H5_12 | 5.00E−22 |
| NO. 354 | BL0554 | 699209 | 701368 | complement | probable cation-transporting atpase v (EC | trembl|AL109962|SCJ1_13 | 4.00E−83 |
| NO. 355 | BL0555 | 701780 | 703807 | complement | possible do serine protease (EC 3.4.21.-) (degP | trembl|AE001732|AB001732_1 | 5.00E−51 |
| NO. 356 | BL0556 | 704224 | 705537 | + | queuine trna-ribosyltransferase (EC 2.4.2.29) | swiss|O32053|TGT_BACSU | 8.00E−84 |
| NO. 357 | BL0560 | 706974 | 707657 | + | hypothetical transmembrane protein with unknown | trembl|AB003158|AB003158_1 | 7.00E−28 |
| NO. 358 | BL0562 | 708341 | 708673 | complement | widely conserved hypothetical protein with | pironly|G82395|G82395 | 3.00E−28 |
| NO. 359 | BL0563 | 708789 | 710270 | + | probable type ii restriction enzyme similar to | trembl|AF051563|AF051563_1 | 1.00E−37 |
| NO. 360 | BL0564 | 710277 | 711548 | complement | modification methylase sau3ai (EC 2.1.1.73) | trembl|AF051563|AF051563_3 | 1.00E−74 |

TABLE I-continued

| | Gene Name | Start | Stop | Strand | Function | Best Hit | Best Score |
|---|---|---|---|---|---|---|---|
| NO. 361 | BL0568 | 714565 | 715548 | complement | peptide methionine sulfoxide reductase. (msrA) | tremblnew|AL162752|NMA1Z2491_273 | 1.00E−86 |
| NO. 362 | BL0570 | 716076 | 718649 | complement | hypothetical protein with unknown function | swissnew|P94974|SYK2_MYCTU | 1.00E−23 |
| NO. 363 | BL0575 | 720885 | 721994 | complement | narrowly conserved hypothetical protein with | tremblnew|AE005358|AE005358_4 | 4.00E−58 |
| NO. 364 | BL0577 | 723052 | 723771 | complement | tela-like protein associated with cryptic | swiss|P37535|YAAN_BACSU | 3.00E−40 |
| NO. 365 | BL0582 | 727987 | 730431 | + | probable dipeptidyl peptidase iv | trembl|D83263|SMD263_1 | 1.00E−56 |
| NO. 366 | BL0583 | 730616 | 731317 | + | hypothetical protein with fha domain | trembl|AL079308|SCH69_13 | 8.00E−23 |
| NO. 367 | BL0584 | 731347 | 731877 | + | hypothetical protein with fha domain | trembl|AL079308|SCH69_14 | 6.00E−33 |
| NO. 368 | BL0585 | 731882 | 733576 | + | possible phosphoprotein phosphatase | trembl|AL079308|SCH69_15 | 1.00E−61 |
| NO. 369 | BL0586 | 733573 | 735132 | + | protein involved in cell wall formation and | trembl|AL079308|SCH69_16 | 5.00E−103 |
| NO. 370 | BL0587 | 735129 | 736595 | + | probable penicillin binding protein | trembl|Z80233|MTCY10H4_14 | 1.00E−80 |
| NO. 371 | BL0588 | 736592 | 737542 | + | probable serine-threonine protein kinase (pknA) | swiss|P71585|PKNA_MYCTU | 5.00E−59 |
| NO. 372 | BL0589 | 737539 | 739611 | + | probable serine/threonine-protein kinase pknb | trembl|AL079308|SCH69_18 | 5.00E−106 |
| NO. 373 | BL0590 | 739837 | 740481 | complement | para-aminobenzoate synthase glutamine | trembl|AL079308|SCH69_21 | 8.00E−62 |
| NO. 374 | BL0591 | 740532 | 741770 | complement | hypothetical transmembrane protein with unknown | trembl|AL079308|SCH69_19 | 1.00E−26 |
| NO. 375 | BL0592 | 741767 | 742567 | complement | narrowly conserved hypothetical protein with | trembl|AL079308|SCH69_23 | 6.00E−30 |
| NO. 376 | BL0594 | 743795 | 744640 | complement | conserved membrane protein in rhomboid family | trembl|AL021926|MTV031_3 | 9.00E−24 |
| NO. 377 | BL0597 | 745313 | 747838 | complement | glycogen phosphorylase (EC 2.4.1.1) (glgP) | trembl|D90907|SSD907_48 | 0 |
| NO. 378 | BL0600 | 749019 | 750110 | + | tryptophanyl-trna synthetase (EC 6.1.1.2) | trembl|AE001959|AE001959_7 | 1.00E−58 |
| NO. 379 | BL0601 | 750288 | 752075 | complement | widely conserved hypothetical protein with | trembl|AE002083|AE002083_5 | 6.00E−36 |
| NO. 380 | BL0602 | 752125 | 753765 | complement | possible sodium/proline symporter (opuE) | swiss|O06493|OPUE_BACSU | 5.00E−104 |
| NO. 381 | BL0604 | 756164 | 758917 | + | phosphoenolpyruvate carboxylase (EC 4.1.1.31) | swiss|P28594|CAPP_ANASP | 5.00E−110 |
| NO. 382 | BL0609 | 762024 | 763673 | complement | hypothetical protein possibly related to | trembl|AE002053|AE002053_3 | 3.00E−34 |
| NO. 383 | BL0610 | 763888 | 764895 | complement | laci-type transcriptional regulator | trembl|AE001777|AE001777_1 | 6.00E−24 |
| NO. 384 | BL0613 | 765441 | 766727 | + | probable integral membrane transporter | tremblnew|AP001515|AP001515_262 | 1.00E−68 |
| NO. 385 | BL0614 | 766844 | 768760 | complement | thioredoxin reductase (EC 1.6.4.5) (trxB) | pironly|D35156|D35156 | 2.00E−75 |
| NO. 386 | BL0615 | 768929 | 769492 | complement | alkyl hydroperoxide reductase c22 protein (EC | trembl|AF016233|AF016233_2 | 9.00E−66 |
| NO. 387 | BL0616 | 769698 | 770381 | + | probablecarbonic anhydrase (EC 4.2.1.1) (icfA) | trembl|AL022075|MTV024_6 | 1.00E−36 |
| NO. 388 | BL0617 | 770719 | 771984 | + | widely conserved hypothetical protein with duf21 | swiss|P74409|Y260_SYNY3 | 2.00E−55 |
| NO. 389 | BL0618 | 772081 | 772560 | + | hypothetical protein in dps family | trembl|AF068267|AF068267_1 | 4.00E−30 |
| NO. 390 | BL0620 | 774367 | 774732 | complement | probable gluconokinase (EC 2.7.1.12) (gluconate | trembl|AE002030|AE002030_3 | 1.00E−25 |
| NO. 391 | BL0622 | 775637 | 776743 | + | conserved hypothetical protein with unknown | swiss|P44099|YA38_HAEIN | 1.00E−38 |
| NO. 392 | BL0628 | 779817 | 781151 | complement | aspartate aminotransferase (EC 2.6.1.1) | tremblnew|AP001518|AP001518_181 | 7.00E−68 |
| NO. 393 | BL0629 | 781357 | 781791 | + | asnc-type transcriptional regulator | trembl|Z92771|MTCY71_31 | 1.00E−32 |
| NO. 394 | BL0630 | 782110 | 783456 | + | nadp-specific glutamate dehydrogenase (EC | tremblnew|AP001514|AP001514_107 | 5.00E−162 |
| NO. 395 | BL0631 | 783833 | 785254 | complement | hypothetical protein with unknown function | trembl|AP000004|AP000004_110 | 3.00E−67 |
| NO. 396 | BL0634 | 786722 | 789373 | complement | dna gyrase subunit a (EC 5.99.1.3) (gyrA) | swiss|P35885|GYRA_STRCO | 0 |
| NO. 397 | BL0635 | 789441 | 791531 | complement | dna gyrase subunit b, novobiocin-sensitive (EC | swiss|P50075|GYBS_STRSH | 0 |
| NO. 398 | BL0637 | 792179 | 793366 | complement | recombination protein recf (recF) | swissnew|P36176|RECF_STRCO | 7.00E−60 |
| NO. 399 | BL0638 | 793445 | 794569 | complement | dna polymerase iii, beta chain (EC 2.7.7.7) | swissnew|P27903|DP3B_STRCO | 2.00E−88 |
| NO. 400 | BL0640 | 795305 | 796807 | complement | chromosomal replication initiator protein dnaa. | trembl|AF222789|AF222789_7 | 5.00E−103 |

TABLE I-continued

| | Gene Name | Start | Stop | Strand | Function | Best Hit | Best Score |
|---|---|---|---|---|---|---|---|
| NO. 401 | BL0644 | 797963 | 798970 | + | conserved hypothetical transmembrane protein in | trembl|AF031590|AF031590_7 | 6.00E−37 |
| NO. 402 | BL0645 | 799094 | 799627 | + | narrowly conserved hypothetical protein with | trembl|AF031590|AF031590_6 | 2.00E−40 |
| NO. 403 | BL0646 | 799779 | 800444 | + | possible glucose inhibited division protein b. | swiss|O54571|GIDB_STRCO | 4.00E−33 |
| NO. 404 | BL0647 | 800655 | 801665 | + | chromosome partitioning protein para (parA) | trembl|AF187159|AF187159_5 | 1.00E−76 |
| NO. 405 | BL0648 | 801665 | 803026 | + | probable chromosome partitioning protein (parB) | trembl|AF031590|AF031590_3 | 4.00E−68 |
| NO. 406 | BL0649 | 803332 | 804357 | complement | thioredoxin reductase (EC 1.6.4.5) (trxB) | swissnew|O30973|TRXB_MYCSM | 4.00E−87 |
| NO. 407 | BL0651 | 806617 | 808344 | complement | conserved hypothetical membrane protein in mvin | trembl|AL049826|SCH24_16 | 2.00E−50 |
| NO. 408 | BL0653 | 810608 | 812059 | complement | hypothetical protein with possible c-terminal | trembl|Z94121|MTY15F10_27 | 3.00E−28 |
| NO. 409 | BL0654 | 811999 | 813402 | + | probable rna nucleotidyltransferase (pcnA or | trembl|AL049826|SCH24_18 | 5.00E−162 |
| NO. 410 | BL0656 | 814163 | 815113 | complement | 4-diphosphocytidyl-2-c-methyl-d-erythritol | swissnew|O05596|ISPE_MYCTU | 1.00E−30 |
| NO. 411 | BL0657 | 815110 | 816036 | complement | dimethyladenosine transferase (EC 2.1.1.-) | trembl|Z94752|MTC1237_22 | 8.00E−66 |
| NO. 412 | BL0660 | 819239 | 821479 | complement | widely conserved protein with eukaryotic protein | trembl|AL157953|SCL11_7 | 7.00E−34 |
| NO. 413 | BL0669 | 826542 | 826949 | + | nrdi-like protein (nrdI) | swiss|P95107|NRDI_MYCTU | 1.00E−33 |
| NO. 414 | BL0670 | 827065 | 829260 | + | ribonucleoside-diphosphate reductase 2 alpha | trembl|L34407|MTRSOR_1 | 0 |
| NO. 415 | BL0671 | 829572 | 830564 | + | ribonucleoside-diphosphate reductase 2 beta | trembl|U41100|MT41100_1 | 5.00E−153 |
| NO. 416 | BL0672 | 830643 | 831803 | + | probable glycosyltransferase | tremblnew|AF267127|AF267127_11 | 1.00E−33 |
| NO. 417 | BL0673 | 832163 | 833290 | + | atp binding protein of abc transporter for | trembl|Y08921|SRMSIK_1 | 5.00E−127 |
| NO. 418 | BL0676 | 843651 | 844637 | + | sortase-like protein similar to | trembl|AF019629|AF019629_2 | 4.00E−43 |
| NO. 419 | BL0679 | 845958 | 847370 | + | narrowly conserved hypothetical protein with | trembl|AL357613|SC5F8_10 | 5.00E−116 |
| NO. 420 | BL0680 | 847477 | 847986 | complement | possible trna/rrna methyltransferase (EC | gp|AL160331|7242757 | 2.00E−66 |
| NO. 421 | BL0681 | 848557 | 849855 | + | conserved hypothetical transport protein | tremblnew|AP001518|AP001518_42 | 7.00E−28 |
| NO. 422 | BL0682 | 849868 | 850764 | + | protein probably involved in xylan degradation; | swiss|P26223|XYNB_BUTFI | 9.00E−35 |
| NO. 423 | BL0683 | 850947 | 853934 | + | cation-transporting atpase pacl (EC 3.6.1.-) | tremblnew|AP001515|AP001515_249 | 0 |
| NO. 424 | BL0684 | 854349 | 855533 | + | transpsosase in is256 family | swiss|Q52873|TRA5_RHIME | 5.00E−61 |
| NO. 425 | BL0685 | 855689 | 856459 | + | hisf cyclase (hisF) | trembl|AL096884|SC4G6_17 | 2.00E−96 |
| NO. 426 | BL0686 | 856593 | 856988 | + | probable phosphoribosyl-amp cyclohydrolase (EC | trembl|AL096884|SC4G6_13 | 4.00E−39 |
| NO. 427 | BL0687 | 857069 | 858625 | + | anthranilate synthase component i (EC 4.1.3.27) | swiss|P96556|TRPE_ARTGO | 5.00E−147 |
| NO. 428 | BL0689 | 858941 | 860542 | + | atp binding protein of abc transporter | trembl|AL132644|SCI8_25 | 0 |
| NO. 429 | BL0691 | 861364 | 861732 | + | narrowly conserved protein with unknown | trembl|AL118514|SCD25_30 | 9.00E−23 |
| NO. 430 | BL0693 | 862453 | 864066 | complement | atp binding protein of abc transporter | trembl|AE000829|AE000829_9 | 3.00E−67 |
| NO. 431 | BL0696 | 865593 | 866864 | complement | is30-type transposase | trembl|AL021646|MTV014_36 | 1.00E−78 |
| NO. 432 | BL0702 | 875125 | 878160 | + | excinuclease abc subunit a (uvrA) | swiss|P94972|UVRA_MYCTU | 0 |
| NO. 433 | BL0703 | 878310 | 880676 | + | excinuclease abc subunit c (uvrC) | swiss|Q9Z512|UVRC_STRCO | 5.00E−180 |
| NO. 434 | BL0704 | 880785 | 881756 | + | probable shikimate 5-dehydrogenase (EC 1.1.1.25) | trembl|Z83863|MTCY159_29 | 9.00E−27 |
| NO. 435 | BL0705 | 881756 | 882742 | + | widely conserved hypothetical protein with | trembl|AF106003|AF106003_2 | 4.00E−82 |
| NO. 436 | BL0706 | 882941 | 883891 | + | narrowly conserved hypothetical protein with | trembl|Z80108|MTCY21B4_38 | 2.00E−71 |
| NO. 437 | BL0707 | 883940 | 885265 | + | phosphoglycerate kinase (EC 2.7.2.3) (pgk) | swiss|Q9Z519|PGK_STRCO | 5.00E−137 |
| NO. 438 | BL0708 | 885322 | 886125 | + | triosephosphate isomerase (EC 5.3.1.1) (tim) | swiss|O08408|TPIS_MYCTU | 9.00E−68 |
| NO. 439 | BL0710 | 886539 | 887489 | + | l-lactate dehydrogenase (EC 1.1.1.27) (ldh) | trembl|AB033627|AB033627_1 | 1.00E−67 |
| NO. 440 | BL0712 | 888460 | 890004 | + | probable aminotransferase hi0286 (EC 2.6.1.-) | swiss|P71348|YFBQ_HAEIN | 5.00E−151 |
| NO. 441 | BL0714 | 891415 | 892752 | complement | branched-chain amino acid transport system | trembl|U79494|BSU79494_1 | 3.00E−73 |
| NO. 442 | BL0715 | 892881 | 893984 | complement | transaldolase (EC 2.2.1.2) (tal) | swiss|O06812|TAL_MYCTU | 5.00E−108 |
| NO. 443 | BL0716 | 894105 | 896213 | complement | transketolase (EC 2.2.1.1) (tkt) | trembl|AL03I107|SC5A7_13 | 0 |

TABLE I-continued

| | Gene Name | Start | Stop | Strand | Function | Best Hit | Best Score |
|---|---|---|---|---|---|---|---|
| NO. 444 | BL0718 | 896588 | 897706 | + | heat-inducible transcription repressor (hrcA) | swissnew\|Q9RDD6\|HRCA_STRCO | 1.00E−70 |
| NO. 445 | BL0719 | 897762 | 898907 | + | chaperone protein (dnaJ) | swissnew\|O05825\|DNJ2_MYCTU | 4.00E−91 |
| NO. 446 | BL0720 | 898953 | 899744 | complement | conserved hypothetical protein with unknown | trembl\|D90916\|SSD916_76 | 9.00E−21 |
| NO. 447 | BL0721 | 899889 | 900773 | + | possible undecaprenol kinase (bacA?) | trembl\|Z95388\|MTCY270_6 | 9.00E−54 |
| NO. 448 | BL0722 | 900930 | 901787 | complement | narrowly conserved hypothetical protein with | trembl\|U00017\|ML017_28 | 3.00E−35 |
| NO. 449 | BL0724 | 902583 | 904616 | + | threonyl-trna synthetase (EC 6.1.1.3) | trembl\|AL137778\|SCL2_21 | 0 |
| NO. 450 | BL0725 | 904756 | 905340 | + | conserved hypothetical protein with hit domain | trembl\|AL137778\|SCL2_20 | 1.00E−49 |
| NO. 451 | BL0726 | 905479 | 906234 | + | widely conserved hypothetical protein in upf102 | swiss\|O33214\|YQ03_MYCTU | 3.00E−84 |
| NO. 452 | BL0727 | 906240 | 906824 | + | crossover junction endodeoxyribonuclease ruve | swiss\|Q50627\|RUVC_MYCTU | 2.00E−42 |
| NO. 453 | BL0728 | 906882 | 907508 | + | probable holliday junction dna helicase ruva. | trembl\|AL137778\|SCL2_9 | 3.00E−29 |
| NO. 454 | BL0729 | 907508 | 908572 | + | holliday junction dna helicase ruvb. (ruvB) | trembl\|AL137778\|SCL2_8 | 5.00E−113 |
| NO. 455 | BL0731 | 909135 | 909716 | + | adenine phosphoribosyltransferase (EC 2.4.2.7) | tremblnew\|AE005226\|AE005226_1 | 1.00E−36 |
| NO. 456 | BL0732 | 909813 | 911015 | + | succinyl-coa synthetase beta chain (EC 6.2.1.5) | trembl\|AL035500\|MLCL373_3 | 2.00E−95 |
| NO. 457 | BL0733 | 911015 | 911926 | + | succinyl-coa synthetase alpha chain (EC 6.2.1.5) | trembl\|AL035500\|MLCL373_4 | 3.00E−98 |
| NO. 458 | BL0735 | 913273 | 914910 | + | bifunctional purine biosynthesis protein purh | trembl\|AB003159\|AB003159_3 | 5.00E−171 |
| NO. 459 | BL0737 | 916421 | 917191 | + | ribosomal large subunit pseudouridine synthase b | swiss\|O33210\|YHI1_MYCTU | 2.00E−63 |
| NO. 460 | BL0738 | 917926 | 919317 | + | probable gtp binding protein | tremblnew\|AL445403\|SC2134_11 | 5.00E−164 |
| NO. 461 | BL0739 | 919672 | 921201 | + | probable utp-glucose-1-phosphate | swissnew\|Q9SDX3\|UDPG_MUSAC | 5.00E−57 |
| NO. 462 | BL0742 | 923595 | 926186 | + | probable helicase (helY) | trembl\|AL132648\|SCI41_14 | 5.00E−150 |
| NO. 463 | BL0743 | 926301 | 926648 | + | narrowly conserved hypothetical protein with | trembl\|AL133213\|SC6D7_15 | 3.00E−23 |
| NO. 464 | BL0746 | 928449 | 929081 | complement | hypothetical protein with possible regulatory | swiss\|Q50603\|YI30_MYCTU | 4.00E−34 |
| NO. 465 | BL0747 | 929182 | 929625 | complement | possible signal transduction protein (garA) | trembl\|AF173844\|AF173844_2 | 8.00E−28 |
| NO. 466 | BL0748 | 929632 | 930453 | complement | narrowly conserved hypothetical protein with | swiss\|Q50608\|YI25_MYCTU | 4.00E−23 |
| NO. 467 | BL0748a | 930469 | 930801 | complement | hypothetical membrane protein with unknown | swiss\|Q50609\|YI24_MYCTU | 1.00E−30 |
| NO. 468 | BL0750 | 931768 | 932385 | complement | possible | swiss\|Q50611\|PGSA_MYCTU | 2.00E−22 |
| NO. 469 | BL0751 | 932399 | 933250 | complement | atp phosphoribosyltransferase (EC 2.4.2.17) | swiss\|O33256\|HIS1_MYCTU | 2.00E−73 |
| NO. 470 | BL0752 | 933262 | 933525 | complement | phosphoribosyl-atp pyrophosphatase (EC 3.6.1.31) | swissnew\|Q49786\|HIS2_MYCLE | 2.00E−25 |
| NO. 471 | BL0753 | 933588 | 934256 | complement | ribulose-phosphate 3-epimerase (EC 5.1.3.1) | gp\|AL159139\|7209224 | 2.00E−69 |
| NO. 472 | BL0754 | 934332 | 935279 | complement | probable prolipoprotein diacylglyceryl | trembl\|AL096884\|SC4G6_3 | 3.00E−55 |
| NO. 473 | BL0755 | 935392 | 936267 | complement | tryptophan synthase alpha chain (EC 4.2.1.20) | swiss\|O68906\|TRPA_MYCIT | 6.00E−65 |
| NO. 474 | BL0756 | 936285 | 938372 | complement | tryptophan synthase beta chain (EC 4.2.1.20) | swissnew\|O05625\|TRPB_STRCO | 5.00E−138 |
| NO. 475 | BL0757 | 938899 | 939750 | complement | probable endonuclease iv (EC 3.1.21.2) | tremblnew\|AP001511\|AP001511_275 | 1.00E−52 |
| NO. 476 | BL0758 | 939874 | 941274 | + | amino acid permease | trembl\|AB006424\|AB006424_71 | 5.00E−153 |
| NO. 477 | BL0764 | 944658 | 945116 | complement | narrowly conserved hypothetical protein with | trembl\|AL031317\|SC6G4_19 | 9.00E−34 |
| NO. 478 | BL0774 | 951598 | 952218 | complement | mutt-like protein | tremblnew\|AP001517\|AP001517_211 | 2.00E−37 |
| NO. 479 | BL0778 | 954363 | 955937 | + | histidine permease (hutM) | trembl\|AB006424\|AB006424_71 | 5.00E−165 |
| NO. 480 | BL0779 | 956141 | 956791 | complement | probable signal peptidase i-2 (EC 3.4.21.89) | trembl\|AL023797\|SC2E1_15 | 6.00E−37 |
| NO. 481 | BL0783 | 959691 | 960881 | + | probable aminotransferase | trembl\|Z99109\|BSUB0006_32 | 2.00E−65 |
| NO. 482 | BL0784 | 960921 | 962684 | + | conserved hypothetical protein with unknown | trembl\|AL031317\|SC6G4_20 | 1.00E−50 |
| NO. 483 | BL0786 | 963517 | 964440 | + | lysr-type transcriptional regulator (cpsY) | trembl\|Y17221\|SA17221_1 | 4.00E−81 |
| NO. 484 | BL0788 | 966192 | 966887 | complement | orotate phosphoribosyltransferase (EC 2.4.2.10) | swiss\|P50587\|PYRE_PSEAE | 3.00E−44 |
| NO. 485 | BL0789 | 966896 | 967867 | complement | dihydroorotate dehydrogenase (EC 1.3.3.1) | swissnew\|O66461\|PYRD_AQUAE | 4.00E−69 |

TABLE I-continued

| | Gene Name | Start | Stop | Strand | Function | Best Hit | Best Score |
|---|---|---|---|---|---|---|---|
| NO. 486 | BL0790 | 967870 | 968694 | complement | probable dihydroorotate dehydrogenase electron | swissnew|P25983|PYRK_BACSU | 6.00E−31 |
| NO. 487 | BL0791 | 968830 | 969783 | complement | orotidine 5′-phosphate decarboxylase (EC | trembl|AE002053|AE002053_4 | 2.00E−39 |
| NO. 488 | BL0792 | 969801 | 971297 | complement | dihydroorotase (EC 3.5.2.3) (dhoase) (pyrC) | swissnew|P46538|PYRC_BACCL | 6.00E−58 |
| NO. 489 | BL0793 | 971294 | 971713 | complement | aspartate carbamoyltransferase regulatory chain | swiss|O26938|PYRI_METTH | 2.00E−24 |
| NO. 490 | BL0794 | 971713 | 972693 | complement | aspartate carbamoyltransferase (EC 2.1.3.2) | swiss|P77918|PYRB_PYRAB | 2.00E−79 |
| NO. 491 | BL0795 | 972817 | 976047 | complement | glutamate-ammonia-ligase adenylyltransferase (EC | swiss|Q10379|GLNE_MYCTU | 5.00E−179 |
| NO. 492 | BL0796 | 976103 | 977056 | complement | choloylglycine hydrolase (EC 3.5.1.24) | trembl|AF054971|AF054971_3 | 3.00E−73 |
| NO. 493 | BL0797 | 977190 | 978044 | complement | 5,10-methylenetetrahydrofolate reductase (EC | trembl|AL139077|CJ11168X4_191 | 3.00E−56 |
| NO. 494 | BL0798 | 978103 | 980406 | complement | 5-methyltetrahydropteroyltri-glutamate-homocysteine | swissnew|Q9PN94|METE_CAMJE | 0 |
| NO. 495 | BL0800 | 981301 | 982371 | complement | hypothetical protein with similarity to pirnt | trembl|AL132648|SCI41_34 | 3.00E−63 |
| NO. 496 | BL0804 | 983910 | 984647 | complement | probable transcriptional activator similar to | tremblnew|AP001516|AP001516_108 | 5.00E−38 |
| NO. 497 | BL0806 | 985707 | 986216 | + | conserved hypothetical protein with unknown | pironly|E83182|E83182 | 1.00E−33 |
| NO. 498 | BL0821 | 996596 | 997183 | complement | possible thioredoxin-dependent thiol peroxidase | gp|AL353832|7636005 | 2.00E−38 |
| NO. 499 | BL0825 | 999293 | 1000039 | complement | probable atp binding protein of abc transporter | trembl|AL021287|MTV012_55 | 6.00E−45 |
| NO. 500 | BL0826 | 1000307 | 1001557 | complement | possible glycosyltransferase (glgA) | trembl|AL133278|SCM11_17 | 5.00E−110 |
| NO. 501 | BL0829 | 1004313 | 1005953 | complement | probable oligopeptide binding protein of abc | trembl|AL022121|MTV025_15 | 5.00E−126 |
| NO. 502 | BL0833 | 1008077 | 1009612 | complement | glutamate synthase [nadph] small subunit (EC | trembl|AL109849|SC3A3_3 | 5.00E−151 |
| NO. 503 | BL0834 | 1009614 | 1014185 | complement | glutamate synthase [nadph] large subunit (EC | trembl|AL109849|SC3A3_4 | 0 |
| NO. 504 | BL0838 | 1017184 | 1018230 | complement | laci-type transcriptional regulator | trembl|AL158061|SC6D11_7 | 1.00E−45 |
| NO. 505 | BL0842 | 1020867 | 1021508 | + | widely conserved hypothetical transmembrane | tremblnew|AP001514|AP001514_169 | 3.00E_27 |
| NO. 506 | BL0843 | 1021558 | 1022742 | complement | transpsosase in is256 family | swiss|Q52873|TRAS_RHIME | 5.00E−61 |
| NO. 507 | BL0844 | 1022814 | 1023548 | + | conserved hypothetical transmembrane protein | tremblnew|AP001514|AP001514_169 | 2.00E−20 |
| NO. 508 | BL0845 | 1023926 | 1025146 | complement | glycerate kinase (EC 2.7.1.31) (glxK) | swissnew|P42100|GRK_BACSU | 1.00E−83 |
| NO. 509 | BL0846 | 1025243 | 1026343 | + | laci-type transcriptional regulator | trembl|AB016845|AB016845_1 | 3.00E−36 |
| NO. 510 | BL0847 | 1026423 | 1027832 | complement | probable oxygen-independent coproporphyrinogen | trembl|AL136503|SCC77_26 | 6.00E−80 |
| NO. 511 | BL0848 | 1027832 | 1029712 | complement | gtp-binding protein lepa (lepA) | swiss|P71739|LEPA_MYCTU | 0 |
| NO. 512 | BL0850 | 1030371 | 1031162 | complement | conserved hypothetical transmembrane protein | swissnew|O86576|YU26_STRCO | 6.00E−35 |
| NO. 513 | BL0851 | 1031410 | 1032342 | complement | conserved hypothetical protein similar to mazg | swiss|P33653|YBL1_STRCI | 8.00E−27 |
| NO. 514 | BL0852 | 1032503 | 1033630 | complement | probable branched-chain amino acid | piromly|A82612|A82612 | 5.00E−103 |
| NO. 515 | BL0853 | 1033855 | 1034475 | complement | probable 50s ribosomal protein 125 (rpIY) | swiss|P96385|RL25_MYCTU | 4.00E−28 |
| NO. 516 | BL0856 | 1036138 | 1037562 | complement | nad(p) transhydrogenase subunit beta (EC | trembl|U05294|RR05294_3 | 5.00E−101 |
| NO. 517 | BL0857 | 1037883 | 1039046 | complement | nad(p) transhydrogenase subunit alpha part 1 (EC | trembl|Z92770|MTCI5_28 | 5.00E−57 |
| NO. 518 | BL0858 | 1039387 | 1041498 | + | long-chain-fatty-acid-coa ligase (fadD15) | trembl|AL021957|MTV021_21 | 5.00E−115 |
| NO. 519 | BL0859 | 1041551 | 1042615 | complement | widely conserved gtp-binding protein (bex) | swiss|O05834|ERA_MYCTU | 2.00E−77 |
| NO. 520 | BL0860 | 1042617 | 1044050 | complement | probable conserved integral membrane protein | swiss|O05832|YN66_MYCTU | 4.00E−64 |
| NO. 521 | BL0861 | 1044126 | 1044674 | complement | conserved hypothetical protein with duf0054 | swiss|O05831|YN67_MYCTU | 2.00E−35 |
| NO. 522 | BL0862 | 1044664 | 1045839 | complement | phoh-like protein. | trembl|AL136534|SCC117_5 | 2.00E−83 |
| NO. 523 | BL0863 | 1045858 | 1046196 | complement | hypothetical protein in hit family | trembl|AL136503|SCC77_15 | 1.00E−28 |
| NO. 524 | BL0864 | 1046245 | 1047042 | complement | conserved hypothetical protein with similarity | trembl|AL136503|SCC77_19 | 4.00E−28 |
| NO. 525 | BL0865 | 1047286 | 1048164 | + | possible trna/rrna methyltransferase (EC | trembl|AL157953|SCL11_8 | 3.00E−65 |

TABLE I-continued

| | Gene Name | Start | Stop | Strand | Function | Best Hit | Best Score |
|---|---|---|---|---|---|---|---|
| NO. 526 | BL0866 | 1048365 | 1049609 | + | glucose-1-phosphate adenylyltransferase (EC | swiss\|O05314\|GLGC_MYCTU | 5.00E−122 |
| NO. 527 | BL0867 | 1049699 | 1050292 | complement | conserved hypothetical protein with duf59 | trembl\|AL021184\|MTV007_13 | 3.00E−26 |
| NO. 528 | BL0868 | 1050299 | 1050838 | complement | hypothetical protein with nifu-like domain | trembl\|AL096839\|SCC22_2 | 1.00E−29 |
| NO. 529 | BL0869 | 1050865 | 1052139 | complement | nifs-like aminotranferase | trembl\|AL021184\|MTV007_11 | 5.00E−103 |
| NO. 530 | BL0870 | 1052278 | 1053057 | complement | probable atp binding protein of abc transporter | trembl\|AL096839\|SCC22_4 | 5.00E−100 |
| NO. 531 | BL0871 | 1053083 | 1054318 | complement | possible abc transporter component | trembl\|AL096839\|SCC22_6 | 2.00E−82 |
| NO. 532 | BL0872 | 1054324 | 1055823 | complement | possible abc transporter component | trembl\|AL096839\|SCC22_7 | 0 |
| NO. 533 | BL0874 | 1057888 | 1059549 | complement | ctp synthase (EC 6.3.4.2) (utp-ammonia ligase) | trembl\|AL109848\|SCI51_16 | 0 |
| NO. 534 | BL0875 | 1059695 | 1060981 | complement | hypothetical protein in the m20/m25/m40 | trembl\|AF008220\|AF008220_96 | 3.00E−33 |
| NO. 535 | BL0876 | 1061195 | 1061641 | complement | probable 3-dehydroquinate dehydratase (EC | trembl\|AE001933\|AE001933_1 | 2.00E−33 |
| NO. 536 | BL0877 | 1061805 | 1063427 | complement | bifunctional shikimate kinase (EC 2.7.1.71)- | swiss\|Q9X5D2\|AROB_CORGL | 3.00E−91 |
| NO. 537 | BL0878 | 1063510 | 1064697 | complement | chorismate synthase (EC 4.6.1.4) | swissnew\|P95013\|AROC_MYCTU | 5.00E−134 |
| NO. 538 | BL0880 | 1065402 | 1066583 | complement | conserved hypothetical protein with duf175 | tremblnew\|AL445503\|SC2G38_36 | 2.00E−34 |
| NO. 539 | BL0882 | 1067061 | 1069742 | complement | alanyl-trna synthetase (EC 6.1.1.7) | swiss\|O07438\|SYA_MYCTU | 0 |
| NO. 540 | BL0885 | 1071666 | 1073525 | + | hypothetical protein with unknown function | trembl\|U93874\|BSU93874_12 | 5.00E−63 |
| NO. 541 | BL0886 | 1073616 | 1074242 | complement | 30s ribosomal protein s4 (rpsD) | trembl\|AF008220\|AF008220_126 | 7.00E−42 |
| NO. 542 | BL0887 | 1074441 | 1075409 | complement | atp binding protein of abc transporter | trembl\|AE001001\|AE001001_4 | 2.00E−36 |
| NO. 543 | BL0890 | 1077262 | 1079907 | complement | atp-dependent dna helicase pcra (EC 3.6.1.-) | trembl\|Z79700\|MTCY10D7_10 | 0 |
| NO. 544 | BL0891 | 1080024 | 1080605 | + | xanthine phosphoribosyltransferase (EC 2.42.-) | pironly\|E82984\|E82984 | 1.00E−45 |
| NO. 545 | BL0892 | 1080656 | 1082020 | + | xanthine/uracil permease (pbuX) | tremblnew\|AL162755\|NMA4Z2491_77 | 5.00E−65 |
| NO. 546 | BL0893 | 1082150 | 1082359 | complement | hypothetical protein with probable helix turn | trembl\|AL121854\|SCJ33_10 | 3.00E−23 |
| NO. 547 | BL0895 | 1083890 | 1084828 | + | narrowly conserved hypothetical protein with | trembl\|AL138977\|SC7F9_36 | 2.00E−28 |
| NO. 548 | BL0897 | 1085477 | 1086091 | + | probable pyrazinamidase/nicotinamidase (pncA) | trembl\|U59967\|MT59967_1 | 5.00E−40 |
| NO. 549 | BL0901 | 1090564 | 1091640 | complement | probable atp binding protein of abc transporter | tremblnew\|AP001514\|AP001514_104 | 2.00E−58 |
| NO. 550 | BL0903 | 1093282 | 1093938 | + | response regulator of two-component system | trembl\|AL079332\|SCI5_9 | 7.00E−32 |
| NO. 551 | BL0905 | 1094763 | 1095815 | complement | hypothetical protein in pho-4 inorganic | swiss\|O34436\|PIT_BACSU | 5.00E−50 |
| NO. 552 | BL0906 | 1096190 | 1098589 | complement | carbon starvation protein a (cstA) | swiss\|P95095\|CSTA_MYCTU | 0 |
| NO. 553 | BL0907 | 1098732 | 1100129 | + | possible cyclomaltodextrinase (EC 3.2.1.54) or | tremblnew\|AP001517\|AP001517_49 | 2.00E−34 |
| NO. 554 | BL0909 | 1100941 | 1103127 | complement | possible atp-dependent rna helicase | gp\|AL159178\|7210999 | 1.00E−93 |
| NO. 555 | BL0910 | 1103507 | 1104796 | complement | probable purine or uracil permease (pyrP) | gp\|AL159139\|7209210 | 5.00E−107 |
| NO. 556 | BL0914 | 1107193 | 1108356 | complement | narrowly conserved hypothetical protein with | trembl\|Y17797\|EFY17797_6 | 1.00E−37 |
| NO. 557 | BL0918 | 1111212 | 1112912 | + | hypothetical protein with probable | swiss\|P71584\|PKNB_MYCTU | 4.00E−23 |
| NO. 558 | BL0919 | 1112950 | 1114440 | complement | possible efflux transporter protein | trembl\|X92946\|LLLPK214_12 | 1.00E−31 |
| NO. 559 | BL0920 | 1114752 | 1116803 | complement | possible efflux transporter protein | trembl\|D50453\|BSD453_85 | 6.00E−96 |
| NO. 560 | BL0926 | 1121476 | 1122570 | complement | widely conserved hypothetical gtpase-like | trembl\|AL021897\|MTV017_64 | 5.00E−125 |
| NO. 561 | BL0927 | 1122588 | 1123388 | complement | pyrroline-5-carboxylate reductase (EC 1.5.1.2) | swiss\|P27771\|PROC_TREPA | 1.00E−50 |
| NO. 562 | BL0928 | 1123463 | 1124806 | complement | proline iminopeptidase (EC 3.4.11.5) (pip) | trembl\|D61383\|HAD383_1 | 5.00E−103 |
| NO. 563 | BL0929 | 1125017 | 1127593 | + | histidine kinase sensor of two-component | trembl\|AL049630\|SCE126_8 | 5.00E−36 |
| NO. 564 | BL0930 | 1127669 | 1128415 | + | response regulator of two-component system | trembl\|AL031155\|SC3A7_31 | 2.00E−55 |
| NO. 565 | BL0931 | 1128507 | 1131149 | complement | possible transport protein | trembl\|AL021999\|MTV044_11 | 3.00E−22 |
| NO. 566 | BL0932 | 1131191 | 1131982 | complement | possible atp binding protein of abc transporter | gp\|AL159178\|7211019 | 8.00E−64 |

TABLE I-continued

| | Gene Name | Start | Stop | Strand | Function | Best Hit | Best Score |
|---|---|---|---|---|---|---|---|
| NO. 567 | BL0933 | 1132331 | 1133647 | complement | o-acetylhomoserine (thiol)-lyase (EC 4.2.99.10) | tremblnew|AP001516|AP001516__32 | 5.00E−134 |
| NO. 568 | BL0934 | 1134200 | 1135072 | + | possible pyridoxine kinase (EC 2.7.1.35) | trembl|AE001176|AE001176__8 | 1.00E−24 |
| NO. 569 | BL0936 | 1135870 | 1137405 | + | conserved hypothetical protein in chelatase | swiss|Q10818|YS97__MYCTU | 5.00E−118 |
| NO. 570 | BL0937 | 1137402 | 1139102 | + | hypothetical protein with partial similarity to | swiss|Q10817|YS96__MYCTU | 5.00E−29 |
| NO. 571 | BL0938 | 1139159 | 1141024 | + | succinate dehydrogenase flavoprotein subunit (EC | trembl|AL021841|MTV016__16 | 5.00E−137 |
| NO. 572 | BL0939 | 1141120 | 1142085 | + | probable iorn sulfur protein associated with | trembl|AL021841|MTV016__17 | 6.00E−35 |
| NO. 573 | BL0941 | 1142890 | 1143831 | complement | conserved hypothetical protein with unknown | trembl|X81379|CGDAPE__2 | 9.00E−61 |
| NO. 574 | BL0942 | 1144064 | 1145482 | complement | probable sodium/proton antiporter (nhaA) | trembl|AL035636|SCH5__27 | 4.00E−69 |
| NO. 575 | BL0943 | 1145964 | 1147457 | complement | atp-dependent specificity component of theclp | trembl|X95306|BSCLPXGEN__1 | 5.00E−128 |
| NO. 576 | BL0944 | 1147504 | 1148205 | complement | atp-dependent clp protease proteolytic subunit 2 | trembl|AF071885|AF071885__2 | 7.00E−72 |
| NO. 577 | BL0945 | 1148211 | 1148834 | complement | atp-dependent clp protease proteolytic subunit 1 | swiss|O53188|CLP1__MYCTU | 1.00E−57 |
| NO. 578 | BL0946 | 1149435 | 1150901 | complement | conserved hypothetical protein with unknown | trembl|AF179611|AF179611__12 | 2.00E−30 |
| NO. 579 | BL0947 | 1151085 | 1152464 | complement | trigger factor chaperone (tf) (tig) | swissnew|O53189|TIG__MYCTU | 5.00E−79 |
| NO. 580 | BL0948 | 1152519 | 1153820 | complement | narrowly conserved hypothetical protein with | trembl|AL023702|SC1C3__16 | 1.00E−75 |
| NO. 581 | BL0950 | 1154518 | 1155399 | complement | pyruvate formate-lyase 1 activating enzyme (EC | trembl|AF088897|AF088897__13 | 9.00E−54 |
| NO. 582 | BL0951 | 1155509 | 1157923 | complement | formate acetyltransferase (EC 2.3.1.54) | trembl|AF088897|AF088897__12 | 0 |
| NO. 583 | BL0953 | 1158427 | 1160124 | complement | glutamine-dependent nad(+) synthetase (EC | trembl|Y17736|SCY17736__1 | 5.00E−132 |
| NO. 584 | BL0954 | 1160473 | 1161624 | complement | widely conserved hypothetical protein with | swissnew|O34980|YTNL__BACSU | 6.00E−75 |
| NO. 585 | BL0955 | 1161713 | 1162399 | complement | permease protein of abc transporter system | trembl|AE001982|AE001982__3 | 2.00E−40 |
| NO. 586 | BL0956 | 1162396 | 1163601 | complement | atp binding protein of abc transporter | tremblnew|AP001518|AP001518__312 | 8.00E−77 |
| NO. 587 | BL0957 | 1163735 | 1164715 | complement | hypothetical protein with similarity to proteins | swiss|Q08870|PLPC__PASHA | 5.00E−36 |
| NO. 588 | BL0958 | 1164917 | 1165738 | + | possible had-type hydrolase | trembl|AF012285|AF012285__30 | 2.00E−24 |
| NO. 589 | BL0959 | 1165860 | 1168337 | complement | xylulose-5-phosphate/fructose-6-phosphate | trembl|D90917|SSD917__62 | 0 |
| NO. 590 | BL0960 | 1168738 | 1170345 | + | gmp synthase glutamine amidotransferase (guaA) | gp|AL161755|7320904 | 0 |
| NO. 591 | BL0962 | 1170921 | 1172795 | + | hypothetical membrane protein with possible | trembl|U93874|BSU93874__12 | 4.00E−61 |
| NO. 592 | BL0963 | 1172872 | 1173903 | + | ribose-phosphate pyrophosphokinase (EC 2.7.6.1) | trembl|Z92539|MTCY10G2__4 | 5.00E−113 |
| NO. 593 | BL0964 | 1174185 | 1175567 | + | udp-n-acetylglucosamine pyrophosphorylase (EC | trembl|Z92539|MTCY10G2__5 | 5.00E−112 |
| NO. 594 | BL0965 | 1175571 | 1175984 | + | hypothetical protein with duf143 | trembl|AL136518|SCC123__15 | 1.00E−27 |
| NO. 595 | BL0966 | 1176166 | 1176864 | + | conserved hypothetical protein with unknown | trembl|AE001959|AE001959__11 | 2.00E−20 |
| NO. 596 | BL0968 | 1177494 | 1179194 | + | phosphate acetyltransferase (EC 2.3.1.8) | swiss|P96254|PTA__MYCTU | 3.00E−95 |
| NO. 597 | BL0969 | 1179329 | 1180558 | + | acetate kinase (EC 2.7.2.1) (acetokinase) | swiss|P77845|ACKA__CORGL | 5.00E−106 |
| NO. 598 | BL0970 | 1180729 | 1182096 | complement | 3-phosphoshikimate 1-carboxyvinyltransferase (EC | trembl|AF114233|AF114233__1 | 2.00E−96 |
| NO. 599 | BL0972 | 1183626 | 1184219 | + | hypothetical protein with site-specific | trembl|AL008967|MTV002__57 | 2.00E−43 |
| NO. 600 | BL0973 | 1184206 | 1185528 | + | probable transposase | trembl|AL008967|MTV002__56 | 1.00E−49 |
| NO. 601 | BL0976 | 1186907 | 1188394 | complement | galactoside symporter (lacS) | swissnew|Q48624|LACY__LEULA | 5.00E−149 |
| NO. 602 | BL0978 | 1188759 | 1191830 | + | beta-galactosidase (EC 3.2.1.23) (lactase) | trembl|AJ242596|BLO242596__1 | 0 |
| NO. 603 | BL0979 | 1192644 | 1193198 | + | dna-3-methyladenine glycosylase i (EC 3.2.2.20) | trembl|AJ242596|BLO242596__2 | 5.00E−108 |
| NO. 604 | BL0982 | 1194993 | 1197134 | complement | probable glycogen operon protein glgx (EC | gp|AB031392|7648481 | 0 |
| NO. 605 | BL0984 | 1197908 | 1198837 | complement | conserved hypothetical protein with duf34 | gp|AL352972|7619756 | 3.00E−46 |
| NO. 606 | BL0985 | 1198998 | 1201865 | complement | dna polymerase i (EC 2.7.7.7) (pol i) (polA) | swiss|Q07700|DPO1__MYCTU | 0 |

TABLE I-continued

| | Gene Name | Start | Stop | Strand | Function | Best Hit | Best Score |
|---|---|---|---|---|---|---|---|
| NO. 607 | BL0986 | 1201911 | 1202696 | complement | conserved hypothetical protein with a response | trembl|AL109732|SC7H2__27 | 2.00E−49 |
| NO. 608 | BL0988 | 1203789 | 1205318 | complement | pyruvate kinase (EC 2.7.1.40) | trembl|AL109732|SC7H2__28 | 5.00E−130 |
| NO. 609 | BL0989 | 1205399 | 1206385 | complement | widely conserved hypothetical protein with | trembl|AL035591|SCC54__23 | 2.00E−82 |
| NO. 610 | BL0990 | 1206554 | 1208665 | complement | excinuclease abc subunit b (uvrB) | swiss|O06150|UVRB_MYCTU | 0 |
| NO. 611 | BL0991 | 1208677 | 1209294 | complement | hypothetical protein in upf0038 | trembl|AL109732|SC7H2__10 | 7.00E−35 |
| NO. 612 | BL0992 | 1209468 | 1210943 | complement | 30s ribosomal protein s1 (rpsA) | trembl|AL109732|SC7H2__12 | 0 |
| NO. 613 | BL0993 | 1211063 | 1211941 | complement | bifunctional methylenetetrahydrofolate | trembl|AL009198|MTV004__11 | 6.00E−86 |
| NO. 614 | BL0994 | 1212042 | 1213238 | + | possible solute binding protein of abc | trembl|AL583918|MLEPRTN2__43 | 5.00E−29 |
| NO. 615 | BL0995 | 1213315 | 1214301 | + | atp binding protein of abc transporter (troB) | tremblnew|AP001511|AP001511__283 | 2.00E−27 |
| NO. 616 | BL0996 | 1214368 | 1215201 | + | possible permease of abc transporter system | pironly|F82959|F82959 | 4.00E−30 |
| NO. 617 | BL0997 | 1215253 | 1215777 | complement | 2c-methyl-d-erythritol 2,4-cyclodiphosphate | swissnew|P96863|ISPF_MYCTU | 5.00E−30 |
| NO. 618 | BL0998 | 1215886 | 1216479 | complement | possible transcriptional regulator | trembl|AL022075|MTV024__1 | 8.00E−46 |
| NO. 619 | BL0999 | 1216696 | 1218909 | + | 1,4-alpha-glucan branching enzyme (glgB) | swissnew|Q10625|GLGB_MYCTU | 0 |
| NO. 620 | BL1000 | 1218945 | 1219667 | + | response regulator of two-component system | trembl|Z95121|MTY20B11__21 | 3.00E−47 |
| NO. 621 | BL1001 | 1219664 | 1220740 | + | histidine kinase sensor of two-component system | tremblnew|AP001513|AP001513__218 | 1.00E−37 |
| NO. 622 | BL1007 | 1224806 | 1227901 | complement | narrowly conserved hypothetical protein with | trembl|L22864|SAWHIB12X__2 | 7.00E−26 |
| NO. 623 | BL1008 | 1227945 | 1228244 | complement | whib-type transcription regulator (whiB2) | trembl|AL021840|MTV015__3 | 8.00E−28 |
| NO. 624 | BL1009 | 1228495 | 1229928 | + | hypothetical protein with similarity to putative | trembl|AL023702|SC1C3__8 | 2.00E−25 |
| NO. 625 | BL1010 | 1230173 | 1231924 | + | hypothetical protein with ftsk/spoiiie domain | gp|AL160312|7242725 | 8.00E−48 |
| NO. 626 | BL1011 | 1232038 | 1232316 | + | whib-type transcription regulator wblE | trembl|AJ239087|SCO239087__1 | 1.00E−28 |
| NO. 627 | BL1012 | 1232389 | 1233921 | complement | histidine kinase-like protein | trembl|Z95120|MTCY7D11__18 | 7.00E−80 |
| NO. 628 | BL1014 | 1235063 | 1235881 | + | conserved hypothetical protein with unknown | trembl|AB003158|AB003158__1 | 5.00E−33 |
| NO. 629 | BL1015 | 1235936 | 1236415 | complement | transcription elongation factor grea (transcript | tremblnew|AL451182|SCK13__13 | 2.00E−31 |
| NO. 630 | BL1016 | 1236514 | 1236921 | complement | fk506-binding protein (peptidyl-prolyl cis-trans | pironly|S46228|S46228 | 2.00E−25 |
| NO. 631 | BL1017 | 1237063 | 1239282 | complement | l-serine dehydratase (EC 4.2.1.13) (l-serine | swiss|O86564|SDHL_STRCO | 5.00E−136 |
| NO. 632 | BL1019 | 1239669 | 1240670 | complement | possible exopolyphosphatase-like protein | trembl|Z92539|MTCY10G2__13 | 3.00E−57 |
| NO. 633 | BL1020 | 1240733 | 1241299 | complement | hypothetical protein with unknown function | trembl|Z92539|MTCY10G2__12 | 1.00E−30 |
| NO. 634 | BL1022 | 1241998 | 1243296 | complement | enolase (EC 4.2.1.11) (2-phosphoglycerate | swiss|P37869|ENO_BACSU | 5.00E−143 |
| NO. 635 | BL1023 | 1243447 | 1244394 | complement | possible oxidoreductase in aldo-keto reductase | trembl|AE002028|AE002028__7 | 9.00E−33 |
| NO. 636 | BL1025 | 1244534 | 1248118 | complement | transcription-repair coupling factor (mfd) | swiss|P96380|MFD_MYCTU | 0 |
| NO. 637 | BL1026 | 1248108 | 1248707 | complement | peptidyl-trna hydrolase (EC 3.1.1.29) (pth) | swiss|P96386|PTH_MYCTU | 2.00E−36 |
| NO. 638 | BL1028 | 1250516 | 1251013 | complement | possible n-acetyl transferase | trembl|AE001967|AE001967__8 | 1.00E−21 |
| NO. 639 | BL1029 | 1251136 | 1254336 | complement | narrowly conserved hypothetical protein with | trembl|AL021646|MTV014__38 | 5.00E−154 |
| NO. 640 | BL1031 | 1254509 | 1255711 | + | hypothetical protein in glycosyl hyrolase family | trembl|AL021929|MTV034__1 | 2.00E−21 |
| NO. 641 | BL1032 | 1255809 | 1256594 | complement | possible nicotinate-nucleotide | trembl|AL136518|SCC123__17 | 3.00E−69 |
| NO. 642 | BL1034 | 1257169 | 1258581 | complement | gamma-glutamyl phosphate reductase (gpr) (EC | trembl|AL136518|SCC123__23 | 5.00E−117 |
| NO. 643 | BL1035 | 1258586 | 1259287 | complement | serine hydroxymethyltransferase (glyA) | swiss|O53441|GLA1_MYCTU | 1.00E−40 |
| NO. 644 | BL1036 | 1259510 | 1261000 | + | threonine synthase (EC 4.2.99.2) (thrC) | swiss|Q42598|THRC_SCHPO | 7.00E−73 |
| NO. 645 | BL1038 | 1261520 | 1264306 | + | possible calcium-transporting atpase 10, plasma | trembl|AE000873|E000873__1 | 5.00E−149 |
| NO. 646 | BL1041 | 1265818 | 1266738 | complement | atp binding protein of abc transporter | tremblnew|AP001509|AP001509__90 | 5.00E−52 |
| NO. 647 | BL1041a | 1266760 | 1267134 | complement | possible gntr-family transcriptional regulator | tremblnew|AP001509|AP001509__89 | 3.00E−25 |
| NO. 648 | BL1043 | 1268017 | 1269819 | complement | dna repair protein recn (recombination protein | swissnew|Q9S220|RECN_STRCO | 2.00E−81 |

TABLE I-continued

| | Gene Name | Start | Stop | Strand | Function | Best Hit | Best Score |
|---|---|---|---|---|---|---|---|
| NO. 649 | BL1044 | 1269819 | 1270847 | complement | widely conserved hypothetical protein with | trembl|AL109848|SCI51__21 | 4.00E−59 |
| NO. 650 | BL1045 | 1271094 | 1272560 | + | hypothetical protein possibly involved in | trembl|Z99119|BSUB0016__183 | 2.00E−57 |
| NO. 651 | BL1046 | 1272611 | 1273273 | + | hypothetical protein possibly involved in | tremblnew|AP001509|AP001509__35 | 6.00E−31 |
| NO. 652 | BL1048 | 1274067 | 1274909 | complement | hemolysin-like protein with s4 domain found in | gp|AJ271681|7340781 | 4.00E−47 |
| NO. 653 | BL1049 | 1275097 | 1276137 | complement | conserved hypothetical protein with possible | trembl|AL109848|SCI51__28 | 1.00E−59 |
| NO. 654 | BL1050 | 1276146 | 1277933 | complement | hypothetical protein with unknown function | trembl|Z98268|MTCI125__12 | 2.00E−27 |
| NO. 655 | BL1051 | 1277961 | 1279283 | complement | tyrosyl-trna synthetase (EC 6.1.1.1) | trembl|AL132644|SC18__3 | 5.00E−122 |
| NO. 656 | BL1054 | 1281281 | 1282090 | complement | thiamine biosynthesis protein (thiF) | trembl|AE000735|AE000735__1 | 4.00E−81 |
| NO. 657 | BL1055 | 1282167 | 1283036 | complement | thiamine biosynthesis protein (thiG) | trembl|AL139077|CJ11168X4__37 | 2.00E−76 |
| NO. 658 | BL1057 | 1283591 | 1285063 | complement | argininosuccinate lyase (EC 4.3.2.1) | trembl|AL157956|SCL24__6 | 5.00E−162 |
| NO. 659 | BL1058 | 1285509 | 1286747 | complement | argininosuccinate synthase (EC 6.3.4.5) | swiss|P50986|ASSY__STRCL | 5.00E−152 |
| NO. 660 | BL1059 | 1286830 | 1287342 | complement | arginine repressor-like protein (argR) | trembl|AL157956|SCL24__12 | 3.00E−28 |
| NO. 661 | BL1060 | 1287339 | 1288304 | complement | ornithine carbamoyltransferase, anabolic (EC | swiss|P94991|OTCA__MYCTU | 6.00E−96 |
| NO. 662 | BL1061 | 1288348 | 1289643 | complement | acetylornithine aminotransferase (EC 2.6.1.11) | trembl|AL157956|SCL24__13 | 3.00E−85 |
| NO. 663 | BL1062 | 1289633 | 1290589 | complement | acetylglutamate kinase (EC 2.7.2.8) (nag kinase) | swiss|Q59281|ARGB__CORGL | 1.00E−93 |
| NO. 664 | BL1063 | 1290661 | 1291836 | complement | glutamate n-acetyltransferase (EC 2.3.1.35) | gp|Z49111|7328263 | 4.00E−91 |
| NO. 665 | BL1064 | 1291833 | 1292927 | complement | n-acetyl-gamma-glutamyl-phosphate reductase (EC | swiss|P54895|ARGC__STRCO | 5.00E−88 |
| NO. 666 | BL1066 | 1293743 | 1296352 | complement | phenylalanyl-trna synthetase beta chain (EC | swissnew|O88054|SYFB__STRCO | 5.00E−173 |
| NO. 667 | BL1067 | 1296360 | 1297427 | complement | phenylalanyl-trna synthetase alpha chain (EC | swissnew|P94984|SYFA__MYCTU | 5.00E−100 |
| NO. 668 | BL1068 | 1297481 | 1298365 | complement | possible rrna methylase | trembl|AL031541|SC135__19 | 6.00E−33 |
| NO. 669 | BL1070 | 1299379 | 1300782 | complement | atp binding protein of abc transporter | trembl|AJ002571|BSAJ2571__41 | 3.00E−70 |
| NO. 670 | BL1072 | 1301753 | 1303120 | complement | widely conserved protein in peptidase or | trembl|AL021185|MTV009__7 | 5.00E−94 |
| NO. 671 | BL1074 | 1303982 | 1305472 | + | dihydrolipoamide dehydrogenase (EC 1.8.1.4) | trembl|L38646|SEFORA__2 | 5.00E−76 |
| NO. 672 | BL1076 | 1306658 | 1308094 | + | glutamine synthetase 1 (EC 6.3.1.2) | tremblnew|AX063815|AX063815__1 | 0 |
| NO. 673 | BL1077 | 1308172 | 1308276 | complement | fragment of beta-glucuronidase | trembl|AF305888|AF305888__3 | 5.00E−20 |
| NO. 674 | BL1079 | 1309870 | 1310070 | + | fragment of laca | swissnew|P07464|THGA__ECOLI | 1.00E−22 |
| NO. 675 | BL1080 | 1310080 | 1310754 | complement | galactoside o-acetyltransferase (EC 2.3.1.18) | tremblnew|AE005213|AE005213__7 | 2.00E−47 |
| NO. 676 | BL1081 | 1310916 | 1311608 | complement | possible endonuclease iii | trembl|U67584|MJU67584__8 | 2.00E−30 |
| NO. 677 | BL1082 | 1311616 | 1312974 | complement | conserved hypothetical transmembrane protein in | tremblnew|AP001514|AP001514__169 | 9.00E−62 |
| NO. 678 | BL1083 | 1313032 | 1315629 | complement | excinuclease abc subunit a-like protein | trembl|AL133469|SCM10__6 | 5.00E−145 |
| NO. 679 | BL1090 | 1322865 | 1323908 | complement | possible alcohol dehydrogenase | trembl|U95372|U95372__2 | 6.00E−93 |
| NO. 680 | BL1094 | 1325764 | 1326828 | complement | conserved hypothetical protein with unknown | swiss|P33019|YEIH__ECOLI | 2.00E−31 |
| NO. 681 | BL1097 | 1328892 | 1330130 | complement | elongation factor tu (ef-tu) (tuf) | swiss|P31501|EFTU__MYCTU | 5.00E−173 |
| NO. 682 | BL1098 | 1330264 | 1332387 | complement | elongation factor g (ef-g) (fusA) | swiss|O53790|EFG__MYCTU | 0 |
| NO. 683 | BL1099 | 1332419 | 1332889 | complement | 30s ribosomal protein s7. (rpsG) | trembl|L34681|MSRPSLG__2 | 4.00E−64 |
| NO. 684 | BL1100 | 1332895 | 1333266 | complement | ribosomal protein s12 (rpsL) | swissnew|P97222|RS12__STRCO | 4.00E−55 |
| NO. 685 | BL1102 | 1334032 | 1335093 | complement | probable na+ dependent transporter possibly for | trembl|AF027868|AF027868__63 | 5.00E−64 |
| NO. 686 | BL1103 | 1335655 | 1336680 | + | possible low specificity-threonine aldolase | trembl|AE001274|AE001274__45 | 3.00E−68 |
| NO. 687 | BL1104 | 1336827 | 1337987 | complement | possible glycosyltransferase | trembl|AE001525|AE001525__12 | 2.00E−61 |
| NO. 688 | BL1105 | 1338155 | 1339498 | + | probable phosphoribosylglycinamide | pironly|B83176|B83176 | 3.00E−83 |
| NO. 689 | BL1107 | 1339891 | 1340643 | + | phosphoribosylaminoimidazole-succinocarboxamide | tremblnew|AP001509|AP001509__64 | 8.00E−68 |
| NO. 690 | BL1108 | 1340706 | 1344440 | + | phosphoribosylformyl-glycinamidine synthase (EC | trembl|U32759|HI32759__4 | 5.00E−50 |

TABLE I-continued

| | Gene Name | Start | Stop | Strand | Function | Best Hit | Best Score |
|---|---|---|---|---|---|---|---|
| NO. 691 | BL1109 | 1344331 | 1345875 | + | possible carboxylesterases or lipases. | tremblnew|AL512977|SSOLP2N16_40 | 1.00E−30 |
| NO. 692 | BL1111 | 1347888 | 1349402 | complement | possible na(+)/h(+) antiporter (sodium/proton) | pironly|G81187|G81187 | 5.00E−25 |
| NO. 693 | BL1113 | 1350694 | 1351671 | + | hypothetical protein in aldo/keto reductase 2 | trembl|AE002063|AE002063_8 | 6.00E−71 |
| NO. 694 | BL1114 | 1351920 | 1353515 | complement | hypothetical protein in impb/mucb/samb family of | trembl|AF188935|AF188935_69 | 1.00E−34 |
| NO. 695 | BL1115 | 1353674 | 1355176 | + | adenosylhomocysteinase (EC 3.3.1.1) | trembl|AP000060|AP000060_91 | 3.00E−61 |
| NO. 696 | BL1116 | 1355216 | 1356589 | + | possible chlorohydrolase-like protein | swiss|O29265|Y997_ARCFU | 1.00E−21 |
| NO. 697 | BL1119 | 1358229 | 1359191 | + | probable permease protein for abc transporter | trembl|AE001090|AE001090_13 | 4.00E−28 |
| NO. 698 | BL1120 | 1359188 | 1359973 | + | probable atp binding protein of abc transporter | trembl|AE001058|AE001058_14 | 7.00E−67 |
| NO. 699 | BL1121 | 1360377 | 1361888 | + | amidophosphoribosyltransferase precursor (EC | trembl|U64311|U64311_5 | 0 |
| NO. 700 | BL1122 | 1361954 | 1363045 | + | phosphoribosylformyl-glycinamidine cyclo-ligase | tremblnew|AP001509|AP001509_69 | 5.00E−123 |
| NO. 701 | BL1123 | 1363072 | 1364340 | + | phosphoribosylamine-glycine ligase (EC | swiss|Q9ZF44|PUR2_LACLA | 5.00E−130 |
| NO. 702 | BL1124 | 1364714 | 1366351 | complement | fatty aldehyde dehydrogenase (EC 1.2.1.3) | gp|AE003841|7304213 | 9.00E−81 |
| NO. 703 | BL1125 | 1366472 | 1368547 | complement | hypothetical protein with similarity to orf7 | trembl|AB010970|AB010970_8 | 2.00E−80 |
| NO. 704 | BL1128 | 1370243 | 1370683 | complement | probable metal uptake regulator similar to | trembl|AL137166|SCC121_11 | 6.00E−31 |
| NO. 705 | BL1129 | 1370680 | 1371858 | complement | phosphoribosylaminoimidazole carboxylase atpase | trembl|AJ000883|LLJ000883_4 | 5.00E−102 |
| NO. 706 | BL1130 | 1371842 | 1372348 | complement | phosphoribosylaminoimidazole carboxylase | swiss|P12044|PUR6_BACSU | 9.00E−58 |
| NO. 707 | BL1131 | 1372444 | 1373436 | complement | nadph: quinone oxidoreductases or alcohol | trembl|U75363|RPU75363_7 | 4.00E−42 |
| NO. 708 | BL1132 | 1373475 | 1375799 | + | probable l-deoxyxylulose-5-phosphate synthase | swiss|P26242|DXS_RHOCA | 1.00E−71 |
| NO. 709 | BL1135 | 1378547 | 1379302 | complement | atp binding protein of abc transporter | trembl|AE001033|AE001033_4 | 3.00E−56 |
| NO. 710 | BL1137 | 1380999 | 1382000 | complement | protein similar to hex regulon repressor | tremblnew|AL450223|SC7H9_11 | 5.00E−34 |
| NO. 711 | BL1138 | 1381966 | 1384275 | + | alpha-l-arabinofuranosidase a (EC 3.2.1.55) | trembl|U15178|BO15178_1 | 3.00E−70 |
| NO. 712 | BL1140 | 1384741 | 1385928 | complement | possible transport protein | swiss|P75788|YBIR_ECOLI | 3.00E−27 |
| NO. 713 | BL1142 | 1386478 | 1387410 | complement | l-asparaginase precursor (EC 3.5.1.1) | swiss|P37595|ASGX_ECOLI | 3.00E−49 |
| NO. 714 | BL1144 | 1387766 | 1389430 | complement | probable multiple substrate aminotransferase | trembl|AB027131|AB027131_1 | 4.00E−72 |
| NO. 715 | BL1145 | 1389488 | 1390126 | complement | conserved hypothetical protein in sno glutamine | trembl|AL137778|SCL2_12 | 5.00E−38 |
| NO. 716 | BL1146 | 1390212 | 1391183 | complement | widely conserved protein in upfoo19 probably | swiss|P45293|YG47_HAEIN | 5.00E−125 |
| NO. 717 | BL1147 | 1391279 | 1393387 | complement | dna primase (EC 2.7.7.-) (dnaG) | swissnew|O52200|PRIM_MYCSM | 5.00E−125 |
| NO. 718 | BL1148 | 1393551 | 1394978 | complement | deoxyguanosinetriphosphate triphosphohydrolase | trembl|AL137187|SC7A8_9 | 5.00E−108 |
| NO. 719 | BL1149 | 1395030 | 1396388 | complement | alanine racemase (EC 5.1.1.1) (alr) | swiss|O86786|ALR_STRCO | 6.00E−87 |
| NO. 720 | BL1150 | 1396601 | 1398037 | + | probable amino acid transporter (yfnA) | trembl|Z99109|BSUB0006_21 | 5.00E−150 |
| NO. 721 | BL1152 | 1399009 | 1399428 | complement | autoinducer-2 production protein luxs (ai-2) | swissnew|Q9XDU6|LUXS_CLOPE | 2.00E−24 |
| NO. 722 | BL1153 | 1399616 | 1401571 | complement | atp-dependent dna helicase recq (EC 3.6.1.-) | trembl|AF027868|AF027868_53 | 5.00E−117 |
| NO. 723 | BL1155 | 1403593 | 1404777 | complement | cystathionine gamma-synthase (EC 4.2.99.9) (cgs) | swiss|P46807|METB_MYCLE | 5.00E−126 |
| NO. 724 | BL1156 | 1404869 | 1406095 | complement | cystathionine beta-synthase (EC 4.2.1.22) | tremblnew|AF319543|AF319543_2 | 5.00E−121 |
| NO. 725 | BL1157 | 1406422 | 1407207 | complement | probable atp binding protein of abc transporter | tremblnew|AE005342|AE005342_4 | 4.00E−41 |
| NO. 726 | BL1158 | 1407200 | 1407991 | complement | probable atp-binding protein of abc transporter | trembl|AJ248288|CNSPAX06_207 | 4.00E−47 |
| NO. 727 | BL1159 | 1407988 | 1408890 | complement | probable abc transporter permease protein for | tremblnew|AP001507|AP001507_30 | 1.00E−33 |
| NO. 728 | BL1160 | 1408887 | 1409864 | complement | probable abc transporter permease protein for | trembl|AE000548|AE000548_6 | 5.00E−46 |
| NO. 729 | BL1161 | 1409929 | 1411548 | complement | solute binding protein of abc transporter | trembl|AP000003|AP000003_207 | 8.00E−39 |

TABLE I-continued

|  | Gene Name | Start | Stop | Strand | Function | Best Hit | Best Score |
|---|---|---|---|---|---|---|---|
| NO. 730 | BL1162 | 1411674 | 1412444 | + | conserved hypothetical protein with unknown | tremblnew|AP001507|AP001507__86 | 6.00E−52 |
| NO. 731 | BL1163 | 1412504 | 1413880 | complement | probable solute binding protein of abc | trembl|AL158061|SC6D11__4 | 7.00E−79 |
| NO. 732 | BL1164 | 1414041 | 1415384 | complement | probable solute binding protein of abc | trembl|AL158061|SC6D11__4 | 5.00E−108 |
| NO. 733 | BL1165 | 1415716 | 1417068 | complement | probable solute binding protein of abc | trembl|AL158061|SC6D11__4 | 5.00E−100 |
| NO. 734 | BL1166 | 1417228 | 1418928 | + | alpha-I-arabinofuranosidase a (EC 3.2.1.55) | gp|AL163003|7414545 | 5.00E−126 |
| NO. 735 | BL1167 | 1419048 | 1420085 | complement | laci-type transcriptional regulator | trembl|AE001777|AE001777__1 | 2.00E−44 |
| NO. 736 | BL1168 | 1420186 | 1422261 | complement | beta-galactosidase i (EC 3.2.1.23) (lactase) | trembl|AL158061|SC6D11__3 | 0 |
| NO. 737 | BL1169 | 1422476 | 1423486 | complement | probable permease of abc transporter system for | trembl|AL158061|SC6D11__5 | 5.00E−116 |
| NO. 738 | BL1170 | 1423542 | 1424474 | complement | probable permease of abc transporter system for | trembl|AL158061|SC6D11__6 | 5.00E−102 |
| NO. 739 | BL1171 | 1424691 | 1425701 | + | probable laci-type transcriptional regulator | trembl|AL158061|SC6D11__7 | 2.00E−68 |
| NO. 740 | BL1173 | 1426727 | 1427410 | + | hypothetical protein with similarity to hipa | swiss|P55564|Y4ME__RHISN | 2.00E−26 |
| NO. 741 | BL1174 | 1427453 | 1428154 | complement | possible ribosomal pseudouridine synthase | trembl|Z96070|MTCI418A__2 | 1.00E−44 |
| NO. 742 | BL1175 | 1428231 | 1430123 | complement | glucosamine-fructose-6-phosphate | trembl|AL031317|SC6G4__18 | 0 |
| NO. 743 | BL1176 | 1430365 | 1431195 | complement | atp binding protein of abc transporter | tremblnew|AF312768|AF312768__3 | 1.00E−77 |
| NO. 744 | BL1177 | 1431211 | 1432194 | complement | permease protein of abc transporter system | trembl|AF104994|AF104994__2 | 7.00E−59 |
| NO. 745 | BL1178 | 1432325 | 1433266 | complement | probable solute binding protein of abc | trembl|AF104994|AF104994__1 | 3.00E−38 |
| NO. 746 | BL1179 | 1433400 | 1434464 | complement | probable solute binding protein of abc | trembl|AF104994|AF104994__1 | 5.00E−39 |
| NO. 747 | BL1180 | 1434516 | 1435115 | complement | ssra-binding protein(smpB) | trembl|AL138851|SCE59__25 | 7.00E−52 |
| NO. 748 | BL1182 | 1436620 | 1437543 | complement | ftsx-like protein involved in cell division | trembl|AL138851|SCE59__27 | 3.00E−46 |
| NO. 749 | BL1183 | 1437555 | 1438724 | complement | ftse-like atp binding protein involved in cell | trembl|AL138851|SCE59__28 | 1.00E−80 |
| NO. 750 | BL1184 | 1438733 | 1439857 | complement | peptide chain release factor 2 (rf-2) (prfB) | trembl|AL138851|SCE59__31 | 5.00E−129 |
| NO. 751 | BL1186 | 1441718 | 1442371 | complement | polypeptide deformylase (EC 3.5.1.31) (pdf) | trembl|AL133422|SCM1__15 | 5.00E−45 |
| NO. 752 | BL1187 | 1442396 | 1443781 | complement | probable phosphoglucomutase or | trembl|AL031317|SC6G4__14 | 5.00E−129 |
| NO. 753 | BL1190 | 1444761 | 1445648 | complement | hypothetical transmembrane protein with unknown | trembl|U00011|ML011__29 | 2.00E−22 |
| NO. 754 | BL1191 | 1445826 | 1448435 | complement | aminopeptidase n ec 3.4.11.2) (lysyl | trembl|AL138662|SC8E4A__13 | 0 |
| NO. 755 | BL1192 | 1448477 | 1450390 | complement | widely conserved hypothetical protein with | trembl|AL031260|SC9A10__9 | 0 |
| NO. 756 | BL1193 | 1450412 | 1451317 | complement | dihydrodipicolinate synthase (EC 4.2.1.52) | trembl|AL008967|MTV002__18 | 1.00E−64 |
| NO. 757 | BL1194 | 1451480 | 1452235 | complement | dihydrodipicolinate reductase (EC 1.3.1.26) | trembl|AL008967|MTV002__38 | 1.00E−68 |
| NO. 758 | BL1195 | 1452571 | 1453890 | complement | possible transport protein | pironly|D83363|D83363 | 6.00E−42 |
| NO. 759 | BL1196 | 1454102 | 1458133 | complement | widely conserved atp-dependent dna helicase; | trembl|AL021646|MTV014__46 | 4.00E−71 |
| NO. 760 | BL1198 | 1462572 | 1463993 | + | probable serine/threonine-protein kinase (EC | trembl|Z83866|MTCY22D7__29 | 9.00E−35 |
| NO. 761 | BL1199 | 1464160 | 1470144 | + | large protein with c-terminal fibronectin type | tremblnew|AE007470|AE007470__2 | 2.00E−21 |
| NO. 762 | BL1199a | 1470155 | 1471528 | + | methanol dehydrogenase regulatory protein | trembl|AP001509|AP001509__42 | 2.00E−83 |
| NO. 763 | BL1202 | 1475283 | 1476215 | + | probable phosphoprotein phosphatase (ppp) | trembl|AL079308|SCH69__15 | 1.00E−23 |
| NO. 764 | BL1204 | 1477564 | 1481601 | complement | dna-directed rna polymerase beta prime chain (EC | swiss|P47769|RPOC__MYCTU | 0 |
| NO. 765 | BL1205 | 1481769 | 1485332 | complement | dna-directed rna polymerase beta chain (EC | gp|AL160431|7248348 | 0 |
| NO. 766 | BL1207 | 1486274 | 1487260 | complement | probable a/g-specific adenine glycosylase | trembl|AL049628|SCE94__6 | 2.00E−64 |
| NO. 767 | BL1208 | 1487434 | 1487943 | + | probable rna methyltransferase (EC 2.1.1.-) | trembl|AL009198|MTV004__21 | 2.00E−40 |
| NO. 768 | BL1209 | 1488250 | 1489614 | complement | narrowly conserved hypothetical protein with | tremblnew|AL162757|NMA6Z2491__172 | 5.00E−161 |
| NO. 769 | BL1210 | 1490105 | 1491355 | complement | galactokinase (EC 2.7.1.6) (galactose kinase) | swissnew|P96910|GAL1__MYCTU | 4.00E−62 |

TABLE I-continued

| | Gene Name | Start | Stop | Strand | Function | Best Hit | Best Score |
|---|---|---|---|---|---|---|---|
| NO. 770 | BL1211 | 1491372 | 1492622 | complement | galactose-1-phosphate uridylyltransferase (EC | trembl|AF135398|AF135398__6 | 1.00E−40 |
| NO. 771 | BL1212 | 1492615 | 1493511 | complement | probable deor-type transcriptional regulator. | swiss|O05261|YULB_BACSU | 9.00E−32 |
| NO. 772 | BL1213 | 1493920 | 1494936 | + | dihydroorotate dehydrogenase (EC 1.3.3.1) | swissnew|P74782|PYRD_SYNY3. | 3.00E−44 |
| NO. 773 | BL1214 | 1495104 | 1496219 | complement | probable nadh-dependent flavin oxidoreductase | tremblnew|AL445503|SC2G38__2 | 5.00E−96 |
| NO. 774 | BL1215 | 1496669 | 1498984 | complement | possible penicillin-binding protein | trembl|AL079353|SCH17__14 | 3.00E−67 |
| NO. 775 | BL1216 | 1499088 | 1499807 | complement | probable transcriptional regulator with cyclic | trembl|AL079353|SCH17__5 | 3.00E−50 |
| NO. 776 | BL1217 | 1500046 | 1501131 | complement | probable lipoate protein ligase (snoP) | trembl|AJ224512|SNO224512__16 | 3.00E−67 |
| NO. 777 | BL1218 | 1501189 | 1502220 | complement | 3-isopropylmalate dehydrogenase (EC 1.1.1.85) | swiss|P94631|LEU3_CORGL | 5.00E−114 |
| NO. 778 | BL1219 | 1502285 | 1504801 | complement | protease ii (EC 3.4.21.83) (oligopeptidase b) | trembl|Z80226|MTCY369__27 | 6.00E−94 |
| NO. 779 | BL1220 | 1504862 | 1506202 | complement | narrowly conserved hypothetical protein with | trembl|AE001968|AE001968__4 | 3.00E−21 |
| NO. 780 | BL1221 | 1506260 | 1506673 | complement | glycine cleavage system h protein (gcvH) | swissnew|O86566|GCSH_STRCO | 3.00E−27 |
| NO. 781 | BL1222 | 1506699 | 1507991 | complement | #NAME? | swissnew|O53345|NUDC_MYCTU | 1.00E−34 |
| NO. 782 | BL1224 | 1508984 | 1509616 | complement | narrowly conserved hypothetical protein with | emnew|AL353870|SC6F7 | 5.00E−50 |
| NO. 783 | BL1226 | 1509814 | 1510185 | + | thioredoxin (trxA2) | trembl|AL133422|SCM1__17 | 1.00E−26 |
| NO. 784 | BL1229 | 1513262 | 1514698 | complement | possible etk-like tyrosine kinase involved in | trembl|Z99122|BSUB0019__122 | 6.00E−32 |
| NO. 785 | BL1234 | 1517948 | 1519267 | + | hypothetical protein with similarity to abili: | trembl|U94520|LLU94520__1 | 3.00E−27 |
| NO. 786 | BL1239 | 1522841 | 1523209 | complement | hypothetical protein in the is21/is1162 | swissnew|Q99338|ISTB_BACTB | 2.00E−22 |
| NO. 787 | BL1244 | 1528511 | 1529758 | complement | dtdp-glucose 4,6-dehydratase (EC 4.2.1.46) | trembl|AF071085|AF071085__9 | 5.00E−121 |
| NO. 788 | BL1245 | 1529912 | 1531090 | + | probable udp-galactopyranose mutase (EC | trembl|AF026540|AF026540__1 | 5.00E−124 |
| NO. 789 | BL1247 | 1532596 | 1533474 | + | possible 2-hydroxyhepta-2,4-diene-1,7-dioate | trembl|AL031124|SC1C2__27 | 6.00E−53 |
| NO. 790 | BL1248 | 1533720 | 1534595 | complement | iclr-type transcriptional regulator | pironly|B83207|B83207 | 9.00E−26 |
| NO. 791 | BL1249 | 1534841 | 1536394 | + | histidine ammonia-lyase (EC 4.3.1.3) (histidase) | tremblnew|AL512667|SC2K31__9 | 5.00E−164 |
| NO. 792 | BL1250 | 1536613 | 1539282 | + | protease of clpa/clpb type (clpB) | trembl|AL049754|SCH10__39 | 0 |
| NO. 793 | BL1251 | 1539399 | 1540538 | + | probable glutamyl-trna synthetase (EC 6.1.1.17) | pironly|C81210|C81210 | 4.00E−45 |
| NO. 794 | BL1253 | 1541869 | 1542348 | complement | hypothetical protein with dufl 63 | trembl|D78193|BSGNTZA__15 | 1.00E−45 |
| NO. 795 | BL1254 | 1542396 | 1543022 | complement | uracil phosphoribosyltransferase (EC 2.4.2.9) | tremblnew|AP001519|AP001519__279 | 1.00E−52 |
| NO. 796 | BL1258 | 1545721 | 1546935 | complement | probable mutt1 protein (mutT1) | trembl|Z83018|MTCY349__36 | 1.00E−28 |
| NO. 797 | BL1259 | 1547078 | 1549315 | complement | polyphosphate kinase (EC 2.7.4.1) | gp|AL353816|7636018 | 0 |
| NO. 798 | BL1261 | 1551240 | 1552016 | complement | iclr-type transcriptional regulator | trembl|AL031124|SC1C2__33 | 3.00E−82 |
| NO. 799 | BL1262 | 1552334 | 1553737 | + | 3-isopropylmalate dehydratase large subunit (EC | trembl|AL031124|SC1C2__34 | 0 |
| NO. 800 | BL1263 | 1553820 | 1554512 | + | 3-isopropylmalate dehydratase small subunit (EC | swiss|O33124|LEUD_MYCLE | 9.00E−64 |
| NO. 801 | BL1266 | 1557876 | 1559222 | complement | nadh oxidase (EC 1.6.99.3) (noxase) (nox) | swiss|P37061|NAOX_ENTFA | 5.00E−120 |
| NO. 802 | BL1267 | 1559471 | 1560796 | + | udp-n-acetylglucosamine | trembl|AL138851|SCE59__8 | 5.00E−168 |
| NO. 803 | BL1268 | 1560845 | 1562098 | complement | probable aminotransferase | trembl|AL021428|MTV030__17 | 4.00E−62 |
| NO. 804 | BL1269 | 1562192 | 1563124 | complement | probable lysr-type transcriptional regulator | trembl|AL031317|SC6G4__44 | 5.00E−31 |
| NO. 805 | BL1270 | 1563211 | 1564476 | complement | hypothetical transmembrane protein possibly | trembl|AE001715|AE001715__5 | 5.00E−35 |
| NO. 806 | BL1272 | 1565364 | 1567226 | + | arginyl-trna synthetase (EC 6.1.1.19) | swiss|Q10609|SYR_MYCTU | 5.00E−149 |
| NO. 807 | BL1273 | 1567229 | 1568821 | + | probable diaminopimelate decarboxylase (EC | swiss|P31848|DCDA_MYCTU | 5.00E−74 |
| NO. 808 | BL1274 | 1568982 | 1570298 | + | homoserine dehydrogenase (EC 1.1.1.3) (hdh) | swiss|Q10601|DHOM_MYCTU | 5.00E−103 |
| NO. 809 | BL1275 | 1570405 | 1571517 | + | possible homoserine kinase (EC 2.7.1.39) (hk) | swissnew|P45836|KHSE_MYCU | 4.00E−33 |
| NO. 810 | BL1276 | 1571654 | 1573102 | + | hypothetical protein with mutt domain | tremblnew|AL512667|SC2K31__18 | 1.00E−31 |
| NO. 811 | BL1277 | 1573298 | 1574371 | + | atp-binding protein of abc transporter system | tremblnew|AL391754|SCK7__8 | 9.00E−60 |
| NO. 812 | BL1280 | 1576974 | 1578248 | + | succinyl-diaminopimelate desuccinylase (EC | trembl|Z93777|MTC1364__12 | 2.00E−75 |

TABLE I-continued

| | Gene Name | Start | Stop | Strand | Function | Best Hit | Best Score |
|---|---|---|---|---|---|---|---|
| NO. 813 | BL1281 | 1578585 | 1581596 | + | ribonuclease g (EC 3.1.4.-) (mase g) (rne) | trembl|AL139298|SCC88__10 | 5.00E−160 |
| NO. 814 | BL1282 | 1581748 | 1582056 | + | 50s ribosomal protein l21. (rpIU) | swiss|P71907|RL21__MYCTU | 3.00E−25 |
| NO. 815 | BL1283 | 1582079 | 1582327 | + | 50s ribosomal protein l27. (rpmA) | pironly|H82559|H82559 | 2.00E−27 |
| NO. 816 | BL1284 | 1582396 | 1584087 | + | gtp-binding protein (obg) | trembl|D87916|SGD916__3 | 5.00E−142 |
| NO. 817 | BL1285 | 1584088 | 1585221 | + | glutamate 5-kinase (EC 2.7.2.11) (gamma-glutamyl | trembl|AL136518|SCC123__25 | 5.00E−104 |
| NO. 818 | BL1286 | 1585312 | 1586517 | + | aspartate aminotransferase ec 2.6.1.1 (aspC) | gp|AL160431|7248339 | 5.00E−139 |
| NO. 819 | BL1288 | 1587018 | 1587911 | + | probable transcription antitermination protein | gp|AL160431|7248341 | 3.00E−49 |
| NO. 820 | BL1290 | 1588174 | 1588605 | + | 50s ribosomal protein l11 (rpIK) | trembl|AF130462|AF130462__4 | 9.00E−54 |
| NO. 821 | BL1291 | 1588621 | 1589313 | + | 50s ribosomal protein l1 (rlpA) | gp|AL160431|7248343 | 6.00E−84 |
| NO. 822 | BL1292 | 1595385 | 1596212 | complement | morphine 6-dehydrogenase (EC 1.1.1.218) | trembl|AF008220|AF008220__185 | 3.00E−78 |
| NO. 823 | BL1293 | 1596344 | 1597795 | + | xylulose kinase (EC 2.7.1.17) (xylulokinase) | swiss|P21939|XYLB__LACPE | 1.00E−54 |
| NO. 824 | BL1295 | 1598185 | 1599600 | + | histidinol dehydrogenase (EC 1.1.1.23) (hdh) | swissnew|P28736|HISX__MYCSM | 5.00E−130 |
| NO. 825 | BL1296 | 1599597 | 1600757 | + | histidinol-phosphate aminotransferase (EC | swissnew|P16246|HIS8__STRCO | 5.00E−93 |
| NO. 826 | BL1297 | 1600843 | 1601442 | + | imidazoleglycerol-phosphate dehydratase (EC | swiss|O06590|HIS7__MYCTU | 4.00E−65 |
| NO. 827 | BL1299 | 1602271 | 1602918 | + | amidotransferase hish (EC 2.4.2.-) (hisH) | swissnew|P16249|HIS5__STRCO | 1.00E−60 |
| NO. 828 | BL1300 | 1602988 | 1603713 | + | phosphoribosylformimino-5-aminoimidazole | swissnew|P16250|HIS4__STRCO | 8.00E−84 |
| NO. 829 | BL1301 | 1603817 | 1605250 | complement | narrowly conserved hypothetical protein with | trembl|AL031232|SC10H5__7 | 5.00E−100 |
| NO. 830 | BL1302 | 1605399 | 1606736 | + | glutamine synthetase (glutamate-ammonia ligase) | trembl|AL136500|SC1G2__3 | 0 |
| NO. 831 | BL1305 | 1608481 | 1612689 | complement | atp-dependent helicase (hrpA) | trembl|AL118514|SCD25__28 | 0 |
| NO. 832 | BL1306 | 1612607 | 1613263 | complement | conserved hypothetical protein possibly in | swissnew|P37872|YBXB__BACSU | 4.00E−31 |
| NO. 833 | BL1307 | 1613422 | 1614927 | + | gtp-binding protein (hflX) | trembl|AL022268|SC4H2__17 | 5.00E−134 |
| NO. 834 | BL1308 | 1615087 | 1616070 | + | lactate dehydrogenase (EC 1.1.1.27) (ldh) | swiss|P19869|LDH__BIFLO | 0 |
| NO. 835 | BL1309 | 1616212 | 1617150 | complement | probable cation efflux protein | trembl|AL049587|SC5F2A__34 | 2.00E−57 |
| NO. 836 | BL1310 | 1617316 | 1618041 | complement | lexa repressor (EC 3.4.21.88) (sos regulatory | trembl|AJ224870|SCAJ4870__2 | 3.00E−62 |
| NO. 837 | BL1312 | 1618559 | 1619035 | + | hypothetical protein with high similarity to | trembl|AJ224870|SCAJ4870__3 | 3.00E−52 |
| NO. 838 | BL1313 | 1619170 | 1620369 | complement | d-3-phosphoglycerate dehydrogenase (EC 1.1.1.95) | pironly|C82072|C82072 | 5.00E−111 |
| NO. 839 | BL1314 | 1620380 | 1622659 | complement | narrowly conserved hypothetical protein with | trembl|AL138978|SC6A11__15 | 5.00E−126 |
| NO. 840 | BL1315 | 1622992 | 1623513 | + | conserved hypothetical protein in upf0040 | tremblnew|AP001516|AP001516__5 | 2.00E−30 |
| NO. 841 | BL1316 | 1623513 | 1624592 | + | widely conserved hypothetical protein in | trembl|AL109663|SC4A10__25 | 3.00E−79 |
| NO. 842 | BL1317 | 1625045 | 1626847 | + | peptidoglycan synthetase. penicillin-binding | trembl|AL109663|SC4A10__23 | 3.00E−84 |
| NO. 843 | BL1319 | 1627795 | 1629246 | + | udp-n-acetylmuramoylalanyl-d-glutamyl-2,6-diaminopimelate-d-alanyl-d- | trnembl|AL109663|SC4A10__21 | 2.00E−82 |
| NO. 844 | BL1320 | 1629291 | 1630397 | + | phospho-n-acetylmuramoyl-pentapeptide-transferase | swiss|P56833|MRAY__STRCO | 3.00E−87 |
| NO. 845 | BL1321 | 1630452 | 1631897 | + | udp-n-acetylmuramoylalanine-d-glutamate ligase | trembl|AL109663|SC4A10__19 | 5.00E−88 |
| NO. 846 | BL1322 | 1631884 | 1633101 | + | probable ftsw-like protein (fstW) | trembl|U10879|SC10879__2 | 7.00E−47 |
| NO. 847 | BL1323 | 1633117 | 1634298 | + | udp-n-acetylglucosamine-n-acetylmuramyl-(pentapeptide) | swissnew|Q9ZBA5|MURG__STRCO | 2.00E−87 |
| NO. 848 | BL1324 | 1634399 | 1635937 | + | udp-n-acetylmuramate-alanine ligase (EC | swiss|Q9X827|MURC__STRCO | 5.00E−80 |
| NO. 849 | BL1325 | 1638253 | 1638537 | complement | narrowly conserved hypothetical protein with | pironly|F82517|F82517 | 1.00E−20 |
| NO. 850 | BL1326 | 1639341 | 1639817 | + | conserved hypothetical protein with unknown | trembl|X72832|SEDEXB__5. | 6.00E−34 |
| NO. 851 | BL1327 | 1639978 | 1643097 | + | alpha-mannosidase (EC 3.2.1.24) | trembl|AL133278|SCM11__3 | 0 |
| NO. 852 | BL1328 | 1643228 | 1646368 | + | alpha-mannosidase (EC 3.2.1.24) | trembl|AL133278|SCM11__3 | 0 |
| NO. 853 | BL1329 | 1646638 | 1649742 | + | alpha-mannosidase (EC 3.2.1.24) | trembl|AL133278|SCM11__3 | 0 |
| NO. 854 | BL1330 | 1649938 | 1651209 | + | probable solute-binding protein of abc | trembl|AL133278|SCM11__7 | 3.00E−91 |
| NO. 855 | BL1331 | 1651212 | 1652150 | + | probable sugar permease of abc transporter | trembl|AL133278|SCM11__6 | 9.00E−74 |

TABLE I-continued

| | Gene Name | Start | Stop | Strand | Function | Best Hit | Best Score |
|---|---|---|---|---|---|---|---|
| NO. 856 | BL1332 | 1652150 | 1653007 | + | probable sugar permease of abc transporter | trembl|AL133278|SCM11_5 | 1.00E−73 |
| NO. 857 | BL1333 | 1653021 | 1654310 | + | narrowly conserved hypothetical protein with | trembl|AL133278|SCM11_4 | 5.00E−101 |
| NO. 858 | BL1334 | 1654435 | 1657077 | + | probable pentosidase or hexosidase | tremblnew|AL512980|SSOLP2N19_30 | 9.00E−45 |
| NO. 859 | BL1335 | 1657125 | 1659938 | + | probable endo-beta-n-acetylglucosaminidase; | tremblnew|AP001509|AP001509_223 | 5.00E−177 |
| NO. 860 | BL1336 | 1660234 | 1661340 | + | probable laci-type transcriptional regulator | trembl|AL133278|SCM11_8 | 2.00E−59 |
| NO. 861 | BL1337 | 1661462 | 1662760 | complement | narrowly conserved hypothetical protein with | swiss|P32140|YIHS_ECOLI | 7.00E−83 |
| NO. 862 | BL1338 | 1662764 | 1664062 | complement | narrowly conserved hypothetical protein with | tremblnew|AP001509|AP001509_228 | 5.00E−108 |
| NO. 863 | BL1340 | 1665242 | 1666456 | complement | probable transcriptional repressor in the rok | trembl|AL009199|SC7B7_5 | 7.00E−42 |
| NO. 864 | BL1341 | 1666683 | 1667597 | + | possible sugar kinase | swiss|P54495|GLK_BACSU | 2.00E−32 |
| NO. 865 | BL1342 | 1667747 | 1668871 | complement | nagc/xlyr-type transcriptional regulator | tremblnew|AP001516|AP001516_187 | 2.00E−33 |
| NO. 866 | BL1343 | 1669209 | 1670021 | + | glucosamine-6-phosphate isomerase 1 (EC | swiss|O31458|YBFT_BACSU | 7.00E−49 |
| NO. 867 | BL1344 | 1670077 | 1671360 | + | n-acetylglucosamine-6-phosphate deacetylase (EC | trembl|AL021841|MTV016_30 | 8.00E−55 |
| NO. 868 | BL1345 | 1671640 | 1673274 | + | probable solute-binding protein of abc | trembl|AL132648|SCI41_38 | 2.00E−89 |
| NO. 869 | BL1346 | 1673439 | 1674530 | + | probable permease of abc transporter for | trembl|AE001772|AE001772_4 | 2.00E−76 |
| NO. 870 | BL1347 | 1674649 | 1675701 | + | probable permease of abc transporter for | trembl|AE000980|AE000980_2 | 1.00E−58 |
| NO. 871 | BL1348 | 1675705 | 1677414 | + | atp binding protein of abc transporter | trembl|D90720|ECD720_13 | 5.00E−124 |
| NO. 872 | BL1349 | 1677464 | 1677985 | complement | hypothetical protein containing mutt-like | tremblnew|AL445963|SC2G2_26 | 3.00E−32 |
| NO. 873 | BL1350 | 1678034 | 1679629 | complement | xaa-pro aminopeptidase i (EC 3.4.11.9) (x-pro | swiss|Q05813|AMP1_STRLI | 5.00E−110 |
| NO. 874 | BL1353 | 1682038 | 1683627 | + | folylpolyglutamate synthase ec 6.3.2.17 (folC or | trembl|AL139298|SCC88_25 | 5.00E−104 |
| NO. 875 | BL1354 | 1683688 | 1687365 | + | chromosome partitioning protein smc (smc) | trembl|AL034447|SC7A1_21 | 0 |
| NO. 876 | BL1356 | 1688601 | 1690154 | complement | udp-n-acetylmuramoylalanyl-d-glutamate-2,6-diaminopimelate | swiss|O69557|MURE_MYCLE | 6.00E−39 |
| NO. 877 | BL1357 | 1690272 | 1691081 | + | rna polymerase sigma-e factor (sigma-24) (sigH) | trembl|AF144091|AF144091_4 | 6.00E−37 |
| NO. 878 | BL1359 | 1691667 | 1692611 | complement | hypothetical protein with possible | tremblnew|AE005619|AE005619_2 | 8.00E−30 |
| NO. 879 | BL1360 | 1692736 | 1693692 | complement | hypothetical protein in aldose epimerase family | tremblnew|AE005619|AE005619_2 | 4.00E−24 |
| NO. 880 | BL1361 | 1693917 | 1694975 | + | lytb protein involved with rela and the | swissnew|O53458|LYB1_MYCTU | 9.00E−89 |
| NO. 881 | BL1362 | 1695015 | 1695452 | complement | conserved hypothetical protein very similar to | trembl|AL096884|SC4G6_27 | 1.00E−33 |
| NO. 882 | BL1363 | 1695618 | 1696676 | complement | glyceraldehyde 3-phosphate dehydrogenase c (EC | trembl|AJ000339|LDGAPPGK_2 | 5.00E−120 |
| NO. 883 | BL1366 | 1699250 | 1699885 | + | translation initiation factor if-3 (infC) | swiss|O88060|IF3_STRCO | 2.00E−48 |
| NO. 884 | BL1367 | 1700113 | 1700496 | + | 50s ribosomal protein l20. (rplT) | swiss|O88058|RL20_STRCO | 4.00E−50 |
| NO. 885 | BL1368 | 1700611 | 1701537 | + | probable integrase/recombinase | trembl|Z98268|MTCI125_22 | 5.00E−70 |
| NO. 886 | BL1369 | 1701665 | 1704511 | + | large protein with n-terminal similarity to atp | trembl|U73183|U73183_1 | 5.00E−111 |
| NO. 887 | BL1370 | 1704713 | 1705612 | + | widely conserved hypothetical protein in para | trembl|AL109848|SCI51_12 | 2.00E−86 |
| NO. 888 | BL1371 | 1705631 | 1706545 | + | narrowly conserved hypothetical protein with | trembl|Z98268|MTCI125_30 | 5.00E−42 |
| NO. 889 | BL1372 | 1706558 | 1707274 | + | conserved hypothetical protein with unknown | trembl|AL109848|SCI51_9 | 6.00E−46 |
| NO. 890 | BL1373 | 1707406 | 1708233 | + | narrowly conserved hypothetical protein possibly | trembl|D90913|SSD913_123 | 1.00E−30 |
| NO. 891 | BL1374 | 1708294 | 1709574 | + | quinolinate synthetase (nadA) | tremblnew|AP001511|AP001511_109 | 5.00E−104 |
| NO. 892 | BL1375 | 1709662 | 1711293 | + | l-aspartate oxidase (EC 1.4.3.16) (quinolinate | trembl|AL049628|SCE94_33 | 2.00E−94 |
| NO. 893 | BL1376 | 1711297 | 1712190 | + | probable nicotinate-nucleotide pyrophosphorylase | tremblnew|AX064321|AX064321_1 | 7.00E−77 |
| NO. 894 | BL1377 | 1712193 | 1713440 | + | possible pyridoxal-phosphate-dependent | trembl|AL031184|SC2A11_20 | 5.00E−72 |
| NO. 895 | BL1378 | 1713472 | 1714821 | + | probable sugar transporter | tremblnew|AX066931|AX066931_1 | 5.00E−127 |

TABLE I-continued

| | Gene Name | Start | Stop | Strand | Function | Best Hit | Best Score |
|---|---|---|---|---|---|---|---|
| NO. 896 | BL1379 | 1715136 | 1717067 | + | widely conserved protein similar to those | trembl|Z95584|MTCI65__32 | 0 |
| NO. 897 | BL1381 | 1717693 | 1718670 | + | probable chorismate mutase (EC 5.4.99.5) (cm); | embl|AE000889|AE000889 | 6.00E−22 |
| NO. 898 | BL1382 | 1718664 | 1719731 | + | probable prephenate dehydrogenase ec1.3.1.12 | trembl|AE001962|AE001962__4 | 1.00E−30 |
| NO. 899 | BL1384 | 1720235 | 1721308 | + | probable integrase/recombinase protein similar | trembl|Z97369|MLCB250__29 | 3.00E−59 |
| NO. 900 | BL1386 | 1721561 | 1723201 | + | solute binding protein of abc transporter system | trembl|AL022121|MTV025__15 | 5.00E−114 |
| NO. 901 | BL1387 | 1723502 | 1724428 | + | probable permease protein of abc-transporter for | trembl|AL022121|MTV025__14 | 5.00E−71 |
| NO. 902 | BL1389 | 1724447 | 1725451 | + | probable permease protein of abc-transporter for | trembl|AL022121|MTV025__13 | 1.00E−77 |
| NO. 903 | BL1390 | 1725474 | 1727483 | + | probable atp binding protein of abc transporter | trembl|AL022121|MTV025__12 | 5.00E−135 |
| NO. 904 | BL1391 | 1727588 | 1728448 | + | possible exodeoxyribonuclease (EC 3.1.11.2) | trembl|AL132674|SCE87__25 | 2.00E−58 |
| NO. 905 | BL1392 | 1728516 | 1729370 | + | narrowly conserved hypothetical protein with | trembl|AL021530|SC2E9__10 | 1.00E−24 |
| NO. 906 | BL1394 | 1730095 | 1731402 | + | conserved hypothetical protein with duf90 | trembl|AL021529|SC10A5__6 | 1.00E−50 |
| NO. 907 | BL1396 | 1732200 | 1734713 | + | probable cation-transporting atpase (EC 3.6.1) | trembl|AL035654|SCE8__9 | 5.00E−159 |
| NO. 908 | BL1397 | 1734834 | 1737533 | + | aconitate hydratase (EC 4.2.1.3) (citrate | trembl|AL021184|MTV007__22 | 0 |
| NO. 909 | BL1402 | 1741470 | 1742195 | complement | response regulator of two-component system | trembl|AL132824|SCAH10__19 | 5.00E−35 |
| NO. 910 | BL1403 | 1742230 | 1743498 | complement | atypical histidine kinase sensor of | trembl|AL132824|SCAH10__18 | 5.00E−20 |
| NO. 911 | BL1405 | 1744823 | 1745722 | + | conserved hypothetical protein with mutt type | tremblnew|AE005259|AE005259__8 | 1.00E−31 |
| NO. 912 | BL1406 | 1745862 | 1746878 | + | possible integral membrane protein with duf6 | pironly|B83194|B83194 | 6.00E−42 |
| NO. 913 | BL1407 | 1746911 | 1747753 | complement | narrowly conserved hypothetical protein with | tremblnew|AP001513|AP001513__158 | 2.00E−43 |
| NO. 914 | BL1408 | 1747795 | 1749237 | + | widely conserved hypothetical protein in | trembl|AL022268|SC4H2__8 | 5.00E−152 |
| NO. 915 | BL1409 | 1749248 | 1750234 | + | trna delta(2)-isopentenylpyrophosphate | swissnew|O69967|MIAA__STRCO | 4.00E−78 |
| NO. 916 | BL1411 | 1751229 | 1754138 | + | cell division protein ftsk (ftsK) | trembl|AL031031|SC7C7__5 | 0 |
| NO. 917 | BL1412 | 1754291 | 1754950 | + | cdp-diacylglycerol-glycerol-3-phosphate | trembl|U00019|ML019__22 | 1.00E−27 |
| NO. 918 | BL1415 | 1756716 | 1757909 | + | reca protein (recombinase a) (recA) | swissnew|Q9S660|RECA__BIFBR | 0 |
| NO. 919 | BL1416 | 1757912 | 1758505 | + | recx-like protein | embl|AF094756|AF094756 | 1.00E−81 |
| NO. 920 | BL1417 | 1758685 | 1759251 | + | hypothetical protein with unknown function | embl|AF094756|AF094756 | 4.00E−36 |
| NO. 921 | BL1418 | 1759382 | 1760044 | + | hypothetical protein in sigma 54 modulation | trembl|Z95121|MTY20BI1__16 | 4.00E−33 |
| NO. 922 | BL1419 | 1760206 | 1763100 | + | preprotein translocase seca subunit (secA) | swissnew|P55021|SECA__STRCO | 0 |
| NO. 923 | BL1422 | 1764354 | 1765400 | + | anthranilate phosphoribosyltransferase 1 (EC | swiss|O68608|TRD1__STRCO | 4.00E−75 |
| NO. 924 | BL1424 | 1766545 | 1767249 | + | widely conserved hypothetical protein with acyl | trembl|AL157956|SCL24__2 | 5.00E−58 |
| NO. 925 | BL1425 | 1767301 | 1769574 | complement | probable serine-threonine protein kinase | trembl|AL109661|SC6E10__4 | 4.00E−59 |
| NO. 926 | BL1426 | 1769718 | 1770836 | complement | probably bifunctional short chain isoprenyl | trembl|AL021957|MTV021__7 | 9.00E−30 |
| NO. 927 | BL1428 | 1771872 | 1773296 | + | rna polymerase principal sigma factor, sigma 70 | trembl|M90411|SAHRDB__1 | 5.00E−143 |
| NO. 928 | BL1429 | 1773354 | 1775672 | + | dna gyrase subunit b, (EC 5.99.1.3) (gyrB) | trembl|AL022374|SC5B8__12 | 0 |
| NO. 929 | BL1431 | 1777139 | 1778101 | + | probable ribokinase (EC 2.7.1.15) | pironly|B83403|B83403 | 5.00E−50 |
| NO. 930 | BL1432 | 1778117 | 1782850 | + | atp-dependent helicase ii (1 hr) | trembl|AL031031|SC7C7__16 | 0 |
| NO. 931 | BL1434 | 1783794 | 1786523 | complement | dna gyrase subunit a (EC 5.99.1.3) (gyrA) | trembl|AL009204|SC9B10__3 | 0 |
| NO. 932 | BL1435 | 1786753 | 1788042 | + | narrowly conserved hypothetical protein with | trembl|AL009204|SC9B10__11 | 3.00E−48 |
| NO. 933 | BL1438 | 1789595 | 1790071 | + | deoxyuridine 5'-triphosphate nucleotidohydrolase | swiss|O54134|DUT__STRCO | 4.00E−42 |
| NO. 934 | BL1439 | 1790184 | 1792529 | + | gtp pyrophosphokinase (EC 2.7.6.5) (atp:gtp | swissnew|P52560|RELA__STRCO | 0 |
| NO. 935 | BL1440 | 1792647 | 1793531 | complement | is3-type transposase | tremblnew|AE000433|ECAE433__4 | 9.00E−48 |
| NO. 936 | BL1442 | 1794113 | 1794661 | complement | possible peptidyl-prolyl cis-trans isomerase | tyembl|U64692|SCU64692__1 | 6.00E−48 |

TABLE I-continued

| | Gene Name | Start | Stop | Strand | Function | Best Hit | Best Score |
|---|---|---|---|---|---|---|---|
| NO. 937 | BL1444 | 1796077 | 1797012 | complement | widely conserved hypothetical transmembrane | trembl|AP000002|AP000002__291 | 3.00E−23 |
| NO. 938 | BL1447 | 1799086 | 1799931 | + | possible phosphoglycerate mutase | trembl|Z81368|MTCY253__35 | 2.00E−22 |
| NO. 939 | BL1448 | 1800046 | 1800996 | + | possible magnesium and cobalt transport protein | trembl|AE002075|AE002075__11 | 1.00E−61 |
| NO. 940 | BL1449 | 1801011 | 1801937 | + | solute binding protein of abc transporter | trembl|AL020958|SC4H8__15 | 1.00E−32 |
| NO. 941 | BL1450 | 1801980 | 1804943 | + | leucyl-trna synthetase (EC 6.1.1.4) | trembl|AL136518|SCC123__9 | 0 |
| NO. 942 | BL1452 | 1805946 | 1807634 | + | conserved hypothetical transmembrane protein | trembl|AL136518|SCC123__5 | 3.00E−26 |
| NO. 943 | BL1453 | 1807774 | 1809120 | + | possible prolidase ec 3.4.13.9 (x-pro | tremblnew|AP001517|AP001517__57 | 2.00E−37 |
| NO. 944 | BL1454 | 1809283 | 1810158 | + | hypothetical protein with possible dna binding | trembl|AL136518|SCC123__2 | 2.00E−35 |
| NO. 945 | BL1457 | 1812256 | 1813299 | + | metalloendopeptidase gcp (gcp) | swiss|O86793|GCP__STRCO | 9.00E−98 |
| NO. 946 | BL1458 | 1813966 | 1814901 | + | probable integrase/recombinse | trembl|Z80225|MTCY441__16 | 3.00E−25 |
| NO. 947 | BL1467 | 1822821 | 1824281 | complement | possible trag-related protein | tremblnew|AL391754|SCK7__2 | 3.00E−22 |
| NO. 948 | BL1469 | 1825372 | 1828008 | + | dna topoisomerase iii (topb) (EC 5.99.1.2) | trembl|AB001488|BSAB1488__10 | 9.00E−87 |
| NO. 949 | BL1472 | 1829232 | 1830500 | complement | type ii restriction enzyme very similar to | trembl|AJ224995|ECO224995__1 | 8.00E−37 |
| NO. 950 | BL1473 | 1830546 | 1831517 | complement | modification methylase very similar to ecorii | swissnew|P24581|MTNX__NEILA | 3.00E−84 |
| NO. 951 | BL1476 | 1833873 | 1835348 | complement | conserved hypothetical protein with unknown | swiss|P55564|Y4ME__RHISN | 6.00E−36 |
| NO. 952 | BL1479 | 1837643 | 1839451 | complement | narrowly conserved hypothetical protein similar | trembl|AL049645|SCE2__7 | 2.00E−59 |
| NO. 953 | BL1483 | 1842269 | 1843783 | complement | narrowly conserved hypothetical protein with | tremblnew|AP001204|AP001204__38 | 3.00E−56 |
| NO. 954 | BL1484 | 1843882 | 1845369 | complement | narrowly conserved hypothetical protein with | tremblnew|AP001204|AP001204__39 | 9.00E−50 |
| NO. 955 | BL1489 | 1858431 | 1863242 | complement | hypothetical protein with limited similarity to | trembl|M64978|PPPRGAB__4 | 5.00E−28 |
| NO. 956 | BL1492 | 1866104 | 1866697 | complement | hypothetical protein with similarity to the par | tremblnew|AF121000|AF121000__7 | 8.00E−29 |
| NO. 957 | BL1497 | 1871350 | 1872039 | + | narrowly conserved hypothetical protein in | swiss|Q10812|YS91__MYCTU | 3.00E−20 |
| NO. 958 | BL1499 | 1873997 | 1875217 | complement | isocitrate dehydrogenase [nadp] (EC 1.1.1.42) | swiss|O53389|IDH__MYCTU | 5.00E−179 |
| NO. 959 | BL1500 | 1875345 | 1876469 | + | inosine-5′-monophosphate dehydrogenase (guaB) | gp|AL161755|7320890 | 5.00E−147 |
| NO. 960 | BL1501 | 1877213 | 1879300 | + | possible long-chain-fatty acid coa ligase | trembl|AL021957|MTV021__21 | 5.00E−118 |
| NO. 961 | BL1502 | 1879307 | 1879795 | + | polypeptide deformylase (EC 3.5.1.31) (pdf) | swiss|Q9XAQ2|DEF__STRCO | 2.00E−29 |
| NO. 962 | BL1503 | 1880107 | 1880997 | + | 30s ribosomal protein s2. (rpsB) | trembl|AL023797|SC2E1__41 | 1.00E−94 |
| NO. 963 | BL1504 | 1881076 | 1881927 | + | elongation factor ts (ef-ts) (tsf) | swiss|O31213|EFTS__STRCO | 1.00E−49 |
| NO. 964 | BL1505 | 1882101 | 1882841 | + | uridylate kinase (EC 2.7.4.-) (uk) (uridine | trembl|AL023797|SC2E1__43 | 6.00E−82 |
| NO. 965 | BL1506 | 1882918 | 1883469 | + | ribosome recycling factor (ribosome releasing | swiss|O86770|RRF__STRCO | 5.00E−55 |
| NO. 966 | BL1507 | 1883492 | 1884478 | + | probable phosphatidate cytidylyltransferase (EC | trembl|AL031035|SC6A9__39 | 3.00E−29 |
| NO. 967 | BL1508 | 1884689 | 1885858 | + | widely conserved hypothetical protein with | trembl|AL031035|SC6A9__22 | 5.00E−115 |
| NO. 968 | BL1509 | 1885859 | 1886407 | complement | hypothetical protein in the thij/pfpi family | pironly|D83125|D83125 | 3.00E−37 |
| NO. 969 | BL1510 | 1886616 | 1887800 | + | transpsosase in is256 family | swiss|Q52873|TRA5__RHIME | 5.00E−61 |
| NO. 970 | BL1512 | 1889585 | 1890166 | complement | deoxycytidine triphosphate deaminase (EC | swissnew|Q9X8W0|DCD__STRCO | 5.00E−72 |
| NO. 971 | BL1515 | 1892320 | 1893174 | + | widely conserved hypothetical transmembrane | tremblnew|AP001518|AP001518__285 | 2.00E−20 |
| NO. 972 | BL1516 | 1893218 | 1895290 | complement | probable nhap-type na(+)/h(+) exchanger | trembl|Z99121|BSUB0018__28 | 2.00E−76 |
| NO. 973 | BL1517 | 1895390 | 1895866 | + | possible cytidine and deoxycytidylate deaminase | trembl|AL022121|MTV025__101 | 1.00E−37 |
| NO. 974 | BL1518 | 1895986 | 1898292 | + | alpha-galactosidase (EC 3.2.1.22) (melibiase) | trembl|AF124596|AF124596__1 | 0 |
| NO. 975 | BL1520 | 1898457 | 1899665 | complement | possible nagc/xylr-tpye transcriptional | tremblnew|AL449216|SC35B7__12 | 8.00E−49 |
| NO. 976 | BL1521 | 1899839 | 1901128 | + | sugar binding protein of abc transporter system | swiss|Q00749|MSME__STRMU | 5.00E−28 |
| NO. 977 | BL1522 | 1901150 | 1902079 | + | sugar permease of abc transporter system | swiss|Q00750|MSMF__STRMU | 2.00E−50 |

TABLE I-continued

| | Gene Name | Start | Stop | Strand | Function | Best Hit | Best Score |
|---|---|---|---|---|---|---|---|
| NO. 978 | BL1523 | 1902098 | 1902964 | + | sugar permease of abc transporter system | swiss|Q00751|MSMG_STRMU | 6.00E−48 |
| NO. 979 | BL1526 | 1904380 | 1906200 | + | oligo-1,6-glucosidase (EC 3.2.1.10) | swiss|P29094|O16G_BACTR | 5.00E−168 |
| NO. 980 | BL1527 | 1906486 | 1907733 | + | catabolic threonine dehydratase (tdcB) | tremblnew|AL451182|SCK13_16 | 2.00E−87 |
| NO. 981 | BL1528 | 1907879 | 1908529 | complement | sir2-type regulatory protein | trembl|AE001726|AE001726_9 | 4.00E−31 |
| NO. 982 | BL1530 | 1915778 | 1916530 | + | probable iclr-type transcriptional regulator | trembl|AL078635|CZA382_19 | 2.00E−20 |
| NO. 983 | BL1531 | 1916637 | 1917503 | complement | narrowly conserved hypothetical protein with | trembl|AL133423|SC4A7_14 | 7.00E−24 |
| NO. 984 | BL1535 | 1921809 | 1923773 | + | acetyl-/propionyl-coenzyme a carboxylase alpha | trembl|AF126429|AF126429_1 | 5.00E−131 |
| NO. 985 | BL1536 | 1923766 | 1925388 | + | propionyl-coa carboxylase beta chain (EC | tremblnew|AL512667|SC2K31_15 | 5.00E−153 |
| NO. 986 | BL1537 | 1925427 | 1934945 | + | type i multifunctional fatty acid synthase | trembl|X87822|MAFASGEN_1 | 0 |
| NO. 987 | BL1542 | 1942976 | 1944082 | complement | transpsosase in is30 family | trembl|AF189147|AF189147_1 | 4.00E−45 |
| NO. 988 | BL1543 | 1944703 | 1947231 | + | endo-1,4-beta-xylanase d (EC 3.2.1.8) | trembl|Z99113|BSUB0010_109 | 5.00E−128 |
| NO. 989 | BL1544 | 1947454 | 1950330 | + | possible extracellular exo-xylanase (EC 3.2.1.8) | trembl|AF005383|AF005383_5 | 3.00E−95 |
| NO. 990 | BL1546 | 1952294 | 1955035 | + | polyribonucleotide nucleotidyltransferase (EC | pironly|T10932|T10932 | 0 |
| NO. 991 | BL1547 | 1955462 | 1956856 | complement | widely conserved hypothetical protein with | pironly|B82096|B82096 | 3.00E−90 |
| NO. 992 | BL1549 | 1958210 | 1958731 | + | 50s ribosomal protein l10 (rpIJ) | swiss|P36257|RL10_STRGR | 6.00E−48 |
| NO. 993 | BL1550 | 1958840 | 1959220 | + | 50s ribosomal protein l7/l12 (rpIL) | trembl|D50624|SVVBRA1_8 | 2.00E−20 |
| NO. 994 | BL1555 | 1966051 | 1966800 | complement | hypothetical protein in the | trembl|AL132674|SCE87_33 | 2.00E−23 |
| NO. 995 | BL1556 | 1966827 | 1967522 | + | possible acetytransferase | embl|AL132674|SCE87 | 9.00E−27 |
| NO. 996 | BL1558 | 1969200 | 1969493 | + | groes (groES) | trembl|AF071828|AF071828_1 | 1.00E−30 |
| NO. 997 | BL1559 | 1970167 | 1971690 | complement | possible cystathionine gamma lyase (EC | trembl|U93874|BSU93874_2 | 8.00E−70 |
| NO. 998 | BL1561 | 1972567 | 1973667 | + | udp-n-acetylenolpyruvoylglucosamine reductase | gp|AL160431|7248337 | 2.00E−55 |
| NO. 999 | BL1562 | 1973819 | 1975345 | + | possible cationic amino acid transporter | trembl|Z95121|MTY20B11_28 | 5.00E−125 |
| NO. 1000 | BL1563 | 1975406 | 1975726 | + | ferredoxin (fdxC) | trembl|AL391751|SC9E12_20 | 2.00E−42 |
| NO. 1001 | BL1564 | 1975841 | 1977076 | + | probable aminotransferase (EC 2.6.1.-) | trembl|AL010186|MTV005_13 | 2.00E−61 |
| NO. 1002 | BL1565 | 1977103 | 1978449 | complement | dna-damage-inducible protein p. | tremblnew|AL162756|NMA5Z2491_212 | 7.00E−47 |
| NO. 1003 | BL1566 | 1978489 | 1979553 | + | conserved hypothetical transmembrane protein | pironly|A83476|A83476 | 5.00E−24 |
| NO. 1004 | BL1567 | 1980088 | 1981431 | + | narrowly conserved hypothetical protein with | trembl|AL133469|SCM10_29 | 6.00E−42 |
| NO. 1005 | BL1568 | 1981505 | 1982521 | + | possible 2-hydroxyacid dehydrogenase | trembl|AL133236|SCE65_14 | 1.00E−34 |
| NO. 1006 | BL1569 | 1982700 | 1983224 | + | conserved hypothetical protein in upf 0029 | tremblnew|AE005615|AE005615_10 | 5.00E−23 |
| NO. 1007 | BL1570 | 1984143 | 1986308 | + | 4-alpha-glucanotransferase (EC 2.4.1.25) | swiss|O53932|MALQ_MYCTU | 5.00E−150 |
| NO. 1008 | BL1571 | 1986706 | 1987155 | + | 50s ribosomal protein l13 | swiss|Q53874|RL13_STRCO | 2.00E−47 |
| NO. 1009 | BL1572 | 1987178 | 1987669 | + | 30s ribosomal protein s9 (rpsI) | swiss|Q53875|RS9_STRCO | 5.00E−46 |
| NO. 1010 | BL1573 | 1987760 | 1990300 | complement | family 13 glycosyl hydrolase | trembl|AL157916|SC3D11_13 | 5.00E−133 |
| NO. 1011 | BL1574 | 1990297 | 1991490 | complement | probable repressor in the rok (nagc/xylr) | tremblnew|AP001509|AP001509_138 | 3.00E−20 |
| NO. 1012 | BL1575 | 1992005 | 1994734 | + | aldehyde-alcohol dehydrogenase 2 [includes: | swissnew|Q24803|ADH2_ENTHI | 0 |
| NO. 1013 | BL1577 | 1996328 | 1996636 | + | 30s ribosomal protein s10 (rpsJ) | gp|AL161803|7321291 | 1.00E−37 |
| NO. 1014 | BL1578 | 1996653 | 1997294 | + | 50s ribosomal protein l3 (rplC) | gp|AL161803|7321292 | 2.00E−72 |
| NO. 1015 | BL1579 | 1997301 | 1997957 | + | 50s ribosomal protein l4. (rplD) | gp|AL161803|7321293 | 3.00E−58 |
| NO. 1016 | BL1580 | 1997963 | 1998259 | + | 50s ribosomal protein l23. (rplW) | gp|AL161803|7321294 | 2.00E−30 |
| NO. 1017 | BL1581 | 1998296 | 1999126 | + | 50s ribosomal protein l2. (rplB) | swiss|P95052|RL2_MYCTU | 5.00E−116 |
| NO. 1018 | BL1582 | 1999142 | 1999420 | + | 30s ribosomal protein s19 (rpsS) | swiss|O32985|RS19_MYCLE | 2.00E−42 |
| NO. 1019 | BL1583 | 1999437 | 1999796 | + | 50s ribosomal protein l22 (rplV) | gp|AL161803|7321297 | 1.00E−34 |
| NO. 1020 | BL1584 | 1999799 | 2000602 | + | 30s ribosomal protein s3 (rpsC) | gp|AL161803|7321298 | 2.00E−91 |
| NO. 1021 | BL1586 | 2000609 | 2001028 | + | 50s ribosomal protein l16. (rplP) | gp|AL161803|7321299 | 8.00E−54 |
| NO. 1022 | BL1589 | 2001282 | 2001542 | + | 30s ribosomal protein s17. (rpsQ) | swiss|O32990|RS17_MYCLE | 4.00E−27 |
| NO. 1023 | BL1590 | 2001637 | 2002005 | + | 50s ribosomal protein l14. (rplN) | gp|AL161803|7321302 | 2.00E−52 |
| NO. 1024 | BL1591 | 2002007 | 2002342 | + | 50s ribosomal protein l24 (rplX) | swiss|P33103|RL24_MICLU | 2.00E−25 |
| NO. 1025 | BL1592 | 2002339 | 2002911 | + | 50s ribosomal protein l5 (rplE) | gp|AL161803|7321304 | 4.00E−71 |
| NO. 1026 | BL1593 | 2002913 | 2003098 | + | 30s ribosomal protein s14-1. (rpsN) | gp|AL161803|7321305 | 4.00E−25 |

TABLE I-continued

| | Gene Name | Start | Stop | Strand | Function | Best Hit | Best Score |
|---|---|---|---|---|---|---|---|
| NO. 1027 | BL1594 | 2003188 | 2003586 | + | 30s ribosomal protein s8 (rpsH) | swiss|P95066|RS8_MYCTU | 3.00E−46 |
| NO. 1028 | BL1595 | 2003604 | 2004143 | + | 50s ribosomal protein l6 (rplF) | gp|AL161803|7321307 | 6.00E−49 |
| NO. 1029 | BL1596 | 2004145 | 2004516 | + | 50s ribosomal protein l18 (rplR) | gp|AL161803|7321308 | 9.00E−38 |
| NO. 1030 | BL1597 | 2004543 | 2005244 | + | ribosomal protein s5 (rpsE) | gp|AL161803|7321309 | 3.00E−56 |
| NO. 1031 | BL1599 | 2005438 | 2005890 | + | 50s ribosomal protein l15 (rplO) | swiss|P33101|RL15_MICLU | 2.00E−48 |
| NO. 1032 | BL1600 | 2006164 | 2007501 | + | preprotein translocase secy subunit. (secY) | swiss|P43416|SECY_STRSC | 5.00E−143 |
| NO. 1033 | BL1601 | 2007671 | 2008231 | + | adenylate kinase (EC 2.7.4.3) (atp-amp | swissnew|P33107|KAD_MICLU | 2.00E−46 |
| NO. 1034 | BL1602 | 2008408 | 2008626 | + | translation initiation factor if-1. (infA) | trembl|U15140|MB1540_1 | 1.00E−26 |
| NO. 1035 | BL1604 | 2008912 | 2009289 | + | 30s ribosomal protein s13. (rpsM) | swiss|O06327|RS13_MYCTU | 1.00E−52 |
| NO. 1036 | BL1605 | 2009315 | 2009812 | + | hypothetical protein with unknown function | embl|AL031317|SC6G4 | 5.00E−24 |
| NO. 1037 | BL1606 | 2009856 | 2010851 | + | dna-directed rna polymerase alpha chain (EC | swiss|O06324|RPOA_MYCTU | 5.00E−134 |
| NO. 1038 | BL1607 | 2010951 | 2011484 | + | 50s ribosomal protein l17 (rplQ) | swiss|O86775|RL17_STRCO | 2.00E−35 |
| NO. 1039 | BL1608 | 2011566 | 2012477 | complement | trna pseudouridine synthase a (EC 4.2.1.70) | swiss|O86776|TRUA_STRCO | 7.00E−54 |
| NO. 1040 | BL1609 | 2012753 | 2014933 | + | narrowly conserved hypothetical protein with | trembl|AE002040|AE002040_9 | 5.00E−102 |
| NO. 1041 | BL1610 | 2015140 | 2015940 | + | narrowly conserved hypothetical protein in | trembl|AE002037|AE002037_7 | 4.00E−21 |
| NO. 1042 | BL1611 | 2016516 | 2018318 | + | alpha-1-arabinofuranosidase a (EC 3.2.1.55) | gp|AL163003|7414545 | 5.00E−162 |
| NO. 1043 | BL1613 | 2018851 | 2019894 | + | laci-type tanscriptional regulator | trembl|AE001777|AE001777_1 | 3.00E−29 |
| NO. 1044 | BL1615 | 2020871 | 2021938 | + | n utilization substance homolog (nusA) | trembl|Z95207|MTCY24A1_1 | 1.00E−76 |
| NO. 1045 | BL1616 | 2022208 | 2025072 | + | translation initiation factor if-2 (infB) | swiss|Q9Z519|IF2_MYCLE | 0 |
| NO. 1046 | BL1617 | 2025225 | 2025698 | + | ribosome-binding factor a. (rbfA) | swiss|Q9Z527|RBFA_STRCO | 1.00E−25 |
| NO. 1047 | BL1618 | 2025700 | 2026863 | + | trna pseudouridine synthase b (EC 4.2.1.70) | trembl|AL035559|SC9F2_7 | 2.00E−53 |
| NO. 1048 | BL1619 | 2026961 | 2028085 | + | protein ribf [includes: riboflavin kinase (EC | trembl|AL035559|SC9F2_5 | 9.00E−41 |
| NO. 1049 | BL1620 | 2028100 | 2029638 | complement | alkylation damage repair protein (radA or sms) | trembl|AL049628|SCE94_2 | 5.00E−117 |
| NO. 1050 | BL1623 | 2030832 | 2031530 | complement | probable ribose 5-phosphate isomerase (EC | swiss|P72012|RPIA_METTH | 2.00E−43 |
| NO. 1051 | BL1624 | 2031661 | 2032647 | complement | ribonuclease h (EC 3.1.26.4) (mase h) (rnh) | pironly|G82101|G82101 | 1.00E−21 |
| NO. 1052 | BL1626 | 2033184 | 2034818 | complement | possible class i pyridine | swiss|P77212|YKGC_ECOLI | 1.00E−57 |
| NO. 1053 | BL1630 | 2037432 | 2039108 | complement | phosphoglucomutase (EC 5.4.2.2) (glucose | trembl|AL158061|SC6D11_39 | 5.00E−180 |
| NO. 1054 | BL1631 | 2039195 | 2040748 | complement | d-xylose-proton symporter (xylT) | swiss|O52733|XYLT_LACBR | 5.00E−100 |
| NO. 1055 | BL1632 | 2041248 | 2043623 | + | pts system, glucose-specific iiabc component | trembl|AF045481|AF045481_1 | 5.00E−154 |
| NO. 1056 | BL1633 | 2043641 | 2044480 | + | transcription antiterminator similar to lict | swiss|P39805|LICT_BACSU | 9.00E−38 |
| NO. 1057 | BL1634 | 2044504 | 2045883 | complement | conserved hypothetical protein wish possible | swiss|Q55452|Y036_SYNY3 | 7.00E−20 |
| NO. 1058 | BL1635 | 2045919 | 2047205 | + | seryl-trna synthetase (EC 6.1.1.11) | swiss|P96244|SYS_MYCTU | 5.00E−126 |
| NO. 1059 | BL1638 | 2048211 | 2049527 | + | solute binding protein of abc transporter for | trembl|AL132973|SCF91_20 | 1.00E−39 |
| NO. 1060 | BL1639 | 2049667 | 2050689 | + | permease of abc transporter for sugars | trembl|AL158061|SC6D11_6 | 2.00E−56 |
| NO. 1061 | BL1640 | 2050689 | 2051639 | + | permease of abc transporter for sugars | trembl|AL158061|SC6D11_5 | 3.00E−58 |
| NO. 1062 | BL1642 | 2054142 | 2055221 | + | narrowly conserved hypothetical protein wilh | trembl|D90908|SSD908_48 | 7.00E−55 |
| NO. 1063 | BL1643 | 2055268 | 2056815 | + | galactose-1-phosphate uridylyltransferase (EC | trembl|AF082008|AF082008_2 | 1.00E−72 |
| NO. 1064 | BL1644 | 2056884 | 2057906 | + | ndp-glucose 4-epimerase (EC 5.1.3.2) | swiss|P24325|GALE_HAEIN | 5.00E−119 |
| NO. 1065 | BL1645 | 2057954 | 2058649 | complement | response regulator of two-component system | trembl|AL109661|SC6E10_14 | 1.00E−30 |
| NO. 1066 | BL1652 | 2067540 | 2068730 | complement | araj-like protein probably involved in transport | trembl|U73857|ECU73857_115 | 7.00E−69 |
| NO. 1067 | BL1654 | 2069231 | 2070913 | + | lysyl-trna synthetase 1 (EC 6.1.1.6) | swissnew|O06284|SYK1_MYCTU | 5.00E−154 |
| NO. 1068 | BL1655 | 2070975 | 2071940 | + | probable 1,4-dihydroxy-2-naphthoate | swiss|O07134|MENA_MYCLE | 1.00E−44 |
| NO. 1069 | BL1656 | 2071970 | 2072740 | + | phosphoglycerate mutase (EC 5.4.2.1) | trembl|M83661|SCPGM_1 | 1.00E−86 |

TABLE I-continued

| | Gene Name | Start | Stop | Strand | Function | Best Hit | Best Score |
|---|---|---|---|---|---|---|---|
| NO. 1070 | BL1657 | 2073099 | 2073773 | complement | response regulator of two-component system | swissnew|O07167|PHU1_MYCTU | 2.00E−30 |
| NO. 1071 | BL1658 | 2073788 | 2075158 | + | histidine kinase sensor of two component | gp|AL160331|7242750 | 6.00E−50 |
| NO. 1072 | BL1660 | 2075668 | 2076810 | complement | probable phosphoserine aminotransferase (EC | swissnew|O33062|SERC_MYCLE | 5.00E−120 |
| NO. 1073 | BL1661 | 2077204 | 2078160 | + | hypothetical protein with c-terminal homology to | trembl|AJ243106|STH243106_4 | 2.00E−25 |
| NO. 1074 | BL1664 | 2080185 | 2081222 | + | widely conserved protein in universal stress | swiss|Q10851|YK05_MYCTU | 2.00E−26 |
| NO. 1075 | BL1665 | 2081894 | 2082694 | + | thymidylate synthase(EC 2.1.1.45) (thyA) | swiss|O33306|TYSY_MYCTU | 5.00E−109 |
| NO. 1076 | BL1666 | 2082804 | 2083466 | + | dihydrofolate reductase (EC 1.5.1.3) (dfrA) | trembl|AF006616|AF006616_1 | 3.00E−26 |
| NO. 1077 | BL1667 | 2083590 | 2084108 | + | low molecular weight | swissnew|P53433|PTPA_STRCO | 8.00E−22 |
| NO. 1078 | BL1668 | 2084287 | 2084619 | complement | branched-chain amino acid permease (alzD) | swiss|O07923|AZLD_BACSU | 9.00E−37 |
| NO. 1079 | BL1669 | 2084616 | 2085632 | complement | narrowly conserved hypothetical protein with | swiss|O07942|AZLC_BACSU | 6.00E−74 |
| NO. 1080 | BL1670 | 2085856 | 2086716 | complement | widely conserved hypothetical protein with | swiss|P32049|YGGH_ECOLI | 1.00E−30 |
| NO. 1081 | BL1671 | 2087044 | 2088057 | + | udp-glucose 4-epimerase (EC 5.1.3.2) | tremblnew|AL163672|SCE50_16 | 1.00E−85 |
| NO. 1082 | BL1672 | 2088998 | 2090302 | complement | possible cyclopropane-fatty-acyl-phospholipid | trembl|AL023596|MLCB2407_9 | 3.00E−98 |
| NO. 1083 | BL1673 | 2090742 | 2091893 | + | possible lactaldehyde reductase (EC 1.1.1.77) | swiss|P11549|FUCO_ECOLI | 5.00E−120 |
| NO. 1084 | BL1675 | 2093118 | 2094632 | + | hypothetical integral membrane protein in | trembl|AL020958|SC4H8_6 | 2.00E−61 |
| NO. 1085 | BL1676 | 2094632 | 2095855 | + | narrowly conserved hypothetical transmembrane | trembl|L39794|PPRRMP_7 | 2.00E−25 |
| NO. 1086 | BL1677 | 2095950 | 2096906 | + | atp-binding protein of abc transporter system | trembl|AP000005|AP000005_137 | 3.00E−40 |
| NO. 1087 | BL1679 | 2098599 | 2100089 | + | hypothetical secreted protein with d-ala-d-ala | trembl|AL049841|SCE9_15 | 2.00E−30 |
| NO. 1088 | BL1680 | 2100179 | 2101345 | + | narrowly conserved hypothetical protein similar | trembl|AL049841|SCE9_13 | 3.00E−39 |
| NO. 1089 | BL1681 | 2101332 | 2101895 | + | hypoxanthine-guanine phosphoribosyltransferase | trembl|AL049841|SCE9_12 | 4.00E−47 |
| NO. 1090 | BL1682 | 2101892 | 2103982 | + | atp-dependent zinc metallopeptidase involved in | trembl|AL049841|SCE9_11 | 0 |
| NO. 1091 | BL1683 | 2104077 | 2104676 | + | gtp cyclohydrolase i (EC 3.5.4.16) (gtp-ch-i) | swissnew|Q9X8I3|GCH1_STRCO | 3.00E−64 |
| NO. 1092 | BL1684 | 2104739 | 2105614 | + | dihydropteroate synthase 1 (EC 2.5.1.15) | trembl|AL049841|SCE9_5 | 2.00E−58 |
| NO. 1093 | BL1685 | 2105725 | 2107137 | + | probable bifunctional folate synthesis protein | trembl|AL049841|SCE9_8 | 1.00E−30 |
| NO. 1094 | BL1687 | 2107939 | 2108838 | complement | acyl-coa thioesterase ii (EC 3.1.2.-) (teii) | pironly|A82248|A82248 | 7.00E−39 |
| NO. 1095 | BL1688 | 2109150 | 2110829 | complement | atp binding protein of abc transporter | trembl|AL021246|MTV008_32 | 0 |
| NO. 1096 | BL1691 | 2111662 | 2112612 | + | glucokinase (EC 2.7.1.2) (glucose kinase | swissnew|P40184|GLK_STRCO | 1.00E−70 |
| NO. 1097 | BL1692 | 2112637 | 2113503 | complement | atp binding protein of abc transporter for | trembl|AL009199|SC7B7_7 | 4.00E−57 |
| NO. 1098 | BL1693 | 2113541 | 2114710 | complement | probable repressor protein in (nagc/xylr) | trembl|AL009199|SC7B7_5 | 5.00E−74 |
| NO. 1099 | BL1694 | 2114962 | 2116119 | + | probable sugar binding protein of abc | trembl|AL133423|SC4A7_32 | 7.00E−71 |
| NO. 1100 | BL1695 | 2116220 | 2117773 | + | atp binding protein of abc transporter for | trembl|AF160811|AF160811_1 | 5.00E−168 |
| NO. 1101 | BL1696 | 2117773 | 2118990 | + | | trembl|AF160811|AF160811_2 | 4.00E−89 |
| NO. 1102 | BL1699 | 2120080 | 2120502 | + | hypothetical transmembrane protein possibly | trembl|AB000617|AB000617_2 | 5.00E−22 |
| NO. 1103 | BL1700 | 2120510 | 2120929 | + | polypeptide deformylase (EC 3.5.1.31) (pdf) | swiss|O08450|DEF_CLOBE | 8.00E−32 |
| NO. 1104 | BL1704 | 2123529 | 2124878 | + | xylose isomerase (EC 5.3.1.5) (xylA) | swiss|P29443|XYLA_LACBR | 0 |
| NO. 1105 | BL1705 | 2125144 | 2126421 | + | transpsosase in is256 family | trembl|AF082836|AF082836_1 | 5.00E−155 |
| NO. 1106 | BL1706 | 2126337 | 2126684 | + | possible sugar permease | trembl|AF160811|AF160811_2 | 9.00E−20 |
| NO. 1107 | BL1709 | 2127852 | 2129372 | complement | xylulose kinase (EC 2.7.1.17) (xylulokinase) | swiss|P27156|XYLB_STRRU. | 1.00E−78 |
| NO. 1108 | BL1710 | 2129592 | 2130821 | + | possible xylr-type repressor | trembl|AL133210|SCG11A_2 | 1.00E−47 |
| NO. 1109 | BL1711 | 2131150 | 2131362 | + | 50s ribosomal protein l31. (rpmE) | swiss|Q10608|RL31_MYCTU | 7.00E−22 |
| NO. 1110 | BL1712 | 2131516 | 2132604 | + | peptide chain release factor 1 (rf-1) (prfA) | swiss|Q10605|RF1_MYCTU | 5.00E−104 |

TABLE I-continued

| | Gene Name | Start | Stop | Strand | Function | Best Hit | Best Score |
|---|---|---|---|---|---|---|---|
| NO. 1111 | BL1713 | 2132691 | 2133575 | + | possible methylase protein | swiss|Q10602|HEMK_MYCTU | 2.00E−34 |
| NO. 1112 | BL1714 | 2133848 | 2135035 | + | solute binding protein of abc transporter for | | 3.00E−39 |
| NO. 1113 | BL1715 | 2135277 | 2136203 | + | permease of abc transporter for branched-chain | swiss|P30295|LIVH_SALTY | 2.00E−64 |
| NO. 1114 | BL1716 | 2136220 | 2137296 | + | permease of abc transporter for branched-chain | pironly|A83032|A83032 | 1.00E−47 |
| NO. 1115 | BL1717 | 2137293 | 2138153 | + | atp binding protein of abc transporter for | trembl|AE001771|AE001771_7 | 1.00E−71 |
| NO. 1116 | BL1718 | 2138153 | 2138857 | + | atp binding protein of abc transporter for | trembl|AL109732|SC7H2_26 | 7.00E−76 |
| NO. 1117 | BL1719 | 2138989 | 2139666 | complement | probable sugar o-acetyltransferase (EC 2.3.1.18) | swiss|Q09707|YA39_SCHPO | 6.00E−36 |
| NO. 1118 | BL1720 | 2139841 | 2140515 | + | conserved protein in the sua5/ycio/yrdc family | trembl|AF144563|AF144563_3 | 2.00E−23 |
| NO. 1119 | BL1721 | 2140629 | 2141795 | + | possible undecaprenyl-phosphate | swiss|P45830|RFE_MYCLE | 1.00E−65 |
| NO. 1120 | BL1722 | 2141764 | 2143401 | + | inosine-5'-monophosphate dehydrogenase (EC | gp|AL161755|7320889 | 5.00E−171 |
| NO. 1121 | BL1723 | 2143569 | 2144219 | + | probable oligoribonuclease (EC 3.1.-.-) (orn) | swissnew|P57666|ORN_STRCO | 8.00E−54 |
| NO. 1122 | BL1724 | 2144268 | 2145686 | + | possible helicase | trembl|AF074944|AF074944_1 | 2.00E−55 |
| NO. 1123 | BL1726 | 2147513 | 2148685 | + | possible pyruvate formate-lyase activating | trembl|Z83867|MTCY3A2_8 | 5.00E−108 |
| NO. 1124 | BL1728 | 2149479 | 2151272 | + | prolyl-trna synthetase (EC 6.1.1.15) | swiss|O05814|SYP_MYCTU | 5.00E−176 |
| NO. 1125 | BL1730 | 2152374 | 2154611 | complement | belongs to peptidase family m13 (zinc | trembl|AL021928|MTV033_5 | 5.00E−165 |
| NO. 1126 | BL1732 | 2155895 | 2156677 | + | methionine aminopeptidase (EC 3.4.11.18) (map) | trembl|AL023861|SC3C8_28 | 1.00E−65 |
| NO. 1127 | BL1733 | 2156951 | 2158243 | + | citrate synthase 1 (EC 4.1.3.7) (gltA2) | swiss|Q10530|CISY_MYCTU | 5.00E−124 |
| NO. 1128 | BL1734 | 2158457 | 2159476 | complement | widely conserved hypothetical protein with | trembl|Z93777|MTCI364_11 | 3.00E−84 |
| NO. 1129 | BL1736 | 2160873 | 2165057 | + | possible helicase | trembl|X98455|BCX98455_2 | 5.00E−108 |
| NO. 1130 | BL1738 | 2165706 | 2166305 | complement | hypothetical protein with probable | tremblnew|AJ251800|STH251800_1 | 7.00E−25 |
| NO. 1131 | BL1739 | 2166307 | 2166822 | + | possible xorii very-short-patch-repair | swissnew|Q9JWD6|VSR_NEIMA | 3.00E−34 |
| NO. 1132 | BL1740 | 2166853 | 2167908 | complement | probable oxidoreductase | trembl|AL133220|SCC75A_31 | 3.00E−46 |
| NO. 1133 | BL1741 | 2168002 | 2169225 | + | probable aspartate aminotransferase | pironly|D83057|D83057 | 6.00E−87 |
| NO. 1134 | BL1742 | 2169403 | 2170371 | + | widely conserved hypothetical protein with | trembl|AL049819|SCE7_15 | 1.00E−80 |
| NO. 1135 | BL1748 | 2173544 | 2175409 | + | probable long-chain-fatty-acid-coa ligase (EC | trembl|AL049497|SC6G10_4 | 5.00E−136 |
| NO. 1136 | BL1749 | 2175548 | 2176072 | complement | possible nad(p)h oxidoreductase (EC 1.6.99.-) | swiss|P54439|YRKL_BACSU | 7.00E−36 |
| NO. 1137 | BL1751 | 2176548 | 2177918 | complement | exonuclease vii, large subunit (EC 3.1.11.6) | tremblnew|AL391754|SCK7_29 | 2.00E−88 |
| NO. 1138 | BL1752 | 2178386 | 2180794 | + | anaerobic ribonucleoside-triphosphate reductase | trembl|U73336|U73336_1 | 0 |
| NO. 1139 | BL1753 | 2180861 | 2181670 | + | anaerobic ribonucleoside-triphosphate reductase | trembl|U73336|U73336_2 | 7.00E−64 |
| NO. 1140 | BL1754 | 2181898 | 2187036 | + | long hypothetical protein with unknown function | trembl|AE000682|AE000682_3 | 2.00E−73 |
| NO. 1141 | BL1755 | 2187342 | 2188478 | + | possible glutamate-cysteine ligase, (EC | trembl|AF128454|AF128454_1 | 3.00E−33 |
| NO. 1142 | BL1757 | 2189465 | 2191828 | + | possible beta-glucosidase (EC 3.2.1.21) | trembl|AF006658|BFAF6658_1 | 5.00E−119 |
| NO. 1143 | BL1761 | 2192953 | 2194167 | + | probable beta-1,3-exoglucanase | tremblnew|AY005434|AY005434_1 | 5.00E−37 |
| NO. 1144 | BL1763 | 2194834 | 2195973 | + | possible beta-glucosidase b (EC 3.2.1.21) | trembl|U92808|U92808_1 | 1.00E−58 |
| NO. 1145 | BL1766 | 2197109 | 2199067 | + | atp-binding protein of abc transporter | trembl|AE001710|AE001710_10 | 5.00E−114 |
| NO. 1146 | BL1767 | 2199064 | 2201079 | + | abc transporter, atp-binding transmembrane | tremblnew|AP001509|AP001509_253 | 5.00E−110 |
| NO. 1147 | BL1768 | 2201259 | 2202284 | + | probable laci-type transcriptional regulator | trembl|AL136519|SCC57A_15 | 4.00E−43 |
| NO. 1148 | BL1770 | 2202998 | 2203918 | + | widely conserved hypothetical protein in the | tremblnew|AE005179|AE005179_9 | 8.00E−74 |
| NO. 1149 | BL1771 | 2204020 | 2205450 | + | c4-dicarboxylate transporter (dcuC) | pironly|G82431|G82431 | 3.00E−65 |
| NO. 1150 | BL1772 | 2205676 | 2206644 | + | sugar kinase in pfkb family (rbsK) | trembl|AL136519|SCC57A_18 | 2.00E−43 |
| NO. 1151 | BL1774 | 2207174 | 2208181 | + | laci-type transcriptional regulator | tremblnew|AP001514|AP001514_24 | 2.00E−58 |
| NO. 1152 | BL1775 | 2208244 | 2208846 | complement | fragment of beta galactosidase | trembl|AJ242596|BLO242596_1 | 3.00E−62 |
| NO. 1153 | BL1776 | 2208904 | 2210115 | complement | probable aminotransferase | swiss|Q08432|PATB_BACSU | 4.00E−54 |

TABLE I-continued

| | Gene Name | Start | Stop | Strand | Function | Best Hit | Best Score |
|---|---|---|---|---|---|---|---|
| NO. 1154 | BL1777 | 2210709 | 2214020 | + | isoleucyl-trna synthetase (EC 6.1.1.5) | swiss\|Q10765\|SYI_MYCTU | 0 |
| NO. 1155 | BL1778 | 2214216 | 2214866 | + | truncated type i restriction system specificity | embl\|I46882\|I46882 | 2.00E−51 |
| NO. 1156 | BL1779 | 2214859 | 2215788 | complement | phage family integrase | trembl\|L44593\|LLATTP_8 | 2.00E−51 |
| NO. 1157 | BL1780 | 2215779 | 2216348 | complement | truncated type i restriction system specificity | trembl\|AF153410\|AF153410_1 | 2.00E−54 |
| NO. 1158 | BL1781 | 2216382 | 2217317 | + | our restriction endonuclease (mrr) | trembl\|Z83863\|MTCY159_5 | 2.00E−50 |
| NO. 1159 | BL1782 | 2217349 | 2219916 | + | modification (methylase) protein of type i | trembl\|AF177167\|AF177167_4 | 5.00E−103 |
| NO. 1160 | BL1783 | 2219916 | 2221136 | + | hsds specificity protein of type i restriction- | trembl\|AF027167\|AF027167_1 | 1.00E−66 |
| NO. 1161 | BL1785 | 2222715 | 2226002 | + | hsdr-like protein of type i restriction | trembl\|AF013165\|AF013165_2 | 7.00E−93 |
| NO. 1162 | BL1786 | 2226070 | 2227290 | complement | s-adenosylmethionine synthetase (EC 2.5.1.6) | trembl\|new\|AX063959\|AX063959_1 | 5.00E−136 |
| NO. 1163 | BL1788 | 2228055 | 2229917 | + | dihydroxy-acid dehydratase (EC 4.2.1.9) (dad) | swissnew\|O69198\|ILVD_STRCO | 0 |
| NO. 1164 | BL1789 | 2230008 | 2230994 | complement | methionyl-trna formyltransferase (EC 2.1.2.9) | gp\|AL591391\|7209233 | 2.00E−80 |
| NO. 1165 | BL1791 | 2231781 | 2234093 | complement | probable primosomal protein n' (replication | gp\|AL591391\|7209235 | 3.00E−72 |
| NO. 1166 | BL1792 | 2234133 | 2234885 | complement | probable phosphoserine phosphatase (EC 3.1.3.3) | trembl\|AL096844\|SCI28_2 | 3.00E−49 |
| NO. 1167 | BL1793 | 2234906 | 2235604 | + | hypothetical conserved transmembrane protein in | trembl\|D64004\|SSSLRF_46 | 4.00E−38 |
| NO. 1168 | BL1794 | 2235665 | 2237230 | + | probable aaa-family atpase | swiss\|O33250\|YL15_MYCTU | 5.00E−114 |
| NO. 1169 | BL1795 | 2237252 | 2238919 | + | hypothetical proteasome-associated protein | trembl\|Z97559\|MTCY261_8 | 6.00E−95 |
| NO. 1170 | BL1797 | 2240121 | 2241581 | + | hypothetical proteasome-associated protein | trembl\|AL035310\|MLCB2533_19 | 4.00E−88 |
| NO. 1171 | BL1799 | 2242124 | 2244685 | complement | narrowly conserved hypothetical membrane | trembl\|AL021942\|MTV039_22 | 3.00E−54 |
| NO. 1172 | BL1800 | 2244817 | 2246262 | complement | adenylosuccinate lyase (EC 4.3.2.2) | pironly\|A82237\|A82237 | 5.00E−111 |
| NO. 1173 | BL1811 | 2254166 | 2255254 | complement | widely conserved moxr-like protein in magnesium | pironly\|C83106\|C83106 | 4.00E−72 |
| NO. 1174 | BL1812 | 2255285 | 2255926 | complement | Uracil-dna glycosylase (EC 3.2.2.-) (udg) (ung) | swiss\|P95119\|UNG_MYCTU | 2.00E−77 |

The ORFs corresponding to NO. 1 to 1147 nucleotide sequences are defined in table 1, supra, and are represented by their position in the genomic sequence SEQ. ID. NO. 1. For example, the ORF3 sequence is defined by the nucleotide sequence between the nucleotides at position 4622 and 6472 on the sequence SEQ No. 1, ends included.

The open reading frames have been identified via homology analyses as well as via analyses of potential ORF start sites. It is to be understood that each identified ORF comprises a nucleotide sequence that spans the contiguous nucleotide sequence from the codon immediately 3' to the stop codon of the preceding ORF and through the 5' codon to the next stop codon of SEQ. ID. NO. 1 in frame to the ORF nucleotide sequence.

Table 1 also depicts the results of homology searches that compared the sequences of the polypeptides encoded by each of the ORFs to sequences present in public published databases. It is understood that in one embodiment, those polypeptides listed in Table 1 as exhibiting greater than about 99% identity to a polypeptide present in a publicly disclosed database as represented by sequence similarity scores are not considered part of the present invention. Likewise in this embodiment, those nucleotide sequences encoding such polypeptides are not considered part of the invention.

As regards the homology with the ORF nucleotide sequences, the homologous sequences exhibiting a percentage identity with the bases of one of the ORF nucleotide sequences of at least 80%, preferably 90% and 95%, are preferred. Such homologous sequences are identified via, for example, the algorithms described above and in the examples below. The said homologous sequences correspond to the homologous sequences as defined above and may comprise, for example, the sequences corresponding to the ORF sequences of a bacterium belonging to the *Bifidobacterium* family.

These homologous sequences may likewise correspond to variations linked to mutations within the same species or between species and may correspond in particular to truncations, substitutions, deletions and/or additions of at least one nucleotide. The said homologous sequences may also correspond to variations linked to the degeneracy of the genetic code or to a bias in the genetic code which is specific to the family, to the species or to the variant and which are likely to be present in *Bifidobacterium*.

Particularly interesting sequences are nucleotide sequences, which encode the following polypeptides or fragments thereof:

(a) SEQ. ID. NO.5 (ORF13)
MPTGRVRWFDAAKGYGFITSEEGKDVFLPAQALPTGVTTLRKGAKVEYSV
VDGRRGPQAMDVRLIASAPSLVKATRPKADDMAAICEDLIKMLDAAGNTL

-continued
RRHRYPSAADSKKLATLLRAVADQFDVQD (b) SEQ. ID. NO.525 (ORF1827)
MTTAAAQAPAPGKLEFKDDYTPDEAERVIRNSKGLPVGVRPKMVWTWKKA
LLWAAIAIVCACGWAILAVSRGEQISAIWFLVVALSSSYAIAYRFYAYYIQ
IKIMRTDDANATPAERVHDGANFERTDRRVLFGQHFAGISGAGPLVGPIL
AAQMGYLPSTLWIILGVIFAGAVQDMLVLWISAKRRGRSLGQMATDEMGK
FGGMILSIFLVVMTAIAMAFLALVAIKAMAASPWAVFSIGMTIPIALIMG
CYQRFLRPGRVIETTLLGFVLLVLDIVAGGWIASIPAVAAVFTLDAKQLV
IALVIYSFAAAALPHWLLVTPRDYLSTLMKIGTLVLLVIGIIIANPSVKV
PGLTELASTSTGPTFSGNLFPFLFITIACGALSGFHGAVSSGLTPKAVEK
ENQIRMIGYGSMLVESFTAVIALIAAITISQGVYFSTNMSAAQITAASGV
SISATSTPGEQADAAVKAVESMKVSDIEGNQMQVTWDSVDENGAAKTYEG
AAALEQAAADIGETSIVSRTGGATTFAMGMANFLKSYLGGHDSMAFWYHF
AIMFEALFILTTVDNGTRVARYQIGEMLGNVRKLKKFADPTWKPGN
IITTLIATALWGGLLWMGVSDANGGINAMVPIFGISNQLLAAACFV
LITVCVAKMGYWKHLWIPVVPLVWDIAVTFTADFQKIFGPLSYFTT
ASKYQAQIDSGELTGEALTNAKAALSNAYLDGVLSVFFLVMMGVFV
VVGIVVVARTFAAGKYGAETTSEEPFVESQWFAPSSLVATALEKKV
QREYSAKLHELVRNGQVAA c) SEQ. ID. NO.424 (ORF1473)
MTQSRRMLVLRAVVEDYIRSQEPVGSTSLTRDHDLGVSSATIRNDMAALE
DEGYLIQPHTSAGRVPTEKGYRYFVDRLATVVPLSEAQRRGINSFLSGSV
SLKDALQRSARLLSEITGQVAVVASPSLAKATLRHVEMVPVAMTTLLAVV
ITDTGRVAQHGLTIASMPAVDEINRLSNTVNEQCDGLSLSKSAETVRSIA
ASAGYESVRGVADTLADAFESMALDERANELYMSGTSHLAHSRSLADLAP
LFDALEEQVVLMKLMSNLSEETNASGVGVAIGSEMHTPGLLHASVVSSGY
GRSGAAGEPAGNDPVGEPETESETESQTNDTEPIAFVGSIGPTHMDYAAT
MAAVRAVARYLTAFLSEGRTQD d) SEQ. ID. NO.548 (ORF1905)
MYFKDGNDNAQRGGSTVRRSRQRRIMGRVVSYNEDVPRCTFCGKTEHQVR
KLVAGPNASICDECIALCVDIISEERVKDAEVNSLSLPKPAQIFDYLNRY
VIGQENAKRALSVAVYNHYKRVNMELQESAEQLDGNNGHSGQTKSQAKQS
VPTQTRATRRSNDPLADVEVAKSNILLLGPTGVGKTYLAQALARVMNVPF
VITDATTLTEAGYVGDDVETVLQRLLQAADGDVSRAQHGIIYIDEIDKIA
RKSGENTSITRDVSGEGVQQALLKILEGTIASVPLEGTRKHKEQDVAQMD
TRGILFICGGAFVGLTDIVRKRLGRRETGFGANWHDADMKDEELLEQVNA
DDLAEFGLLPEFIGRLPVTSVLKELTVDDLTAILTQPANALIKQYRKLFA
VDGVDLQFTEQAIRAIADIAIKQGTGARGLRSIIERTLQDTMFQLPSLDD
VRQVIVDKASVEGSSTPKLLREAVDVPQGRLKVAQSVLLDRVRTHEA e) SEQ. ID. NO.74 (ORF219)
MSEQLMEQYRLRGQRKCRNACIAAIVTVVLVAVAGGVWWTAGDGSALVR
NMFKPKATPATQPVVNSTATFAYRTAPEFLAMEAGDRGTGNVNYSPASMW -continued
MALAIAAQGANGTTRSQLNELLGSGSLTDSDYQSLLSSINGQYSGAKSEM
SAANSLWIDDDYSLASDYQSTVKKMFEAEVTTLPFDDQAAAKMSDWIAKH
TNGSLKPKITLRDREVLSIINTVYADGRWKDPFEEQSTGNGTFHGEAGDA
QVPMMHQTFSQMAYGHDEYNTWQRVEIPFDNGGNLAIVLPAEGHFDELAG
DAEKLSWAFGTCSTASLGEGAMGCAADSMPGWGVSVNSVMVNVTLPRFTI
DSMFDSEATIKAFEKLGVTDAFSAGDADFTKMIDTGSHGENLYIGSILQG
TRIEVNEAGAKAMSFTKVGADSVSAPVDNVEFTVDRPFLYSYVTPDGIPL
FIGAVRNLGGVGGEN f) SEQ. ID. NO.576 (ORF1972)
MQIRPGSMYPLGASYDGAGVNFALYSQVAQKVELCLFDEHDVETRIEMTE
RNSYVWHNYIPGLHPGQRYGYRVYGPYDPVHGLRCNPNKLLLDPYAKAIE
GNIDGDESLFSYWFKSPDDNSAMNDLDSAAHTMKSAVINPYFDWGNDQHP
YISYHDSVIYEAHVRGMTNLNMDVPPDIRGTYAGLAYPSVIEYLKKLGIT
AIELMPIHQFVNDSFLQEKGLSNYWGYNTIGFFAPHNAYSSSGERGEQVN
EFKSMVKAYHRAGMEVILDVVYNHTAEGNHMGPTLSFKGIDNASYYRLVE
GDQQHYFDTTGTGNSLLMRSPHALQLITDSLRYWVTEMHVDGFRFDLAAT
LARQFQEVDKLSAFFDIVEQDPIISRVKLIAEPWDLGSGGYQVGGFPSSW
SEWNGRYRDTVRDFWRSQPSTLPEFASRLMGSSDLYQVNGRRPVASVNFI
TAHDGFTMNDLVSYNEKHNEANGEGNRDGESNNRSWNCGVEGPTNIPDVN
DLRQRQMRNMFATLLFSQGIPMICGGDEVARTQQGNNNAYCQDNEISWTN
WHLDKGRKELLAFVSKLIHLRLDHPVLHRRRFFTGREPGDDSNTIPQVEW
FDHTGSIMDMDDWQNTHAFSMMIYLNGSDIPEVDWYGNRMVDNDFILIFN
AHYEPIMFTLPDERYGRKWQLVVDTHNPNEPALSYEAGFMITAQSRSFLM
LMSAKKPKKPMGL g) SEQ. ID. NO.403 (ORF1403)
MEIRARPHMASGSYRELFSARMMYGMQYIQQTIVGIDGSEARFFGYVADN
SEEMEPDRIRPAILILPGGGYAMTSDREAEPVALQFLAKGFAVFVLRYSV
QPSRYPVALLEAAEAMRLIRANVDQWHVNPAQVAVLGFSAGGHLAANLAT
SVGDEDIREQGGMDPDAVRPNALMLSYPVITAGKYAHRGSFQCLLGDQAH
NQALLDKFSIEKHIDAKTPPVFVWHTMTDDAVPVENTLMLIQACRAAGVS
IEAHLFPEGSHGLSLANAETAGNGFYAHIVECVQCWPDLAEAWLRRLF (h) SEQ. ID. NO.804 (ORF2676)
MFLKPEQQLERCRRIVRQRVDPHIHPSIAQLTVESYDIPGEPMPSDEFFA
KLDRGDIDFKPFMLGSEWGTTWGTVWFRLTGTVPAGYPKGKPLELILDLG
WYPHSCGGHIEGLVYRADGTAIKAVHPLNYWVPFMDAEGNAQVPVAEDGS
FTLYLEAASNPLLLGVPPFIETELGDHATGKPDEPYVFKSADLAEFDERY
ENYSVDLDVVSSLMEFADKQSPRYWQLAKALQRSLNAYDERNPESVEAAR
AVLAGVLAKPANASAMNVSAIGHAHIDSAWLWPVRETRRKVARTVSNALA
LMDADPDFKYAMSSAQQYAWLEEDHPDIFKRMKRRIEEGRFIPVGGMWVE
ADGMLPAGESLIRQIAYGRKYFKEHLGVEPKGVWLPDSFGYTGAWPQIAR
RAGYEWFLTQKISWNDTTKFPHHSFMWEGIDGSRIFTHFPPADTYAAWCK
VQELDYAEKNFQDKDLSDRSLLLFGFGDGGGGPTRNMMEHLRYENLEGV -continued

SKVSIEEPNDFFDKAHQQLAENAGPEMPVWKGELYLELHRGTLTSQQDMK

RGCRQEESLLRTVEYLGAAAVLSDPEYVYPREELDRIWKTLLLNQFHDIL

PGSAIAWVHREAREDYRRDLKRLAEIAQDMCAVLRKANPQADLLAEARIS

QFRNDGASWHANRINEPTDALSVLTQTLDNGRVLLANGVLSVTIEADGTI

SSLLDEEHGRELVPAGTRLGQYELLRDEPAVWDAWEIERESLLMANAVTG

SIESVNTENGAAQVHVHTADGDTVITTTITLRPGSHTLDFHADIDWHERE

RFLKVDLPLGIVADQATYDCQYGLIRRPIVKNTASDEAKYESSTNRFAII

GDAGYAAAVINGSVYGSDASPIAGNAAEGRDSGTMFRLSLLSAPTFPDPR

TDIGSHEFDWSVVADATVDRALDAAGVLNAPVLHDVPDITPLASIESVNG

TVVLDWMKLADDGSGDLIVRAYEAAGGQADAMLHVCPALAGASVHETNVL

EGDDLAADLPVALQDGRQNAEGATLHFGPFQLATLRITR (i) SEQ. ID. NO.313 (ORF1077)
MISRDGWAVIDDSAANIIETDTVNGKANPFGTWVSPPATAETDLYFFGY

GHRYIEAVRDFYRLTGPTPLLPRFAMGNWWSRYYRYTQDGYLALMDRFKR

EGIPFTTSVIDMDWHRVDDVDPKYGSGWTGYSWNRELFPDPPAFLADLHR

RGLRTTLNVHPRDGVRAFEDAYPEVAKRVGIDPATEENVEFDLTNPDFVD

AYFDMHHRMEAEGVDFWWLDWQQGGVTRQKGLDPLWMLNHMHYLDSGRGG

NWPLTFSRYAGPGSHRYPVGFSGDTIVTWESLAFQPQFTATASNIGYGWW

SHDIGGHMFGYRNEELEARWYQLGAFSPINRLHSSNSPFSGKEPWNFNRD

VSAAMVDALRLRHAMMPYLYTMNYRAAEAGRPLVEPMYWQNPDTPDAYEV

PDEFRFGTELVVAPIVSPDDAAACRGRADAWLPQGEWFDFFDGRRYVSSD

AAGRRLEVWRSLDRTPVFAKAGAIVPLQDVAESGEAINSIANPQALRVLV

FPGADGSFVMREDRGTWGAPSADTAIAFTWGGADASPSAFTVAPVTGDTS

AVPELRDWTVVFRGVAPVDAASGVRAWSGEAPVEATVAYDEATMSLTVSV

TGISSAASLRIEIPGGLRIADNPVESDAMDLLLHAQMLYRTKELALQAVH

KLGIGAIGALRTMNRGPRYANDFWITDMPDAVAGALEEILLRS

It will be understood that the sequence information contained in the present application may be utilized for selecting a polynucleotide of interest, i.e. a nucleic acid containing an open reading frame encoding a known or an unknown, putative polypeptide and transforming microorganisms with the selected polynucleotide. As transformation vehicles the well known plasmids, phage vectors (transfection) or F-vectors (conjugation) may be utilized. The nucleic acid introduced into the microorganism selected may be expressed and its biological function may be either utilized as such, if known, or elucidated, in case a so far unknown polypeptide is expressed. The microorganism selected may be a *Bifidobacterium* itself or other well known microorganisms, such as bacteria, e.g. *E. coli, Lactobacilli, Streptococci* or yeast, insect cells or even animal and plant cells.

It will be understood that the polypeptide may be expressed as such or as a fusion polypeptide. The skilled person is well aquatinted with techniques performing such a ligation and expressing the corresponding fusion-polypeptide in an appropriate cell.

In view of the present invention also new recombinant vectors for the cloning and/or the expression of a nucleotide sequence according to the present invention may be devised. The vectors comprise elements necessary to enable expression and/or secretion of the nucleotide sequences in a given host cell, such as a promoter, signals for initiation and for termination of translation, as well as appropriate regions for regulation of transcription. For example, expression of a protein or peptide may be controlled by any promoter/enhancer element known in the art. Exemplary promotors are the CMV promoter, the SV40 early promoter region, the promoter contained in the 3' long terminal repeat of the rous sarcoma virus, the herpes thymidine kinase promoter, the regulatory sequences of the metallothionein gene, or, for prokaryotic expression systems, the β-lactamase promoter, the tac promoter or the T7 promoter.

The vector should be capable of being stably maintained in the host cell and may optionally possess particular signals specifying the secretion of the translated protein. These different elements are chosen according to the host cell utilized. To this effect the nucleotide sequences according to the invention may be inserted into autonomously-replicating vectors within the chosen host, or integrative vectors in the chosen host, such as e.g yeast artificial chromosomes, plasmids or viral vectors. It will be appreciated that the vector may well be the plasmid according to SEQ. ID. NO. 2 or a recombinant form thereof, which has been supplemented by particular ori's that enable a high copy number.

Any of the standard methods known to those skilled in the art for inserting DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

The vector may be used for transcription and/or translation of a nucleic acid comprised in/by SEQ. ID. NO. 1 or SEQ. ID. NO. 2, to produce RNA or antisense RNA, respectively. Such a vector can remain episomal or become chromosomally integrated, as long as it can be transcribed to produce the desired transcript.

The antisense nucleic acids of the invention comprise a sequence complementary to at least a portion of a RNA transcript of a polynucleotide sequence in SEQ. ID. NO. 1, designating a sequence having sufficient complementarity to be able to hybridize with the RNA, forming a stable duplex. In the case of double-stranded antisense nucleic acid sequence, a single strand of the duplex DNA may thus be tested, or triplex formation may be assayed.

The invention also encompasses host cells transformed with a nucleic acid or a vector according to the present invention and as described above. These cells may be obtained by introducing into an appropriate cell a nucleotide sequence or a vector as defined above, and then culturing the said cell under conditions allowing the replication and/or the expression of the transformed/transfected nucleotide sequence.

The host cell may be chosen from eukaryotic or prokaryotic system, such as for example bacterial cells, yeast cells, animal cells as well as plant cells. In the context of this invention a cell shall be understood to comprise higher biological systems. Such as animals, whole plants or parts thereof.

Furthermore, a host cell strain may be chosen which modulates the expression of the inserted sequences, or modifies and processes the gene product in the specific fashion desired.

A preferred host cell for the expression of the proteins of the invention consists of prokaryotic cells, such as gram negative or gram positive bacteria. A further preferred host cell according to the invention is a bacterium belonging to the *Bifidobacterium* family, more preferably belonging to the species *Bifidobacterium longum* or chosen from a microorganism associated with the species *Bifidobacterium longum*.

The transformed/transfected cells according to the invention may advantageously serve as a model and may be used in methods for studying, identifying and/or selecting compounds capable of being responsible for any of the beneficial effects brought about by the present *Bifidobacterium* strain.

The invention further provides polypeptides encoded by the *Bifidobacterium longum* ORFs, in particular those listed in table 1 and identified in the sequence listings. In the present description, the terms polypeptide, peptide and protein are used interchangeably. Furthermore the present invention also pertains to method for preparing such polypeptides by recombinant means comprising the steps of (a) culturing a host cell according to the present invention under conditions suitable to produce the polypeptide encoded by the polynucleotide; and (b) recovering the polypeptide from the culture.

It will be appreciated that the above polypeptides may also be obtained using combinatory chemistry, wherein the polypeptide is modified at some locations before testing them in model systems, so as to select the compounds which are the most active or which exhibit the desired properties.

In this context, chemical synthesis has the advantage of being able to use non-natural amino acids or nonpeptide bonds. Accordingly, in order to e.g. extend the life of the polypeptides according to the invention, it may be advantageous to use such non-natural amino acids, for example in the D form, or alternatively amino acid analogues, preferably sulphur-containing forms.

Finally, the structure of the polypeptides according to the invention, its homologous or modified forms, as well as the corresponding fragments may be integrated into chemical structures of the polypeptide type and the like. Accordingly, in order to preserve the polypeptide in an in vivo environment it will be preferred to provide at the N- and C-terminal ends compounds which convey a resistance to degradation to proteases.

It will also be appreciated that the different polypeptides according to the present invention and produced by the above method may represent antigens to the immune system of a host animal, so that antibodies may be produced directed against said polypeptides. These antibodies may be used for the detection of a polypeptide of interest in a mixture or generically of a strain of *Bifidobacterium* in a sample. In addition they may be used as research tools by e.g. producing antibodies against cellular surface epitopes and determining the effect of blocking certains polypeptides on the bacterial cell wall. Therefore, according to another aspect, the invention provides antibodies directed to epitopes on the various polypeptides provided by this invention.

According to another aspect the present invention also provides a method for the detection and/or identification of *Bifidobacterium longum* in a biological sample. This method may comprise several techniques known in the art, such as PCR or simply hybridisation with a suitable probe. Alternatively, an antibody raised against a cell wall epitope of *Bifidobacterium longum* may be used for said purpose. It will be appreciated that the above method may also be reversed and the presence of antibodies against *Bifidobacterium* may be determined by contacting the sample to be tested with a polypeptide of *Bifidobacterium* under conditions to allow formation of immune complexes.

The polypeptides according to the invention, the antibodies according to the invention described below and the nucleotide sequences according to the invention may be used in in vitro and/or in vivo methods for the detection and/or the identification of bacteria belonging to the species *Bifidobacterium* in a biological sample (biological tissue or fluid) which is likely to contain them. These methods, depending on the specificity of the polypeptides, of the antibodies and of the nucleotide sequences according to the invention which will be used, may detect and/or identify the bacterial variants belonging to the species *Bifidobacterium* as well as associated microorganisms capable of being detected by the polypeptides, the antibodies and the nucleotide sequences according to the invention which will be chosen. It may, for example, be advantageous to choose a polypeptide, an antibody or a nucleotide sequence according to the invention, which is capable of detecting any bacterium of the *Bifidobacterium* family by choosing a polypeptide, an antibody and/or a nucleotide sequence according to the invention which is specific to the family.

All the sequences referred to herein (SEQ ID. NO. 1 and SEQ ID. NO. 2) are listed in the attached sequence listings which is to be considered as part of the specification.

The invention also comprises the nucleotide sequences or polypeptides according to the invention covalently or noncovalently immobilized on a solid support. In the first case such a support may serve to capture, through specific hybridization, the target nucleic acid obtained from a biological sample to be tested. If necessary, the solid support is separated from the sample and the hybridization complex formed between the capture probe and the target nucleic acid is then detected by means of a second probe, called detection probe, labelled with an easily detectable element.

Such support may take the form of so-called DNA array or DNA chips, a multitude of molecular probes precisely organized or arrayed on a solid support, which will allow sequencing genes, studies of mutations contained therein and the expression of genes, and which are currently of interest given their very small size and their high capacity in terms of number of analyses.

The function of these arrays/chips is based on molecular probes, mainly oligonucleotides which are attached to a carrier having a size of generally a few square centimeters or more as desired. For an analysis the carrier (DNA array/chip) is coated with probes that are arranged at a predetermined location of the carrier. A sample containing fragments of a target nucleic acid to be analysed, for example DNA or RNA or cDNA, that has been labelled beforehand, is subsequently contacted with the DNA array/chip leading to the formation, through hybridization, of a duplex. After a washing step, analysis of the surface of the chip allows the effective hybridizations to be located by means of the signals emitted by the labels tagging the target. A hybridization fingerprint results from this analysis which, by appropriate computer processing, allows to retrieve information such as the expression of genes, the presence of specific fragments in the sample, the determination of sequences and the presence of mutations.

The hybridization between the probes of the invention, deposited or synthesized in situ on the DNA chips, and the sample to be analysed, may, e.g. be determined by means of fluorescence, radioactivity or by electronic detection.

The nucleotide sequences according to the invention may be used in DNA arrays/chips to carry out analyses of the expression of the *Bifidobacterium* genes. This analysis is based on DNA arrays/chips on which probes, chosen for their specificity to characterize a given gene, are present. The target sequences to be analysed are labelled before being hybridized onto the chip. After washing the labelled compounds are detected and quantified, with the hybridizations being carried out at least in duplicate. Comparative analyses of the signal intensities obtained with respect to the same probe for different samples and/or for different probes with the same sample, determine a differential transcription of RNA derived from the sample.

The DNA arrays/chips according to the present invention may also contain nucleotide probes specific for other microorganisms, which will enable a serial testing allowing rapid identification of the presence of a microorganism in a sample.

The principle of the DNA chip, as detailed above may also be used to produce protein chips on which the support has been coated with a polypeptide or an antibody according to the invention, or arrays thereof, in place of the DNA. These protein chips make it possible to analyse the biomolecular interactions (BIA) induced by the affinity capture of target analytes onto a support coated e.g. with proteins, by surface plasma resonance (SPR). The polypeptides or antibodies according to the invention, capable of specifically binding antibodies or polypeptides derived from the sample to be analysed, may thus be used in protein chips for the detection and/or the identification of proteins in samples.

The present invention also relates to a computer readable medium having recorded thereon one or more nucleotide and/or a polypeptide sequences according to the invention. This medium may also comprise additional information extracted from the present invention, such as e.g. analogies with already known sequences and/or information relating to the nucleotide and/or polypeptide sequences of other microorganisms so as to facilitate the comparative analysis and the exploitation of the results obtained. Preferred media are e.g. magnetic, optical, electrical and hybrid media such as, for example, floppy disks, CD-ROMs or recording cassettes.

The invention also relates to kits or sets for the detection and/or the identification of bacteria belonging to the species *Bifidobacterium longum* or to associated microorganisms, which comprises, a polypeptide according to the invention, where appropriate, the reagents for constituting the medium appropriate for the immunological or specific reaction, the reagents allowing the detection of the antigen-antibody complexes produced by the immunological reaction between the polypeptide(s) of the invention and the antibodies which may be present in the biological sample, it being possible for these reagents also to carry a label, or to be capable of being recognized in turn by a labelled reagent, more particularly in the case where the polypeptide according to the invention is not labelled, a reference biological sample (negative control) free of antibodies recognized by a polypeptide according to the invention, a reference biological sample (positive control) containing a predetermined quantity of antibodies recognized by a polypeptide according to the invention.

The invention also relates to a kit or set for the detection and/or the identification of bacteria belonging to the species *Bifidobacterium longum* or to an associated microorganism, or for the detection and/or the identification of a microorganism, wherein the kit comprises a protein chip according to the invention.

The novel microorganism termed NCC2705, described herein by way of its genomic sequences, has been deposited according to the Budapest Treaty with the Institute Pasteur on Jan. 29, 2001 and received the deposit no. CNCM I-2618. This microorganism belongs to the genus *Bifidobacterium*, species *Bifidobacterium longum* and is a probiotc microorganism, i.e. it may pass the gastro-intestinal tract in an essentially live and viable form and has the capability of preventing colonization of the intestine with pathogenic bacteria causing diarrhea and in addition may prevent or reduce the occurrence of infection of intestinal cells by rotaviruses.

The microorganism is gram positive, catalase negative and $CO_2$ production negative, it produces L(+) lactic acid and essentially prevents colonization of intestinal cells by bacteria bringing about diarrhea, such as pathogenic *E. coli*, e.g. enteropathogenic *E. coli* (EPEC), or *salmonella*, e.g. *Salmonella typhimurium* and prevents infection of intestinal cells by rotaviruses.

The novel microorganism may be used for the preparation of a variety of carrier materials, such as e.g. milk, yogurt, curd, fermented milks, milk based fermented products, fermented cereal based products, milk based powders, infant formulae and may be included in the support in an amount of from about $10^5$ cfu/g to about $10^{11}$ cfu/g. For the purpose of the present invention the abbreviation cfu shall designate a "colony forming unit" that is defined as number of bacterial cells as revealed by microbiological counts on agar plates.

The present invention also provides a food or a pharmaceutical composition containing at least the *Bifidobacterium* NCC 2705 and/or containing a supernatant, in which the microorganisms have been grown or an active fraction/ metabolite thereof, respectively.

For preparing a food composition according to the present invention at least one of the Bifidobacteria of the present invention is incorporated in a suitable support, in an amount of from about $10^5$ cfu/g to about $10^{12}$ cfu/g, preferably from about $10^6$ cfu/g to about $10^{10}$ cfu/g, more preferably from about $10^7$ cfu/g to about $10^9$ cfu/g.

In case of a pharmaceutical preparation the product may be prepared in form of tablets, liquid bacterial suspensions, dried oral supplements, wet oral supplements, dry tube feeding or a wet tube feeding with the amount of the *Bifidobacterium*/Bifidobacteria to be incorporated therein being in the range of up to about $10^{12}$ cfu/g, preferably from about $10^7$ cfu/g to about $10^{11}$ cfu/g, more preferably from about $10^7$ cfu/g to about $10^{10}$ cfu/g.

The activity of the novel microorganism in the individual's intestine is of course dose dependent. That is, the more the novel microorganism or an active component thereof is incorporated by means of ingesting the above food material or the pharmaceutical composition the higher the protective and/or curing activity. Since the novel microorganism is not detrimental to mankind and animals and has eventually been isolated from baby feces a high amount thereof may be incorporated so that essentially a high proportion of the individual's intestine will be colonized by the novel microorganisms.

Yet, according to another preferred embodiment the supernatant of a culture of the *Bifidobacterium* of the present invention, or an active fraction thereof, may be used for preparing the carrier. The supernatant may be used as such or may be dried under conditions that do not destroy the metabolic compounds secreted by the microorganisms into the liquid medium, such as e.g. freeze drying, and may be included in the carrier. In order to minimize the number of unknown compounds in the supernatant the Bifidobacteria will preferably be grown in a defined media, the composition of which is known and does not negatively affect the host incorporating it. Further, the skilled person will, based on his general knowledge optionally deplete the supernatant from unwanted products, such as e.g. by means of chromatography.

The present inventors have investigated baby feces and isolated a variety of different bacterial strains therefrom. These strains were subsequently examined for their capability to prevent prevent colonization and/or invasion of epithelial cells with bacteria that are known to cause diarrhea, such as *E. coli, Sigella, Klebsiella, Yersinia, Pseudomonas aeruginosa Listeria, Streptococcus, Staphilococcus, Clostridium difficile, H. pyori* and also *Candida albicans*.

Several bacterial genera comprising *Bifidobacterium, Lactococcus* and *Streptococcus* were screened for their diarrhea inhibitory properties. The tests for the inhibitory property were performed with pathogenic microorganisms, such as *E. coli, Klebsiella, Yersinia, Pseudomonas aeruginosa, H. pyori*, and *Salmonella typhimurium* as representatives for pathogenic microorganisms causing diarrhea in affected individuals.

The various bacteria were grown in a suitable medium, such as MRS, Hugo-Jago or M17 medium at temperatures of from about 30 to 40° C. corresponding to their optimal growth temperature. After reaching stationary growth the bacteria were collected by centrifugation and resuspended in physiological NaCl solution. Between the different tests the bacterial cells were stored frozen (−20° C.).

For assessing antibacterial properties the following approaches were chosen.

According to one protocol the cultured *Bifidobacterium* of the present invention was examined for its capability to decrease the viability of the different pathogenic microorganisms. To this end, a culture of pathogenic bacteria was contacted with a concentrated supernatant of a *Bifidobacterium* culture and the growth potential of the pathogenic bacteria was assessed.

According to a second protocol the adhesion capability of the Bifidobacteria of the present invention to $T_{84}$ cells, a cell culture model for the intestine, was determined by culturing the *Bifidobacterium* with $T_{84}$ cells and the rate of adhesion was assessed.

According to another protocol the potential of the *Bifidobacterium* of the present invention to prevent infection of intestinal cells by *Salmonella*, using the cell line Caco-2 as a model for the intestine, was determined. In this respect, the supernatant of a cell culture of the Bifidobacteria of the present invention was added together with the pathogenic microorganism to the intestinal cells and the rate of adhesion, or invasion, respectively, was assessed.

Thus, it could be shown that the cultured *Bifidobacterium* and the supernatant proofed to be extremely effective in preventing both adhesion to and invasion into the intestinal cells indicating that one or more metabolic compounds secreted by the microorganism is/are likely to be responsible for the anti-diarrhea activity.

According to yet another protocol it was further assessed, whether NCC2705 would be capable to prevent invasion of epithelial cells by rotaviruses. Two different protocols were applied. According to one protocol the various bacterial strains were examined for their direct interaction with the rotavirus strain while in the second protocol the bacteria were screened for those strains that interact with cellular rotavirus receptors.

The first protocol involved contacting the respective bacterial suspension each with a different rotavirus strain and incubating in suitable media. Subsequently, the virus-bacteria mixture was applied to a monolayer of cells of the human undifferentiated colon adenoma cells HT-29 (intestinal epithelial cell line) and incubation was continued. Virus replication was then assayed.

The second protocol involved incubating the respective bacterial suspension first together with a monolayer of cells of the human undifferentiated colon adenoma cells HT-29 and adding the virus subsequently. After continued incubation virus replication was assayed.

Rotavirus replication was assessed by histo-immunological staining of rotavirus proteins in infected cells. A rotavirus inhibitory effect was attributed to a given bacterium when the number of infected cells was reduced by 90% in the cell culture inoculated with rotavirus plus the indicated bacteria in comparison with cells inoculated only with rotavirus.

The present invention will now be described by way of examples without limiting the same thereto.

Media and solutions

MRS (Difco)

Hugo-Jago (tryptone 30 g/l (Difco), yeast extract 10 g/l (Difco), lactose 5 g/l (Difco), $KH_2PO_4$ 6 g/l, beef extract 2 g/l (Difco), agar 2 g/l (Difco))

M17 (Difco)

Eugon Tomato Agar (Canned tomato juice 400 ml, Eugon agar BBL 45.5 g, Maltose Difco 10 g, Hemin Sigma 5 mg, Agar Difco 5 g, distilled water 600 ml)

DMEM (Dulbecco's modified Eagle medium)

CFA (according to Ghosh et al. Journal of Clinical Microbiology, 1993 31 2163–6) Müiller Hinton agar (Oxoid)

LB (Luria Bertami, Maniatis, A Laboratory Handbook, Cold Spring Harbor, 1992)

$C^{14}$-acetate (53,4 Ci/mMol, Amersham International PLC)

PBS (NaCl 8 g/l, KCl 0.2 g/l, $Na_2HPO_4$ 1.15 g/l, $KH_2PO_4$ 0.2 g/l))

Trypsin-EDTA solution (Seromed)

FCS Fetal calf serum (Gibco)

*E. coli* DAEC C 1845 was obtained from Washington University, Seattle and *E. coli* JPN15 was obtained from the Center for Vaccine Development of the University of Maryland, USA). The *Salmonella typhimurium* strain SL1344 was obtained from the department of Microbiology, Stanford University, CA, USA. This strain acts as a pathogen on mice and is resistant to Streptomycin. It adheres to Caco-2 colon cells (Finlay and Falkow, 1990). The *Klebsiella* was obtained from stock clinical isolates from the microbiological laboratory of the Faculté de Pharmacie Paris XI, Châtenay-Malabry, France. The *Yersinia* was obtained from INSERM Unit 411, Hôpital Necker, Paris, France. The *Pseudomonas aeruginosa* was obtained from stock clinical isolates from the microbiological laboratory of the Faculté de Pharmacie Paris XI, Châtenay-Malabry, France.

The *H. pylori* was obtained from Institute of Microbiology, Lausanne University, Lausanne, Switzerland.

Human rotavirus Wa (G1 serotype) and simian rotavirus SA-11 (G3 serotype) were obtained from P. A. Offit, Children's Hospital of Philadelphia, U.S.A. The DS-1xRRV reassortant virus was obtained from A. Kapikian, NIH Bethesda, U.S.A. The serotype 4 human rotavirus Hochi was obtained from P. Bachmann, University of Munich, Germany.

EXAMPLE 1

Isolation of Bifidobacteria

Fresh feces were harvested from diapers of 16 healthy babies 15 to 27 days old. 1 g of fresh feces was placed under anaerobic conditions for transportation to the laboratory and microbiological analyses were run within 2 hours from sampling by serial dilutions in Ringer solution and plating on selective media. Eugon Tomato Agar (Canned tomato juice 400 ml, Eugon agar BBL 45.5 g, Maltose Difco 10 g, Hemin Sigma 5 mg, Agar Difco 5 g, distilled water 600 ml) incubated anaerobically at 37° C. for 48 hours was used to isolate bifidobacteria. Colonies were randomly picked up and purified. Physiological and genetic characterisation was performed on the isolates.

EXAMPLE 2

Cultivating Cell Lines

Caco-2 Cells

For the inhibition assays the cell line Caco-2 was utilized as a model of mature enterocytes of the small intestine. This cell line presents characteristic of intestinal cells such as e.g. polarization, expression of intestinal enzymes, production of particular structural polypeptides etc. The cells were grown on different supports, namely on plastic dishes (25 cm$^2$, Corning) for growth and propagation, on defatted and sterilized 6 well glass plates (22×22 mm, Corning) for the adhesion and the inhibition tests. After the second day in culture the medium (DMEM) was changed on a daily basis. Before use the medium was supplemented with 100 U/ml penicilline/streptomycine, 1 μg/ml amphoterine, 20% FCS inactivated at 56° C. for 30 min and 1% of a solution containing non-essential amino acids (10 mM) (Eurobio, Paris, France). Culturing was performed at 37° C. in an atmosphere comprising 90% air and 10% $CO_2$. The cells were splitted every six days. The cells were detached from the walls of the well by treatment in PBS with 0.015% trypsine and 3 mM EDTA at pH 7.2. For neutralizing the effect of trypsine an equal volume of the culture medium containing FCS was added to the cell suspension obtained, the mixture was centrifuged (10 min at 1000 rpm) and the pellet was again dissolved in culture medium. Living cells (not dyed with trypane blue) were counted. About 3.5×10$^5$ living cells were transferred to a new culture bottle and about 1.4×10$^5$ cells per well and cultivated until a confluent monolayer was obtained.

$T_{84}$ Cells

For the adhesion assays the cell line $T_{84}$ was utilized as a model of colon cells from the intestine. This cell line presents characteristics of intestinal cells such as e.g. polarisation, expression of intestinal enzymes, production of particular structural polypeptides etc. $T_{84}$ cells were obtained from University of California, San Diego, Calif. Cells were grown in DMEM (50%) and Ham's F12 (50%) supplemented with 2 mM glutamine, 50 mM HEPES, 1% non-essential amino acids and 10% inactivated (30 min, 56° C.) fetal calf serum (Boehringer, Mannheim, Germany) at 37° C. in a 10% $CO_2$/90% air atmosphere. Cells were seeded at a concentration of 10$^6$ cells per cm$^2$. Cells were used for adherence assays at late post-confluence, i.e., after 10 days.

EXAMPLE 3

Cultivating Bacterial Cells

All strains except Bifidobacteria were kept at −80° C. in their culture medium containing 15% glycerol. As the number of transfers into new media has an influence on the adhesion factors, the *Salmonella* strain was only transferred twice within a period of 24 hours, the first transfer taking place when the strain was frozen. All cultures were raised aerobically.

Bifidobacteria

The bacterial strain (*Bifidobacterium longum* CNCM I-2618 (NCC2705) was stored at −20° C. in MRS medium containing 15% glycerol. The strain was grown under anaerobic conditions in MRS and transferred twice to new media at intervals of 24 hours before use in the inhibition assays. For the assay a concentration of 2×10$^9$ cfu/ml was utilized. The supernatant was collected by centrifugation for 1 hour at 20.000 rpm and the supernatant obtained was subsequently checked for the presence of bacteria. The strains of *Bifidobacterium* were cultivated anaerobically in MRS during 18 hours at 37° C. The cultures were then centrifuged (20 min. at 4° C.), the supernatant was collected, lyophilized, returned to the solution and then concentrated ten times (10×). The pH of the supernatant was finally adjusted to 4.5.

*E. coli* C 1845

The first passage after thawing was effected on a CFA—Müiller Hinton agar, which is suitable to effect expression of adhesion factors by the bacterium. Before each experiment the bacterial cells were incubated at 37° C. with a transfer to a new medium being effected twice after 24 hours each.

*Klebsiella*

Bacteria were grown overnight for 18 hrs at 37° C. in Luria broth.

*Yersinia*

Bacteria were grown overnight for 18 hrs at 37° C. in Luria broth.

*Pseudomonas aeruginosa*

Bacteria were grown overnight for 18 hrs at 37° C. in Luria broth.

*H. pylori*

Bacteria were grown on Brain-Heart Infusion (BHI)-agar plates containing 0.25% yeast extract (Difco Laboratories, Detroit, Mich.), 10% horse serum and 0.4% *Campylobacter* selective complement (Skirrow supplement, SR 69; Oxoid Ltd, Basingstoke, England).

EXAMPLE 4

Adhesion of B128/Ca1 and BL29/F9 to $T_{84}$ and Caco-2 Cells

The Caco-2 and $T_{84}$ monolayers, prepared on glass coverslips which were placed in six-well Corning tissue culture plates (Corning Glass Works, Corning, N.Y.), were washed twice with phosphate-buffered saline (PBS). Bifidobacteria (1 ml, 4×10$^8$ bacteria/ml in spent culture supernatant, treated-supernatant or fresh MRS broth) were added to 1 ml of the cell line culture medium. This suspension (2 ml) was added to each well of the tissue culture plate and the plate incubated at 37° C. in 10% $CO_2$/90% air. After 1 hour of incubation, the monolayers were washed five times with sterile PBS, fixed with methanol, stained with Gram stain, and examined microscopically. Each adherence assay was conducted in duplicate over three successive passages of intestinal cells. For each monolayer on a glass coverslip, the number of adherent bacteria was evaluated in 20 random microscopic areas. Adhesion was evaluated by two different technicians to eliminate bias.

The results are shown in FIG. 1 from which it becomes obvious that NCC2705 is capable to adhere to intestinal cells as compared to the known cell line GG (WO 97/00078), La1 (EP 0 577 903) or another Bifido strain (BL28/Ca1).

EXAMPLE 5

Anti-Pathogenic Activity of the Bifidobacteria

As candidates for pathogenic bacteria *E. coli, Klebsiella, Yersinia, Pseudomonas aeruginosa* and *H. pyori* were used.

Based on a culture of NCC2705 kept in MRS medium for 18 hours, an exponentially growing culture was produced (3 hours at 37° C.). 2 ml of this solution were removed and centrifuged for 5 min. at 5500 g, +4° C. After collection of the supernatant the cell pellet was washed in sterile PBS. After centrifuging, the pellet was collected and 2 ml of sterile PBS were added. The bacteria were counted and the suspension was adapted in such a way that between 1 and $5 \times 10^6$ bacteria/ml were produced.

Figure 2:
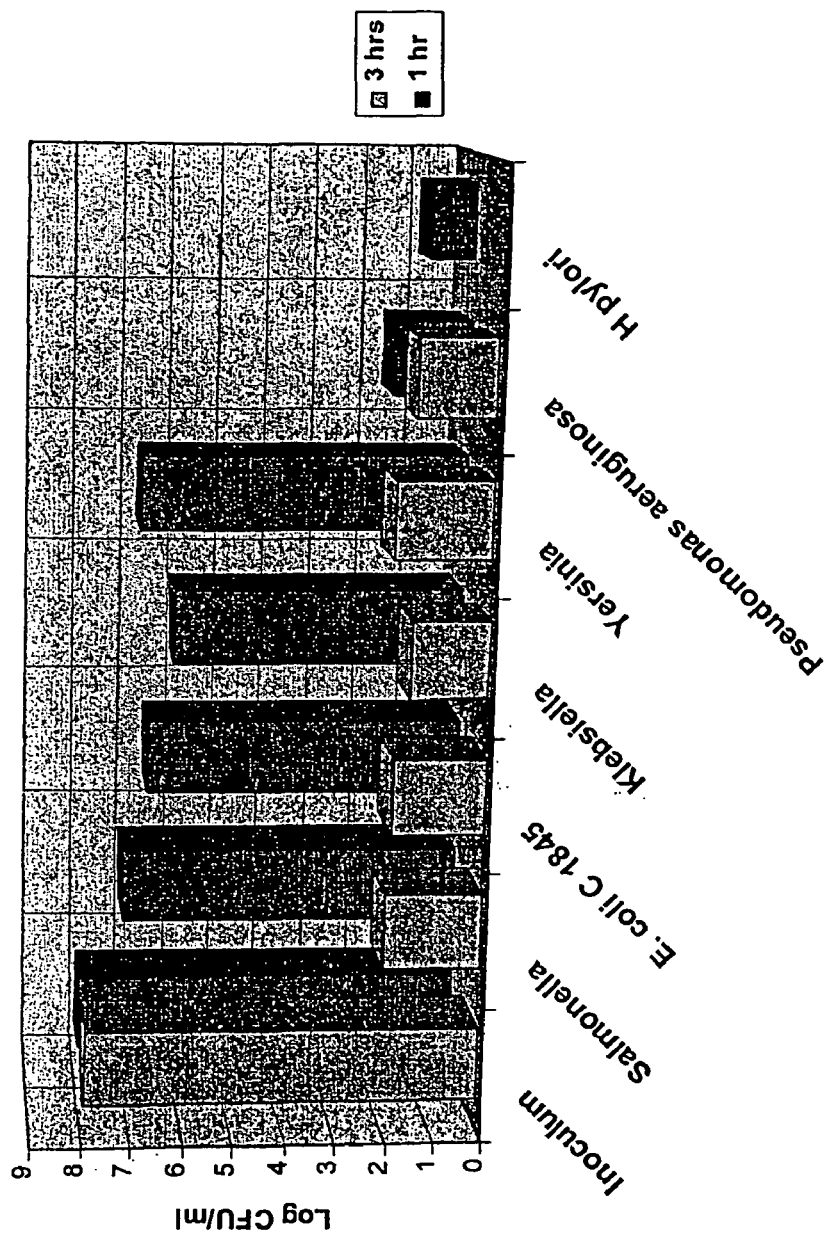
FIG. 2 shows the pathogen sensitivity of pathogenic bacteria towards *Bifidobacterium longum* NCC2705.
Figure 3:
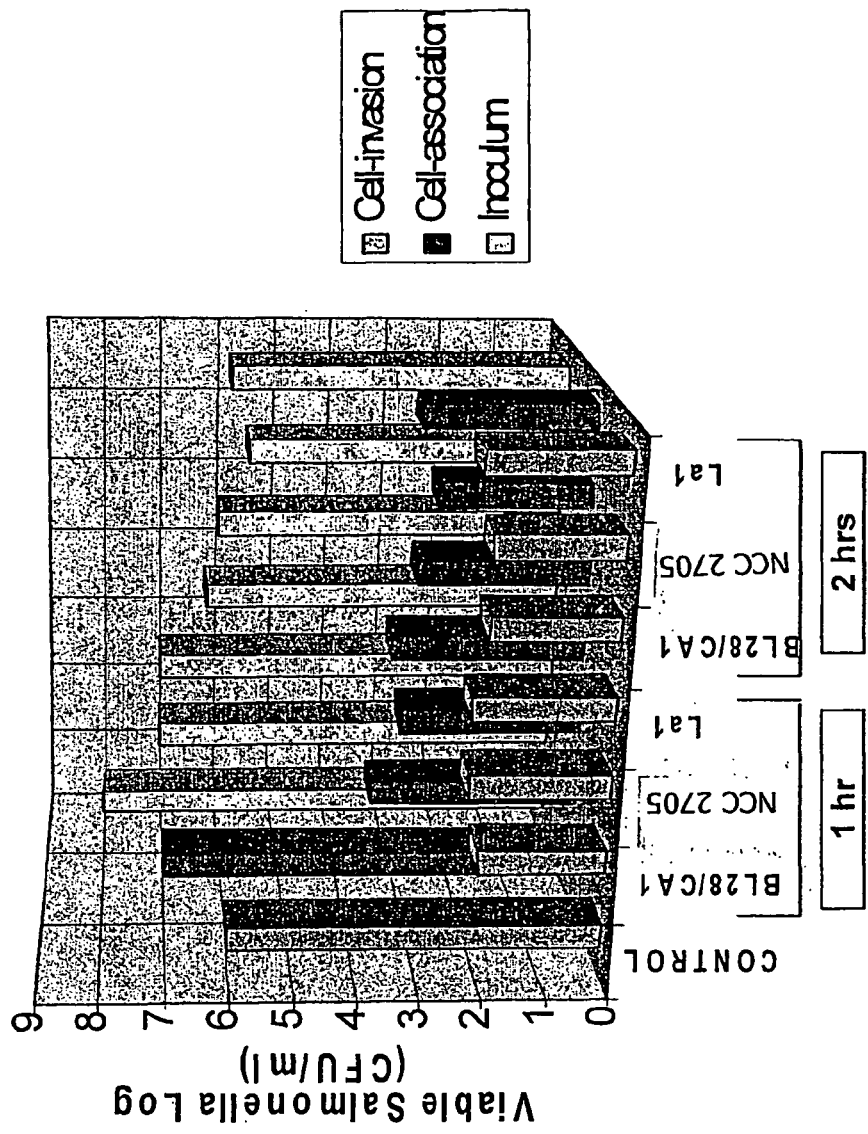
FIG. 3 shows the activity of the cell lines NCC2705 and B1 28 against *S. typhimurium* SL1344 infecting Caco-2 cells.

The assessment of the antimicrobial effect exerted by the Bifidobacteria of the present invention was carried out according to the Lehrer method described in Lehrer et al., J. Imunol. Methods 137 (1991), 167–173, which document is incorporated here by way of reference. The results thereof are shown in FIGS. 2 and 3.

From the above results it may be seen that the *Bifidobacterium* of the present invention may effectively inhibit growth of the various pathogenic bacteria.

EXAMPLE 6

Inhibition Assay for *salmonella*

Salmonella are bacteria that invade epithelial cells and multiply therein. For determining the inhibitory activity of the Bifidobacteria of the present invention towards *Salmonella typhimurium* the strain SL1344 and following procedure was used.

The pathogenic cells were cultivated in LB-medium. After the second passage to new medium the bacterial strains were marked with radioisotopes using $C^{14}$-acetate at 10 μCi/ml in LB-medium. Incubation of the strains in this medium was performed for 18 hours at 37° C.

The bacterial suspension was subsequently subjected to centrifugation (1041 rpm, 15 min) so as to eliminate the remaining $C^{14}$-acetate from the supernatant. The pellet was suspended and washed in PBS and the cells were suspended at a concentration of about $10^8$ cells/ml in 1% sterile mannose. Mannose is known to inhibit non specific adhesion. The bacterial solution was then adjusted to $2 \times 10^8$ cells/ml.

The pathogen (1 ml; $2 \times 10^8$ cells) and an aliquot of a supernatant (1 ml) of a *Bifidobacterium* culture are pre-incubated for 2 hours at 37° C. The suspension is subsequently centrifuged, the resulting supernatant is removed and the pellet is again suspended in 0.5 ml PBS. This pathogen solution (0,5 ml) is then brought in contact with human intestine cells in culture. The culture was washed with sterile PBS twice and 0,5 ml adhesion medium (DMEM) was added. The cells are then incubated for 1 hour at 37° C. under 10% $CO_2$.

After incubation the number of bacteria in the incubation medium and on/in the intestinal cells are counted. In order to determine the amount of cells adhering on or having invaded into the intestinal cells the following approaches have been chosen.

For determining the number of adhering bacteria the medium was decanted and the cells were washed once with culture medium and once with sterile PBS. Subsequently, 1 ml of sterile $H_2O$ was added per compartment, to lyse the cells and to form a cell solution which was incubated for 1–2 hours at 37° C., after which successive dilutions were carried out. In order to count the number of adhering and invasive bacteria, the cell solution was centrifuged to remove cell debris and the radioactivity was measured.

According to another protocol 10 aliquots were each put on TSA medium. The media were then incubated for 18–24 hours at 37° C.

For determining the amount of invaded bacteria the Caco-2 cells were washed with PBS so as to eliminate all non-adhering cells. Subsequently, a medium containing gentamycin (20 μg/ml) was added and incubation was continued for 1 hour at 37° C. Gentamycin is an antibiotic not penetrating intestinal cells so that all extracellular microorganisms were killed, while bacteria having already invaded intestinal cells will survive. The cells were then incubated for another hour at 37° C. and were then washed twice with PBS. The cells were lysed by addition of and incubation in sterile distilled water for 1–2 hours at 37° C. After removing the cell debris radioactivity was determined. According to another protocol successive dilutions were carried out, which were put on TSA medium. Incubation: 18–24 hours at 37° C.

It may be seen that cultured cells and the culture supernatant were extremely effective in preventing adhesion of and invasion into intestinal cells by *Salmonella*.

EXAMPLE 7

Infection of Mice by the Strain *S. typhimurium* C5

Adult, 7–8 weeks old, axenic, female mice (C3H/He/oujco conventional, Iffa Credo, France), raised under sterile conditions, were orally infected with a fixed concentration of *S. typhimurium* (0,2 ml, $10^8$ cfu/mouse). Some mice were rendered monoxenic by the implantation of a range of Bifidobacteria strains. With some mice, the Bifidobacteria in segments of the intestine were counted after its removal and mincing of the organs in PBS. With other mice, the protection against infection was assessed in such a way that they were continuously kept in a sterile environment and the days of survival were compared to the control group.

Figure 4:
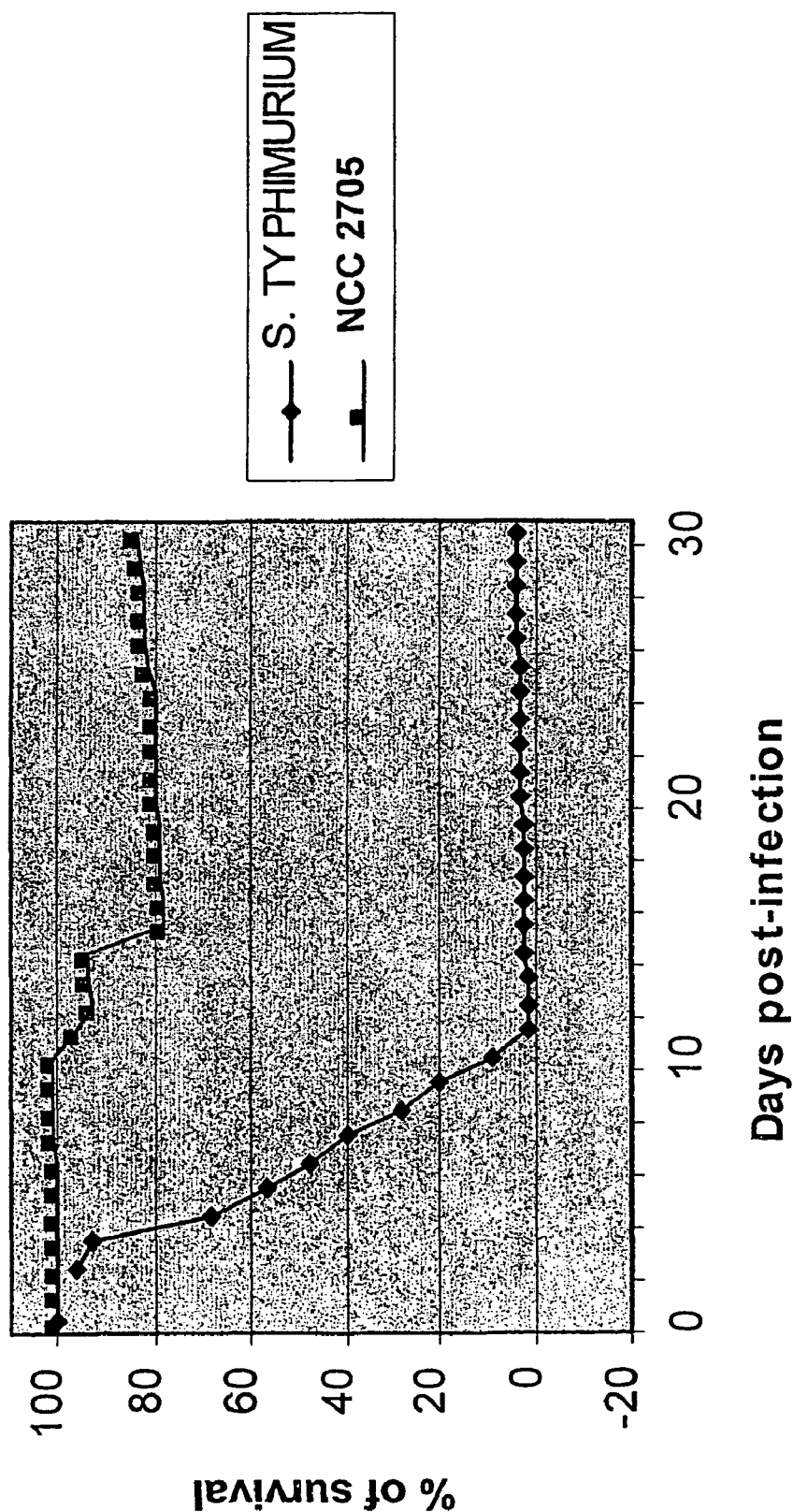
FIG. 4 shows the rate of survival of mice infected with *Salmonella typhimurium* SL 1344 and treated with the *Bifidobacterium* NCC2705.
Figure 5:
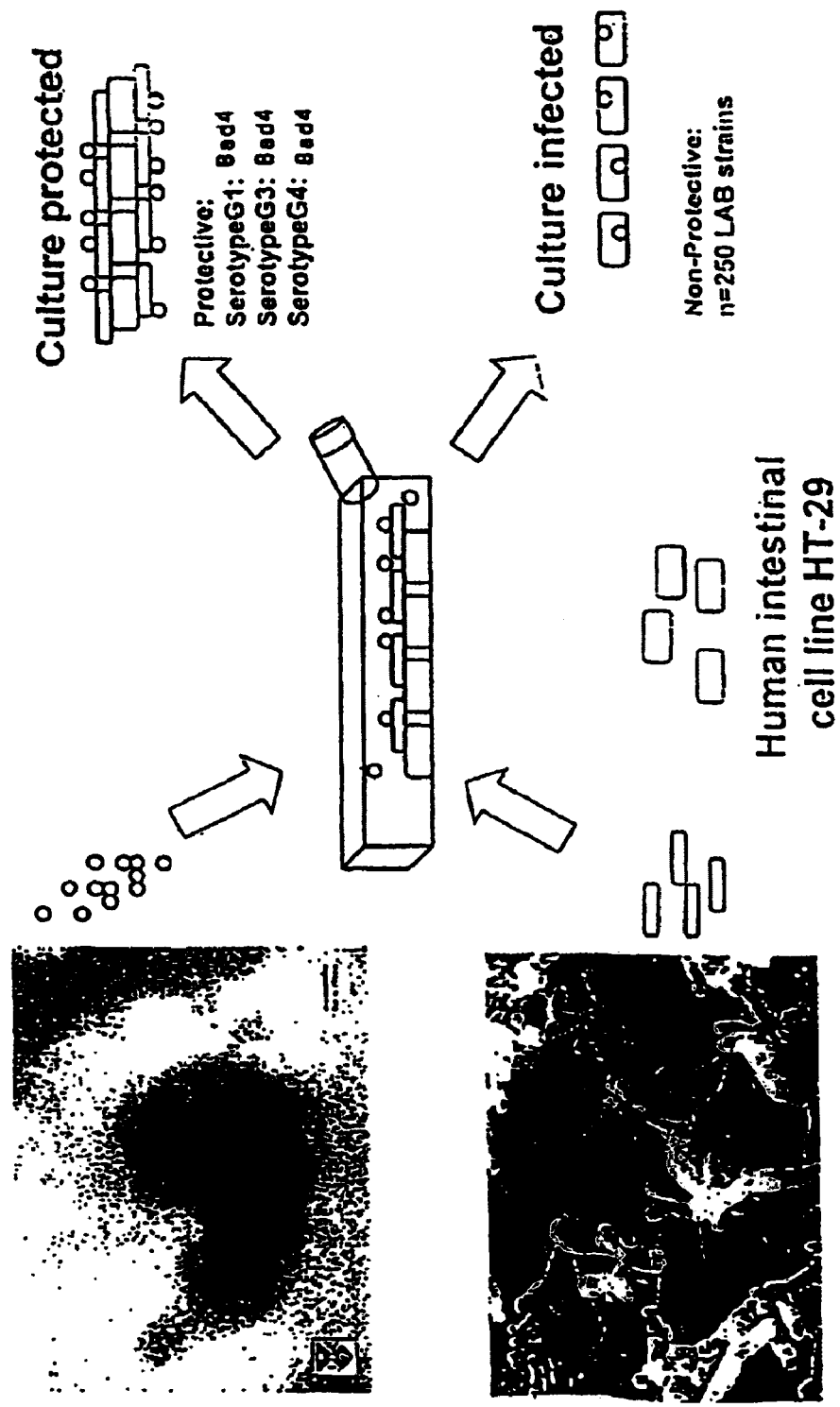
FIG. 5 shows a scheme illustrating the cell culture screening for assessing rotaviral protective properties of the bacterial strain NCC 2705.

The results are shown in FIG. 4. As may be derived therefrom in the control group nearly all mice died after a time period of about 10 days. In contrast thereto, all mice treated with NCC2705 were alive after 10 days with only 20% dying from the detrimental effect exerted by *Salmonella* after a period of 30 days.

EXAMPLE 8

$1^{st}$ Protocol

30 μl of the respective bacterial suspension (containing on average $3 \times 10^6$ bacteria) were mixed with 70 μl M199 medium supplemented with 10% tryptose phosphate broth (Flow) and 5% trypsin-EDTA solution (Seromed) to which were added 100 µl of virus in supplemented M199 medium. The virus-bacteria mixture thus obtained was incubated for 1 hour at 4° C. and for 1 hour at 37° C. Separately, cells of the human undifferentiated colon adenoma cells HT-29 growing as a confluent monolayer in 96-well microtiter plates (in M199 medium supplemented with 10% tryptose phosphate broth (Flow) and 5% trypsin-EDTA solution (Seromed) 1:4 diluted with PBS) were washed three times with phosphate-buffered saline (PBS; pH 7.2). The virus-bacteria mixture processed as indicated above was transferred to the cells and the microtiter plates were incubated for 18 h in a $CO_2$ incubator (Heraeus). Virus replication was assayed as described below.

$2^{nd}$ Protocol

30 µl of the bacterial suspension (supra) were mixed with 70 µl M199 medium supplemented with 10% tryptose phosphate broth (Flow) and 5% trypsin-EDTA solution (Seromed) and applied directly on HT-29 cells grown and pretreated as described in the $1^{st}$ protocol in the microtiter plates. After one hour incubation at 37° C. 100 µl of virus in supplemented M199 medium were added to the cells in the microtiter plates. The incubation was continued for 18 h in a $CO_2$ incubator (Heraeus). Virus replication was assayed as described below.

The rotavirus replication was assessed by histo-immunological staining of rotavirus proteins in infected cells as described hereafter.

One day after infection, the cell culture medium was removed from the microtiter plates and the cells were fixed with absolute ethanol for 10 min. Ethanol was discarded, and the plates were washed three times in PBS buffer. Then 50 µl of an anti-rotavirus serum (mainly directed against VP6 protein), produced in rabbits (obtained from the ISREC University of Lausanne) and diluted 1:2000 in PBS was added to each well and incubated for 1 h at 37° C. with a cover slip to prevent desiccation of the wells. The anti-serum was discarded afterwards and the plates were washed three times with PBS. Then 50 µl of anti-rabbit immunoglobulin G (IgG) antiserum produced in goats and coupled to peroxidase (GAR-IgG-PO; Nordic) were added at a dilution of 1:500 in PBS to each well and the plates were incubated for 1 hour at 37° C. The serum was discarded and the plates were again washed three times with PBS. Then 100 µl of the following substrate mixture was added to each well: 10 ml of 0.05 M Tris-hydrochloride (pH 7.8), 1 ml of $H_2O_2$ (30% suprapur, diluted 1:600 in $H_2O$; Merck) and 200 µl of 3-amino-9-ethylcarbazole (0.1 g/10 ml of ethanol stored in 200 µl aliquots at −80° C.; A-5754; Sigma). The plates were incubated for at least 30 min at room temperature. The substrate was discarded and the wells were filled with 200 µl of $H_2O$ to stop the reaction. Infected cell foci were counted with an inverted microscope (Diavert; Leitz).

Only very few bacterial strains interacted with rotaviruses. Merely 4 out of the 260 bacterial cells primarily selected inhibited rotavirus replication in at least one protocol. *Bifidobacterium adolescentis* CNCM I-2618 (NCC2705) showed an extremely high activity against Serotype 1 Rotavirus, Serotype 3 rotavirus SA-11 and Serotype 4 rotavirus Hochi.

NCC2705 is gram positive and catalase negative, it does not produce $CO_2$ during fermentation and produces just L (+) lactic acid according to methods disclosed in the "Genera of lactic acid bacteria", Ed. B. J. B. Wood and W. H. Holzapfel, Blackie A&P.

These results show the extreme superior properties of the *Bifidobacterium* of the present invention.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A biologically pure culture of a *Bifidobacterium longum* strain comprising a genomic sequence identified by SEQ ID NO: 1 and a plasmid sequence identified by SEQ ID NO: 2.

* * * * *